United States Patent [19]
Farb et al.

[11] Patent Number: 6,066,726
[45] Date of Patent: May 23, 2000

[54] NEURON-SPECIFIC TRANSCRIPTIONAL PROMOTER

[75] Inventors: David H. Farb; Shelley J. Russek, both of Cambridge, Mass.

[73] Assignee: Trustees of Boston University, Boston, Mass.

[21] Appl. No.: 08/889,502

[22] Filed: Jul. 8, 1997

Related U.S. Application Data

[63] Continuation of application No. PCT/US96/18830, Nov. 8, 1996.
[60] Provisional application No. 60/006,509, Nov. 9, 1995.
[51] Int. Cl.[7] ............................ C07H 21/04; C12N 15/11; C12N 15/85
[52] U.S. Cl. ........................ 536/24.1; 536/23.1; 536/24.5; 435/353; 435/368; 435/375
[58] Field of Search ................................ 435/6, 440, 353, 435/368, 375; 536/23.1, 24.1, 24.3, 24.31, 24.5

[56] References Cited

PUBLICATIONS

Kirkness et al., EMBL3, Accession No. M59212, Aug. 6, 1991.

*Primary Examiner*—George C. Elliott
*Assistant Examiner*—Mark L. Shibuya
*Attorney, Agent, or Firm*—Kevin M. Farrell

[57] ABSTRACT

The 5'-flanking region and core regulatory domains that underlie neuronal specific expression of the human γ-aminobutyric acid type A ($GABA_A$) receptor β1 subunit gene are identified herein. Sequence analysis, mapping of transcriptional initiation sites, and transfection of reporter gene constructs into primary cultures demonstrate that neuronal and region specific activity resides in a TATA-less minimal promoter of 186 bp, comprising an initiator, the major transcriptional start site, a presumptive TFIID binding site, and an enhancer. Enhancer sequence contained within a 26 bp region at the 5'-end of the minimal promoter is essential for activity but not for tissue specificity. Moreover, β1 promoter activity is subject to autologous inhibition, indicating that GABA-induced receptor mRNA downregulation results from an inhibition of gene transcription. Regulation of neurotransmitter receptor gene expression plays an important role in nervous system development and function, and impaired gene regulation may underlie the etiology of certain neurological diseases.

28 Claims, 21 Drawing Sheets

```
         Met
 -26     +1                                20
GACAATTCTTTTAATCAGAGTTAGTAATGTGGACAGTACAAAATCGA    SEQ ID NO: 20
                    40              60
GAGAGTCTGGGGCTTCTCTCTTTCCCTGTGATGATTACCATGGTCTG

70       Se              CAAT
TTGTGCACACAGgtgagctgctgttgttgaatctctctctctctctc tcttttttcttggtatgtttcttttacgtgtctgctggatcatgt TATA
atcttgttgtttgggggtaggtgtgcctgtatctttttatatgtgct TRN INIT
cacagtttgtgctcattttgaatacggccctacttcttcccttag 100              120
CACCAATGAACCCAGCAACATGTCATACGTGAAAGAGACAGTGGACA 140              160       172
GATTGCTCAAAGGATATGACATTCGCTTGCGGCCGGACTTCGGAGgt aacgcttcatctttttttcaacctgtaacccatccttagttctccttt tctatcaaagataaatgtcaaaaaaaaaaaaaaaaaaaaaaggcatg tcattttcgtaagcgtgcactataccctggacacacacacacacaca cacacacacacacacacaccaccccgggtcccccagtctcaggtttg gatgaatcctcaggcggagggcgaccttctcccccccgggccgacaca cctctgcatagtcactgcatcacgtgtgtgcccacacctgttttccc aggcagtccctgaaagggtggtggggggagcagggagggagcccgt taagaatggagtaagggctgggaagcccccagaccctccccagcctg ctgtcactgagagaatctgttcctaatgtggcccacctccccggcag 173   180              200
GGCCCCCCGTCGACGTTGGGATGAGGATCGATGTCGCCAGCATAGAC 220          240
ATGGTCTCCGAAGTGAATATG
```

FIG. 4

```
                        Exon 1
Rat β1     G-AAAGACAATTC-TTTCATCAGAGTTAGTAATGTGGACAGTACAAAATCGAGA    SEQ ID NO: 21
           | |||||||||| ||||||||||||||||||||||||||||| |||| |||||
Human β1   GAAAAGACAATTCTTTTAATCAGAGTTAGTAATGTGGACAGTCAAAACGAGAGA    SEQ ID NO: 22

Rat        GAGTTTGGGGCTTCTCTCTTTTCCTGTGATGGTTGCCATGGTTTGTTGTGACAC    SEQ ID NO: 23
           ||||| ||||||||||||||||| |||||||||||||||||||||||||||||
Human      GAGTCTGGGGCTTCTCTCTCTTTCCCTGTGATGATTACCAAGGTGTGTGTGACAC    SEQ ID NO: 24
                                              Exon 2
              ◇
Rat        AGCTCCAATGAACCCAGCAACATGTCATACGTGAAAGAGACAGTGGACCGACTG    SEQ ID NO: 25
           || |||||||||||||||||||||||||||||||||||||||||||||| |||
Human      AGCACCAATGAACCCAGCAACATGTCATACGTCATACGTGAAAGAGACAGTGGACAGATTG    SEQ ID NO: 26

Rat        GCTCAAAGGATATGACATTCGCTTGCGGCCCAGACTTTGGAGGGCCCCGGTGGA    SEQ ID NO: 27
           ||||||||||||||||||||||||| ||||||||||||||||||||| |||||
Human      GCTCAAAGGATATGACATTCGCTTGCGGCCGGACTTCGGAGGGCCCCCCGTCGA    SEQ ID NO: 28
                                Exon 3
Rat        CGTCGGGATGCGGATCGATGTCGCCAGCATAGACATGGTCTCGGAAGTGAA      SEQ ID NO: 29
           ||| |||||| |||||||||||||||||||||||||||||||| ||||||
Human      CGTTGGGATGAGGATCGATGTCGCCAGCATAGACATGGTCTCCGAAGTGAA      SEQ ID NO: 30
```

FIG. 5

| | Exon 1 | Intron 1 | | | Exon 2 | |
|---|---|---|---|---|---|---|
| | | 5' Donor | | 3' Acceptor | | |
| Hβ1 | CAC AG<br>His Se | gtgagctg | ctg tt gtt | gaatctctct ctctct ...tag | C TCC<br>r Ser | SEQ ID NO: 31 |
| Rβ1 | CAC AG<br>His Se | gtgagctgc | ctg cctgcct | gaatctctct cttttt ...tag | C TCC<br>r Ser | SEQ ID NO: 32 |
| Hβ2 | CAG AG<br>Gln Se | gtaagtgtg | cccagcgtttctctttg | ...tag | T GTC<br>r Val | SEQ ID NO: 33 |
| Rβ2 | CAG AG<br>Gln Se | gtaagtgtg | ctttcctcttgtcagggctct | ...tag | T GTC<br>r Val | SEQ ID NO: 34 |
| Hβ3 | CAG AG<br>Gln Se | gtagggtcgcg | ggtgggccggcggcgg | ...cag | T GTG<br>r Val | SEQ ID NO: 35 |
| Rβ3 | CAG AG<br>Gln Se | gtagggtcgct | ggtgggttgactgtgtcgggcg | ...cag | T GTG<br>r Val | SEQ ID NO: 36 |

*FIG. 6*

SEQ ID NO: 37

```
              PCR541              AP1             CACCC
       -436  ACTCTTCCTGC TCCAGT CACCCCCACCCA CAACCCCGC

GRE             Sp1                        HGRE
       -395  TGATC ACATCCTC CCGG TGCCCGCCAC AGGCAACCAG AGAA

AP1
                                                                   AA-
       -354  CA ACAGACCCTCCTCCAGAGTCCCCGTTCTAGGACCTC CT

Control    PCR412/180    CAAT/NFY
       -313  GACT GT CA ACGAAAG ATGCCAATCAC AGGCAGCCTTAGCCA
                                              →5' DEL 1

SRY/HFH2
       -272  GATCACTGAGCGCCAGTA AAAAAAACAAAATC AGGTTGAG

CAAT        NF-κB
       -231  GGCAGAAATGAAATCAACATAGCAACCT CCAAT GCAT GAAG
                                              →5' DEL 2
                                                    →5' DEL 3
                        E box                              Ins Enh
       -190  GAAACTCCG TTTA CACATG CTCGTAGGATCCCCTGC GTGGA
              PCR253 (5' DEL 5)    →5' DEL 4
              AP4           AP1  AA-Control     GRE         Inr
       -149  AACAGCAGCT TGTC T CTGACTA CC G GAGGACATGGAGCAC
                                    PCR180                —Neural Specific—

-108  CCC AAATAGGAACTTTAGAGGGATTGAAATCTGTTGCCTGT

OCT 1      TATA  SRY/Sox5                delta EF1
       -67   TCC ACTAGG AATATTGTTTG CAAGGCA CAAGGTGTCT TTTG
              3' DEL 4←    3' DEL 3←                   Inr
                                                →    CAP/ETS-1  HSF1
       -26   GTAGTGAGCGCGCTCTGCGCATG C GCAGGTC CAT TCGGGAA
                                3' DEL 2←     ◊              ◊
              Inr
                           AP1           Inr          AP1
       16    TTAC TGCCCAGCAGCC GACTAAG TTGCATTCCT TGAATCT T
                                          ◊
              cDNA         DFD    TATA      Inr
                  HSF3        AP1                           Met
       57    CGC AGAAAAGACAA TT CTT TTAATCA GAGT TAGTA ATGTGG
                           3' DEL 1←         *  *    Δ     Δ

98    ACAGTACAAAATCGAGAGAGTCTGGGGCTTCTCTCTTTCCC
                   Δ               Δ    Δ
                   +  PCR541/412/253  +
              Met           Met              Se
       139   TGTGATGATTACCATGGTCTGTTGTGCACACAG /Intron 1
```

FIG. 7

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

ACTAGGAATA TTGTTTG                                          17

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GCGCAGGTCC ATTCGGGAAT                                    20

(2) INFORMATION FOR SEQ ID NO:3:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

AGGAGATGGA GC                                                12

(2) INFORMATION FOR SEQ ID NO:4:

(i) SEQUENCE CHARACTERISTICS:
      (A) LENGTH: 11 base pairs
      (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:4:

TGAATCTCTC T                                                                  11

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTAGGGTCGC KGGTGGG                                                            17

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCATGGTCTG TTGTCCACAG                                                         20

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ACTGTCCACA TTACTAACTC TGAT                                                    24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATAATGGTAC CGGGGGGGGG GGGG                                                    24

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:9:

GGTACCCCGC GGGCTAGCCT CGAGGCCCGG GCCAGCTGTC GCGAA                     45

(2) INFORMATION FOR SEQ ID NO:10:

(i) SEQUENCE CHARACTERISTICS:
             (A) LENGTH: 49 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:10:

CGCGTTCGCG ACAGCTGGCC CGGGCCTCGA GGCTAGCCCG CGGGGTACC                 49

(2) INFORMATION FOR SEQ ID NO:11:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:11:

CGCGTGCGGC CGGAGCTCCC ACCATGGTGG A                                    31

(2) INFORMATION FOR SEQ ID NO:12:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:12:

GATCTCCACC ATGGTGGGAG CTCCCGGCCG CA                                   32

(2) INFORMATION FOR SEQ ID NO:13:

(i) SEQUENCE CHARACTERISTICS:
             (A) LENGTH: 42 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:13:

TCGACCCGCG GCGGCCGTAC GTACACGTGT GATCAACTAG TG                        42

(2) INFORMATION FOR SEQ ID NO:14:

(i) SEQUENCE CHARACTERISTICS:
             (A) LENGTH: 42 base pairs
             (B) TYPE: nucleic acid
             (C) STRANDEDNESS: single
             (D) TOPOLOGY: linear

```
        (ii) MOLECULE TYPE: DNA (genomic)

(xi) SEQUENCE DESCRIPTION: SEQ ID NO:14:

GATCCACTAG TTGATCACAC GTGTACGTAC GGCCGCCGCG GG                            42

(2) INFORMATION FOR SEQ ID NO:15:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:15:

UUAACCAUGG                                                               10

(2) INFORMATION FOR SEQ ID NO:16:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

AGGAGATGGA GC                                                            12

(2) INFORMATION FOR SEQ ID NO:17:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

ACTAGGAATA TTGTTTG                                                       17

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

GCGCAGGTCC ATTCGGGAAT                                                    20

(2) INFORMATION FOR SEQ ID NO:19:

(i) SEQUENCE CHARACTERISTICS:
            (A) LENGTH: 13 base pairs
            (B) TYPE: nucleic acid
            (C) STRANDEDNESS: single
            (D) TOPOLOGY: linear
```

-continued (ii) MOLECULE TYPE: DNA (genomic)

(xi) SEQUENCE DESCRIPTION: SEQ ID NO:19:

GGACATGGAG CAC                                                        13

(2) INFORMATION FOR SEQ ID NO:20:

(i) SEQUENCE CHARACTERISTICS:
        (A) LENGTH: 868 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GACAATTCTT TTAATCAGAG TTAGTAATGT GGACAGTACA AAATCGAGAG AGTCTGGGGC      60

TTCTCTCTTT CCCTGTGATG ATTACCATGG TCTGTTGTGC ACACAGGTGA GCTGCTGTTG     120

TTGAATCTCT CTCTGCTCTC TCTCTTTTTT TCTTGGTATG TTTCTTTTTA CGTGTCTGCT     180

GGATCATGTA TCTTGTTGTT TGGGGGTAGG TGTGCCTGTA TCTTTTTATA TGTGCTCACA     240

GTTTGTGCTC ATTTTGAATA CGGTCCCTAC TTCTTCCCCT TAGCACCAAT GAACCCAGCA     300

ACATGTCATA CGTGAAAGAG ACAGTGGACA GATTGCTCAA AGGATATGAC ATTCGCTTGC     360

GGCCGGACTT CGGACGTAAC GCTTCATCTT TTTTCAACCT GTAACCCATC CTTAAGTTCT     420

CCTTTTCTAT CAAAGATAAA TGTCAAAAAA AAAAAAAAA AAAAAAGGCA TGTCATTTTC      480

GTAAGCGTGC ACTATACCCT GGACACACAC ACACACACAC ACACACACAC ACACACACCA     540

CCCCGGGTCC CCCAGTCTCA GGTTTGGATG AATCCTCAGG CGGAGGGCGA CCTTCTCCCC     600

CCGGGCCGAC ACACCTCTGC ATAGTCACTG CATCACGTGT GTGCCCACAC CTGTTTTCCC     660

AGGCAGTCCC CTGAAAGGGT GGTGGGGGGA GCAGGGAGGG AGCCCGTTAA GAATGGAGTA    720

AGGGCTGGGA AGCCCCCAGA CCCTCCCCAG CCTGCTGTCA CTGAGAGAAT CTGTTCCTAA     780

TGTGGCCCAC CTCCCCGGCA GGGCCCCCGT CGACGTTGGG ATGAGGATCG ATGTCGCCAG     840

CATAGACATG GTCTCCGAAG TGAATATG                                        868

(2) INFORMATION FOR SEQ ID NO:21:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GAAAGACAAT TCTTTCATCA GAGTTAGTAA TGTGGACAGT ACAAAATCGA GA              52

(2) INFORMATION FOR SEQ ID NO:22:

(i) SEQUENCE CHARACTERISTICS:
        (A) LENGTH: 54 base pairs
        (B) TYPE: nucleic acid
        (C) STRANDEDNESS: single
        (D) TOPOLOGY: linear

```
        (ii) MOLECULE TYPE: DNA (genomic)

(xi) SEQUENCE DESCRIPTION: SEQ ID NO:22:

GAAAAGACAA TTCTTTTAAT CAGAGTTAGT AATGTGGACA GTCAAAACGA GAGA           54

(2) INFORMATION FOR SEQ ID NO:23:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

GAGTTTGGGG CTTCTCTCTT TTCCTGTGAT GGTTGCCATG GTTTGTTGTG ACAC           54

(2) INFORMATION FOR SEQ ID NO:24:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:24:

GAGTCTGGGG CTTCTCTCTT TCCCTGTGAT GATTACCAAG GTGTGTTGTG ACAC           54

(2) INFORMATION FOR SEQ ID NO:25:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

AGCTCCAATG AACCCAGCAA CATGTCATAC GTGAAAGAGA CAGTGGACCG ACTG           54

(2) INFORMATION FOR SEQ ID NO:26:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:26:

AGCACCAATG AACCCAGCAA CATGTCATAC GTGAAAGAGA CAGTGGACAG ATTG           54

(2) INFORMATION FOR SEQ ID NO:27:

(i) SEQUENCE CHARACTERISTICS:
            (A) LENGTH: 54 base pairs
            (B) TYPE: nucleic acid
            (C) STRANDEDNESS: single
            (D) TOPOLOGY: linear
```

(ii) MOLECULE TYPE: DNA (genomic)

(xi) SEQUENCE DESCRIPTION: SEQ ID NO:27:

GCTCAAAGGA TATGACATTC GCTTGCGGCC AGACTTTGGA GGGCCCCCGG TGGA          54

(2) INFORMATION FOR SEQ ID NO:28:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GCTCAAAGGA TATGACATTC GCTTGCGGCC GGACTTCGGA GGGCCCCCCG TCGA          54

(2) INFORMATION FOR SEQ ID NO:29:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CGTCGGGATG ACGGATCGAT GTCGCCAGCA TAGACATGGT CTCGGAAGTG AA            52

(2) INFORMATION FOR SEQ ID NO:30:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CGTTGGGATG AGGATCGATG TCGCCAGCAT AGACATGGTC TCCGAAGTGA A             51

(2) INFORMATION FOR SEQ ID NO:31:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CACAGGTGAG CTGCTGTTGT TGAATCTCTC TCTCTCTTAG CTCC                     44

(2) INFORMATION FOR SEQ ID NO:32:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CACAGGTGAG CTGCCTGCCT GCCTGAATCT CTCTCTTTTT TTAGCTCC                  48

(2) INFORMATION FOR SEQ ID NO:33:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

CAGAGGTAAG TGTGCCCAGC GTTTCTCTTT TCGTTCTCAC TTTGTAGTGT C              51

(2) INFORMATION FOR SEQ ID NO:34:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

CAGAGGTAAG TGTCGCTTTC CTTCTCACTT GTCAGGGGCT CTTAGTGTC                 49

(2) INFORMATION FOR SEQ ID NO:35:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

CAGAGGTAGG GTCGCGGGTG GGCCGGCGGC GGCGGCAGTG TG                        42

(2) INFORMATION FOR SEQ ID NO:36:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

CAGAGGTAGG GTCGCTGGTG GGTTGACTGT GTCGGGCGCA GTGTG                     45

(2) INFORMATION FOR SEQ ID NO:37:

(i) SEQUENCE CHARACTERISTICS:
            (A) LENGTH: 607 base pairs
            (B) TYPE: nucleic acid
            (C) STRANDEDNESS: single
            (D) TOPOLOGY: linear -continued (ii) MOLECULE TYPE: DNA (genomic)

(xi) SEQUENCE DESCRIPTION: SEQ ID NO:37:

```
ACTCTTCCCT GCTCCCAGTC ACCCCCACCC ACAACCCCG  CTGATCACAT CCTCCCGGTG      60

CCCGCCACAG GCAACCAGAG AACAACAGAC CCTCCTCCAG AGTCCCCGTT CTAGGACCTC     120

CCTGACTGTC AACGAAAGAT GCCAATCACA GGCAGCCTTA GCCAGATCAC TGAGCGCCCA     180

GTAAAAAAAA CAAAATCAGG TTGAGGGCAG AAATGAAATC AACATAGCAA CCTCCAATGC     240

ATGAAGGAAA CTCCGTTTAC ACATGCTCGT AGGATCCCCT GCGTGGAAAC AGCAGCTTGT     300

CTCTGACTAC CCGGAGGACA TGGAGCACCC CAAATAGGAA CTTTAGAGGG ATTGAAATCT     360

GTTGCCTGTT CCACTAGGAA TATTGTTTGC AAGGCACAAG GTGTCTTTTG GTAGTGAGCG     420

CGCTCTGCGC ATGCGCAGGT CCATTCGGGA ATTACTGCCC AGCAGCCGAC TAAGTTGCAT     480

TCCTTGAATC TTCGCAGAAA AGACAATTCT TTTAATCAGA GTTAGTAATG TGGACAGTAC     540

AAAATCGAGA GAGTCTGGGG CTTCTCTCTT TCCCTGTGAT GATTACCATG GTCTGTTGTG     600

CACACAG                                                              607
```

NEURON-SPECIFIC TRANSCRIPTIONAL PROMOTER

This application is a continuation of International Application PCT/US96/18830, filed Nov. 8, 1996, which claims benefit of U.S. Provisional Application No. 60/006,509, filed Nov. 9, 1995.

The work leading to this invention was supported in part by a Grant from the National Institutes of Health. The U.S. Government retains certain rights in this invention.

BACKGROUND

1. Field of the Invention

This invention is directed toward expression vectors which permit expression of heterologous genes in mammalian tissue, including humans. In particular, this invention provides a DNA sequence which promotes gene expression preferentially in hippocampal tissue.

2. Related Art

A dramatic example of cell specific gene expression is illustrated by the γ-aminobutyric acid type A (GABA$_A$) receptor gene family in the nervous system. A number of the GABA$_A$ receptor genes display preferential expression in only one region of the brain, while expression in other brain regions is barely detectable. In particular, β1 subunit gene expression is highest in the pyramidal neurons of the hippocampus, making it a prime candidate for the study of cell-specific regulation.

Small molecules such as acetylcholine, glutamate, γ-aminobutyric acid (GABA), and glycine serve as the major neurotransmitter that carry signals from the presynaptic nerve terminal to the postsynaptic membrane. Inhibitory neural transmission is a central component of information processing for both vertebrates and invertebrates, and GABA is the major transmitter at inhibitory chemical synapses. Virtually all neurons in the vertebrate nervous system are sensitive to GABA with inhibitory synaptic activity being mediated through the GABA$_A$ receptor.

The GABA$_A$ Receptors

Binding of GABA to its recognition site on the GABA$_A$ receptor opens an integral chloride (Cl$^-$) channel (for review see Stephenson, 1988). This drives the membrane potential towards the Cl$^-$ equilibrium potential, decreasing the likelihood that depolarization by excitatory neurotransmitter will generate action potentials (since the Cl$^-$ equilibrium potential is near the resting membrane potential in most neurons). A variety of clinically significant pharmaceuticals including benzodiazepines (Choi et al., *Nature* 269:342–344 (1977)), barbiturates, ethanol and neuro steroids (steroids that are produced in the nervous system) (Wu et al., *Mol. Pharmacol.* 37:597–602 (1990)), bind to sites on the GABA$_A$ receptor and allosterically potentiate the GABA response.

Chronic exposure to GABA down regulates receptor number and uncouples allosteric interactions between the GABA and $^3$H-flunitrazepam recognition sites (Roca et al., *Mol. Pharmacol.* 37:710–719 (1990)). As described previously for the β2-adrenergic receptor, uncoupling may be a separate form of GABA$_A$ receptor regulation. However, because down-regulation and uncoupling occur on the same time scale, they could involve different manifestations of the same process. Changes in GABA$_A$ receptor gene expression or mRNA stability may be responsible for the down regulation of receptors seen at the cell surface. Uncoupling may also be due to changes in transcriptional activity leading to the expression of GABA$_A$ receptors of altered subunit composition and altered pharmacological properties.

The GABA$_A$ receptor is comprised of several different types of subunits that can be identified by biochemical and molecular biological techniques. Upon SDS-Polyacrylamide Gel Electrophoresis (PAGE), the affinity purified GABA$_A$ receptor can be resolved into two major bands of protein (α, 48–53 kd and β, 55–57 kd) (Stephenson, *Biochem. J.* 249:21–32 (1988)). The β band is preferentially photo affinity labeled by the GABA agonist $^3$H-muscimol (Deng et al., *Biochem. Biophys. Res. Commun.* 138:1308–1314 (1986)) while the α band is preferentially photo affinity labeled by the benzodiazepine positive modulator $^3$H-flunitrazepam (Sigel et al., *J. Biol. Chem.* 258: 6965–6971 (1983); Stauber et al., *Biochem. J* 249: 21–32 (1987); Sweetnam et al., *Mol. Brain Res.* 2:223–233 (1987)). Molecular biological studies have revealed that there are many more subunits and subunit variants than originally seen on SDS gels. In fact, the cDNAs for a large number of GABA$_A$ receptor subunits and subunit subtypes ($α_{1-6}$, $β_{1-4}$, $γ_{1-3}$, δ, and $ρ_{1-2}$) have been isolated and are each thought to be encoded by a different gene.

The cDNA for a putative GABA$_A$ receptor subunit in the fresh-water mollusc *Lymnaea stagnalis* has recently been cloned, and coexpression of the Lymnaea β1 subunit with the bovine α subunit produces a functionally hybrid GABA$_A$ receptor in *Xenopus* oocytes (Harvey et al., *EMBO J.* 10:3239–3245 (1991)). The observation that GABA$_A$ receptor subunits derived from the invertebrate and vertebrate genomes can successfully co-assemble suggests that GABA$_A$ receptor function has been a common theme in the evolution of the nervous system.

Studies in recombinant systems have shown that expression of at least three different subunit genes (α, β and γ) is necessary for the production of a pharmacologically functional GABA$_A$ receptor: a GABA gated Cl$^-$ channel with activity that is potentiated by benzodiazepines or barbiturates (Schofield et al., *Nature* 328:221–227 (1987); Pritchett et al., *Science* 245:1389–1392 (1989a)). The combination of expressed subunits affects the affinity of the receptor for GABA. The rank order of potencies of the recombinant GABA$_A$ receptors is α5β1>>α1β1, α3β1, or α5β1γ2>α1β1γ2. The presence of the β1 subunit in the expressed recombinant receptor produces a dramatic decrease in the EC$_{50}$ for the GABA response. Therefore GABA$_A$ receptors comprised of α1β1γ2 subunits exhibit increased responsiveness to subsaturating concentrations of GABA and decreased enhancement by diazepam relative to receptors comprised of α1β2γ2 subunits.

Interestingly, the β1, α2, and γ1 genes, which are all highly expressed in the hippocampus, are thought to be adjacent to one another on chromosome 4. The co-localization of the genes coding for the α and β and/or γ subunits may reflect coordinate regulation of receptor subunit genes that share a tissue-specific expression in the CNS.

The pharmacological distinctions between different expressed recombinant GABA$_A$ receptors and the subunit composition of individual cells in the CNS remains to be elucidated. Important new information has been provided by Persohn and colleagues who reported that certain neurons in the rat CNS express unique combinations of GABA$_A$ receptor subunits (Persohn et al., *J. Comp Neur.* 326:193–216 (1992)). Regional and developmental specific expression of GABA$_A$ receptor mRNAs (Wisden et al., *J Neurosci.* 12:1040–1062 (1992); Laurie et al., *J Neurosic.* 12(11):

4151–4172 (1992)) has also revealed the potential for pharmacologically distinct isoforms of the $GABA_A$ receptor.

Control of Gene Expression

While little is known about the promoters that control the expression of $GABA_A$ receptor subunit genes, much has been learned about the promoters that drive the expression of other genes. An 86 bp sequence in the 5' flanking region of the mouse α1 acetylcholine receptor subunit gene in chicken and mouse also contains TATA and CAAT boxes, previously found to be necessary for transcriptional control in many eukaryotic genes (Klarsfeld et al., Neuron 2:1229–1236 (1989); Prody and Merlie, J. Biol Chem. 266(33):22588–22596 (1991)). The presence of TATA and CAAT boxes in the promoter region of a gene is not always necessary for the activation of transcription. The 5' flanking regions of the human dopamine D1A and D2 receptor genes lack the canonical TATA and CAAT boxes but are rich in G+C content and contain the recognition sequences for other regulatory elements, such as SP1 and AP1, that are required for activation (Minowa et al., 1992; Minowa, Minowa, and Mouradian, 1992). The regulation of opioid gene expression, in particular the proenkephalin gene, has also been linked to the presence of c-AMP response element (CRE) and CRE-2 sequences (Hyman et al., 1983). The c-AMP binding protein (CREB) and the AP1 transcription factor complex (c-Fos, c-Jun, and other immediate early genes) have been found to bind to the CRE and CRE-2 of the proenkephalin gene.

Other regions of a gene locus can play an important role in regulation, making it even more difficult to model the regulation of transcription in vivo. For example, an enhancer element found in the 3' flanking region more than 24 kb away from the transcriptional start site drives the embryonic expression of the myosin light chain gene in skeletal muscle (Rosenthal et al., Proc. Natl. Acad. Sci. 86:7780–7784 (1989)). The first intron of a gene can also contain regulatory elements that are critical for promotor activity. For instance, the first intron of the human growth hormone gene contains a glucocorticoid-responsive element that is induced by dexamethasone (Slater et al., Mol. Cell. Biol. 5:2984–2992 (1985)). The first intron of the mouse $α_1$ (type I) collagen gene (Horton et al., Proc. Nail. Acad. Sci U.S.A. 84:8864–8868 (1987)), also contains cell-specific enhancers of transcription. In contrast, the first intron of the rat type II sodium channel and the rat brain-derived neurotrophic factor genes contain a neural-restrictive silencer (Timmusk et al., Neuron 10:475–489 (1993)); a factor that is present in nonneuronal but not in neuronal cells binds to a sequence within this silencer consistent with suppression of transcription in nonneuronal cells. An evolutionarily conserved enhancer element has also been identified in the first intron of the human and rat β-actin genes and is required for gene activation (Ng et al., Nature London 314:183–184 (1985); Kawamoto et al., Mol. Cell. Biol. 8:267–272 (1988); Frederickson et al., Nucl. Acids Res. 17:253–270 (1989)).

The most compelling evidence for the importance of introns to gene regulation comes from experiments using transgenic mice. Transgenes that contain cDNA sequence downstream of a related promoter can fail to give tissue specific expression in transgenic animals although being sufficient for expression in established and transformed cell lines. It has recently been demonstrated that introns specific to the expressed gene increase transcription 10 to 100 fold in transgenic mice (Brinster et al., Proc. Natl. Acad. Sci. U.S.A. 85:836–840 (1988). It is believed that introns may contain important regulatory elements that are active during development but that are no longer necessary after transfection into an established or transformed cell line. Therefore, the best way to evaluate the regulatory role of the intron may be in transgenic animals and in cells derived from intact tissue and maintained in primary cell culture.

SUMMARY OF THE INVENTION

This invention provides an isolated DNA molecule comprising a neuron-specific transcriptional promoter, which is more transcriptionally active in hippocampal cells than in neocortical cells. In one embodiment, the neuron-specific promoter comprises a transcription initiation site and a binding site for an octamer binding protein (e.g. Oct-1), which may be the sequence element 5'-ACTAGGAATATTGTTTG-3' SEQ ID NO:1, positioned at least 35 nucleotide base pairs (bp) upstream from the transcription initiation site. In a preferred embodiment, the transcription initiation site comprises sequence element 5'-GCGCAGGTCCATTCGGGAAT-3' SEQ ID NO:2.

In another embodiment, this invention provides an isolated DNA molecule comprising a neuron-specific transcriptional promoter, which is more transcriptionally active in hippocampal cells than in neocortical cells, the neuron-specific promoter comprising a transcription initiation site and a binding site for the octamer binding protein, and further comprising a cis-acting element upstream from the promoter, which confers orientation specificity on the transcriptional activity of the promoter. Preferably, the cis-acting element comprises at least 4 sequential nucleotides found in the enhancer segment upstream of the promoter for the $GABA_A$ β-1 receptor subunit (sequence positions from position –174 to position –150 of FIG. 7), e.g., one CAAT box or two CAAT boxes separately placed in the segment, or the entire segment.

In another embodiment, this invention provides an isolated DNA molecule comprising a neuron-specific transcriptional promoter, which is more transcriptionally active in hippocampal cells than in neocortical cells, the neuron-specific promoter being down-regulated by γ-aminobutyric acid or ethanol, or regulated by steroids, such as glucocorticoid or neurosteroids.

In another embodiment, this invention provides an isolated DNA molecule comprising a neuron-specific transcriptional promoter, which is more transcriptionally active in hippocampal cells than in neocortical cells, the neuron-specific promoter comprising a transcription initiation site and a binding site for the octamer binding protein, and further comprising an open reading frame comprising at least one exon of a protein coding sequence which is transcribed under control of the promoter; and a negative regulatory sequence element downstream from the promoter, the negative regulatory sequence element comprising all or a portion of the first intron of the β-1 subunit gene of $GABA_A$ receptor. Preferably, the negative regulatory sequence element is part of an intron downstream from the at least one exon in the open reading frame. In a particular embodiment, the negative regulatory sequence element has transcriptional promoter activity for transcription in opposite orientation from RNA transcribed under control of the promoter, the transcriptional promoter activity of the negative regulatory sequence element preferably being greater in neocortical cells than in hippocampal cells.

In yet another embodiment, this invention provides a method of screening a compound for pharmacological activity comprising culturing a cell transfected with a DNA molecule comprising a neuron-specific transcriptional promoter, which is more transcriptionally active in hippocampal cells than in neocortical cells, the neuron-specific promoter comprising a transcription initiation site and a binding site for the octamer binding protein, and further comprising a protein coding sequence comprising at least one exon of a protein coding sequence which is transcribed under control of the promoter, and determining expression of the protein coding sequence in the presence and absence of the compound.

In still another embodiment, this invention provides a DNA molecule comprising a first transcriptional promoter, at least one exon of a protein coding sequence which is transcribed under control of the first transcriptional promoter, and a second transcriptional promoter downstream from the transcription initiation site of the first promoter, wherein RNA transcribed from the second promoter contains at least a portion which is complementary to RNA transcribed from the first promoter, and further wherein at least one of the first promoter and the second promoter does not control transcription of all or a portion of the protein coding sequence or its complement in the genome of any organism in nature. In a particular embodiment, activity of one or more of the first and the second promoters are regulated by extrinsic agents, i.e., extracellular molecules such as hormones, drugs or other smal molecules. In a preferred embodiment, the second promoter is part of an intron downstream from the first exon in the protein coding sequence.

The β1 promoter construct described within is sufficient to drive neuron specific gene expression in primary brain cultures. The addition of a negative regulatory element found within the first intron of the β1 gene targets gene expression to hippocampal neurons by repressing activity in non-hippocampal cells. The addition of the first intron of the β1 subunit gene of the $GABA_A$ receptor to the reporter construct containing the β1 promoter targets gene expression to hippocampal neurons by repressing activity in non-hippocampal cells. The mechanism behind such gene targeting appears to be the addition of a negative regulatory element found within the first intron. Alternatively, expression may be limited to hippocampal tissue by production of antisense transcripts complementary to the primary transcript driven by an antisense promoter present within the intronic sequence.

PCR genomic walking techniques were used to isolate a 496 bp region upstream to the published 5' end of the "full length" human β1 cDNA. Mapping of transcriptional start sites and transfection into primary cell cultures of embryonic chick brain, rat neocortex, and rat hippocampus demonstrated that there is a functional promoter within the first 148 bp of 5' flanking region and stimulatory sequences within the next upstream 159 bp. The presence of important regulatory sequences necessary for promoter activity was revealed by a set of internal deletions that implicate the CAAT box (at −199 to −203, FIG. 7), the octamer (at −64 to −48) and the major transcriptional initiation site (at −3 to +19). Inclusion of the first intron in the DNA construct inhibits promoter activity in neocortical and non-neuronal cultures while activity is not inhibited in the hippocampus. This is consistent with the presence of a repressor in the β1 gene. Furthermore, promoter activity is neural specific and subject to autologous negative regulation through the $GABA_A$ receptor, downregulation by (ethanol, and positive regulation thought the steroid hormone receptor.

BRIEF DESCRIPTION OF THE FIGURES

FIG. 2 is a representation of the original promoter cloning region located at the 5'-end of the pGL2-Basic and pGL2-Enhancer vectors (top horizontal line) and its replacement with the re-designed multiple cloning region (bold horizontal line below). An insert was added by directional cloning between the SmaI and Bgl II sites. The asterisk (*) represents the loss of the Sma I site in the original vector upon ligation of the insert. Sites for restriction enzymes that produce blunt ends are indicated above each of the horizontal lines while sites that produce cohesive ends are indicated below the lines. FIG. 3 is a representation of the original enhancer cloning region found at the 3'-end of the luciferase gene in both the pGL2-Basic and pGL2-Promoter vectors (top horizontal line) and its replacement with the modified multiple cloning region (bold horizontal line below). Restriction sites are indicated as described above.

FIG. 4 shows partial sequence obtained by PCR amplification of the first three exons of the human β1 subunit gene. The partial nucleotide sequence of three exons (uppercase letters) and two introns (lowercase letters) is shown. This entire sequence is designated SEQ ID NO: 20. The presumed first intron interrupts the condon for serine, which is the second amino acid of the mature polypeptide chain. Consensus sequences for a CAAT box, TATA box, and a TRN INIT site which are found within the first intron are indicated by boxes. Flanking PCR primers are represented by dashed lines. Numbers over the coding sequence of the gene refer to the corresponding nucleotide position in the Garrett Hβ1 cDNA with reference to the expected translational start site at +1.

FIG. 5 shows comparison of exonic sequence for the human and rat β1 $GABA_A$ receptor genes. The nucleotide sequence contained within the first three exons of the rat β1 and human β1 genes were aligned for comparison and gaps (−) were added to maximize regions of homology. Conserved nucleotides are indicated by vertical bars. Coincidence of intron 1 and intron 2 position in the rat and human genes is indicated by the diamond (◊).

FIG. 6 compares consensus sequences at the 5' donor and 3' acceptor sites of intron 1 for the β1, β2, and β3 genes in human and rat. An "H" or an "R" before the name of the β gene indicates the species of origin, human or rat respectively. The sequence of exons is represented by plain uppercase letters. The sequence of introns is represented by plain lowercase letters. Conservation of sequence is represented by vertical bars. The three letter amino acid code is represented under the nucleotides of the coding region which flank intron 1. Gaps have been added for the sake of presentation.

FIG. 7 shows the nucleotide sequence for the 5' end of exon 1 and the 5' flanking region of the human β1 gene obtained from amplified gene segment PCR541. This entire sequence is designated SEQ ID NO: 37. Only the + strand is shown. Transciptional initiation sites were mapped by a number of different techniques and are shown by symbols under the corresponding nucleotides. Results of S1 nuclease protection are indicated by (+), primer extension by (*), and modified SLIC by (Δ) and (◊). To provide a single base for numbering purposes, the first nucleotide, A, of the most 5' transcriptional initiation site is designated as +1 and shown by an overlining rightward arrow. 436 bp of putative flanking sequences is indicated by negative numbers. The 5' end of the "full length" human β1 cDNA is shown by a bracket at +53. Half brackets mark the positions corresponding to the 5' and 3' ends of PCR541, 253, and 180. PCR412 extends from the 3' end of PCR541 to the 5' end of PCR180. The beginning of the presumed signal peptide is indicated by a Met above the corresponding condon that is underlined. Additional translational start codons are also represented. The position of the presumed first intron is indicated by a slash mark within the sequence. Consensus sequences for regulatory elements and transcriptional initiation sites are enclosed in boxes. The orientation of each presumed TATA box is indicated by an underlining arrow. Similarity to a possible neural specific sequence found in the 5' flanking region of the rat GAP-43 and type II Na$^+$ channel genes is indicated by a bold line originating at −122. A CRE-like element (−306 to −314) that is interrupted by a T (TGAC-T-GTCA) is underlined.

FIG. 9B shows the data from primary cultures of chick brain which were transfected with either pGLef-541 or pGLef-541SvE. +SvE indicates the presence of the Sv40 enhancer. FIG. 9C shows data from primary cultures of rat neocortex which were transfected with either pGL-Sv40 or GL-Sv40SvE, and FIG. 9D shows data from primary cultures of rat neocortex which were transfected with either pGLef-541 or pGLef-541SvE.

DETAILED DESCRIPTION OF THE INVENTION

Figure 1:
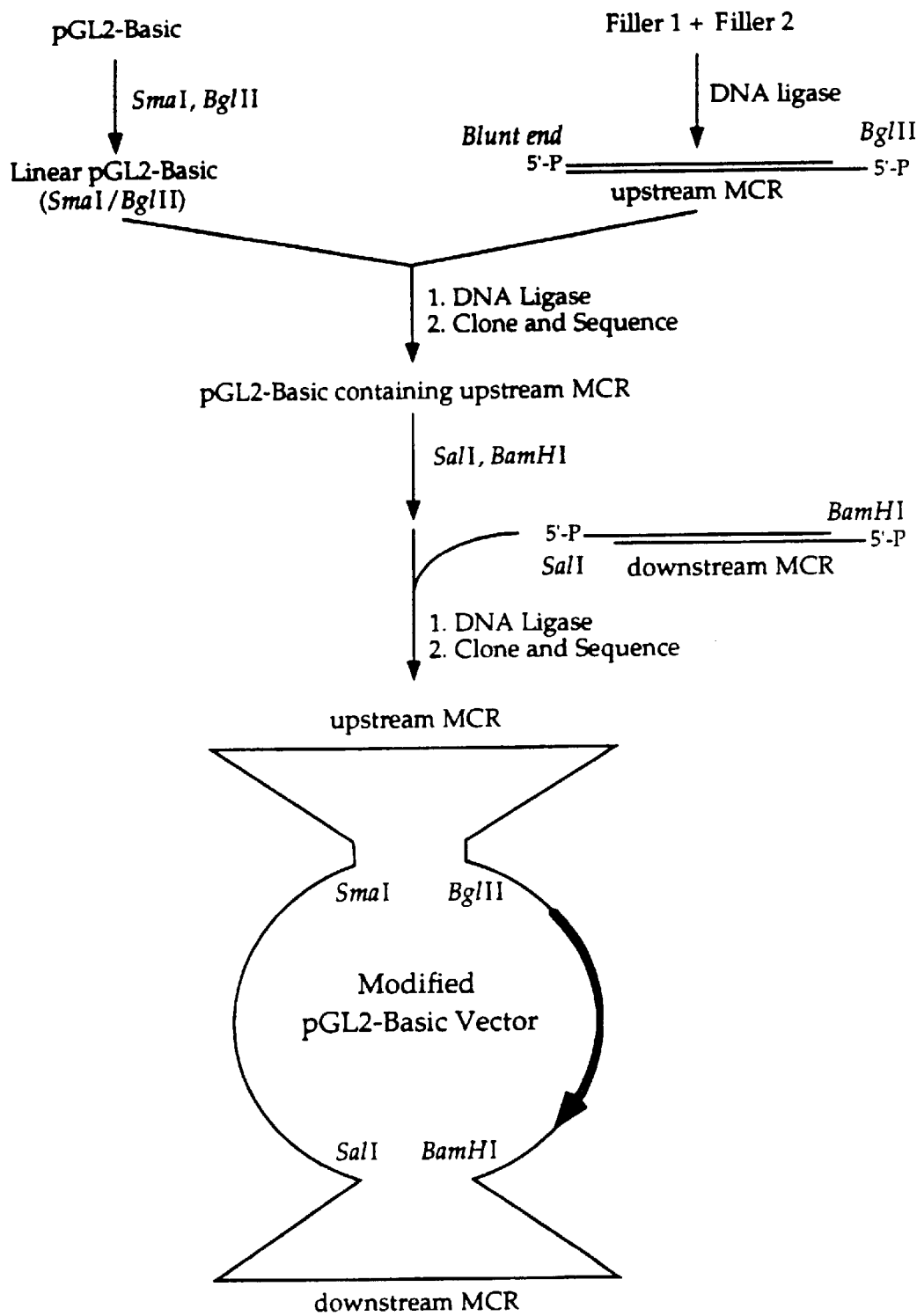
FIG. 1 shows construction of a modified pGL2-Basic vector for use with restriction selection cloning. The pGL2-Basic vector was modified to contain two new multiple cloning regions (MCRs). The MCRs were produced by the ligation of double stranded oligonucleotides to complementary sites in the pGL2-Basic vector (see text). The black arrow on the modified pGL2-Basic vector map indicates the position of the firefly luciferase gene in reference to the position of the MCRs. The upstream MCR, located 5' to the luciferase gene, is used to test DNA fragments for promoter activity while the downstream MCR, located 3' to the luciferase gene, is used to test DNA fragments for enhancer or repressor activity.

Understanding the factors that control the levels of GABA$_A$ receptor subunit transcripts is particularly important because it has been demonstrated that different GABA$_A$R subunits may assemble into region-specific isoforms (Sigel et al., *FEBS Lett*. 2:377–379 (1989)), providing the molecular basis for the functional diversity of GABA$_A$ receptors that is observed in the central nervous system (Rabow et al., 1995). The cDNAs for a large number of GABA$_A$R subunits and subunit subtypes ($\alpha_{1-6}$, $\beta_{1-4}$, $\gamma_{1-3}$, δ, and $\rho_{1-2}$) have been isolated and are each thought to be encoded by a different gene that displays region- and developmental-specific expression (Laurie et al., 1992). In particular, the transcript for the β1 subunit is greatest in the adult hippocampal formation, a region of the brain that is believed to play a major role in short term memory processes.

The β1 subunit gene typifies the tissue specific expression of GABA$_A$ receptors in the CNS, because of its differential expression in the hippocampus. A region of the β1 gene has been discovered which contains a tissue specific promoter and enhancer. Chronic drug treatment experiments have also shown that the activity of the promoter is subject to autologous regulation. This observation indicates that activation of GABA$_A$ receptors can modulate gene expression. Furthermore, β1 promoter activity in hippocampal cultures can be stimulated by dexamethasone, which is significant, since stress and aging may produce marked changes in the number and kind of intracellular steroid receptors (Nichols et al., 1990; Spencer et al., 1991; Maccari et al., 1992; Yau et al., 1992). Downregulation of promoter activity can also be produced by ethanol, suggesting that ethanol acting at the GABA$_A$ receptor may autologously regulate the number to transcripts that code for GABA$_A$ receptor subunits, a phenomenon that could contribute to the development of tolerance and to the maintenance of substance abuse.

General Methods

The practice of the present invention employs, unless otherwise indicated, conventional molecular biology, microbiology, and recombinant DNA techniques within the skill of the art. Such techniques are well known to the skilled worker and are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait. ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989).

Definitions

In describing the present invention, the following terminology is used in accordance with the definitions set out below.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed stand of DNA (i.e., the strand having a sequence homologous to the mRNA).

"Amplification" of nucleic acid sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291–294).

Two DNA sequences are "substantially similar" when at least about 85% (preferably at least about 90%, and most preferably at least about 95%) of the nucleotides match over the defined length of the DNA sequences. Sequences that are substantially similar can be identified in a Southern hybridization experiment under, for example, stringent conditions as defined for that particular system. Defining appropriate hybridization conditions is within the skill of the art. See e.g., Maniatis et al., supra; DNA Cloning, vols. I and II supra; Nucleic Acid Hybridization, supra.

A cell has been "transfected" by exogenous DNA when such exogenous DNA has been introduced inside the cell wall.

A "clone" is a population of cells derived from a single cell or common ancestor by mitosis.

A "cell line" is a clone of a primary cell that is capable of stable growth in vitro for many generations.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally occurring mutational events do not give rise to a heterologous region of DNA as defined herein.

An alternative term for heterologous DNA is "recombinant DNA" in recognition of the use of recombinant DNA methodology (see below) to produce a DNA molecule in which a segment from one organism or genome is inserted next to a segment from another genome to artificiality produce a DNA molecule that does not exist in nature. A DNA molecule produced by de novo synthesis of the same DNA sequence as a recombinant DNA molecule would also be considered recombinant DNA. An example of heterologous DNA is a sequence encoding a protein where the sequence is under control of a promoter, where the promoter and the sequence encoding the protein are not from the same genome, or the promoter does not control transcription of the protein in the genome of the organism in which the protein is found in nature.

A "coding sequence" is an in-frame sequence of codons that (in view of the genetic code) correspond to or encode a protein or peptide sequence. A coding sequence in association with appropriate regulatory sequences may be transcribed and translated into a polypeptide in vivo. A polyadenylation signal and transcription termination sequence will usually be located 3' to the coding sequence (downstream) An "exon" is the sequence in a gene that is transcribed and found in the mature transcript, the mRNA. An exon may or may not contain coding sequence.

An "intron" is the sequence in the gene that lies between exons. Intronic sequence is transcribed but subsequently removed from the mature transcript by RNA splicing.

A "promoter" or "transcriptional promoter" is a DNA regulatory region capable of binding RNA polymerase in a cell and initiating transcription of downstream (3' direction) DNA which may include a coding sequence in one or more exons. A promoter "controls" a coding sequence when RNA polymerase which binds the promoter sequence will transcribe the coding sequence into nascent RNA which can then be processed to mRNA and in turn be translated into the protein encoded by the coding sequence.

For purposes of defining the present invention, the promoter sequence includes the minimum number of bases or elements necessary to initiate transcription at levels detectable above background. Within the promoter sequence will be found a transcription initiation site (conveniently defined by mapping with nuclease S1, RNase protection, and/or SLIC PCR), as well as protein binding domains (consensus sequences) responsible for the binding of RNA polymerase. Eucaryotic promoters will often, but not always, contain "TATA" boxes and/or "CAAT" boxes.

This defines a "core promoter" which contains all of the sequence elements necessary for transcriptional initiation to generate transcripts at a level above background. However, useful levels of transcription generally require the presence in the promoter construct of cis-acting elements that enhance the transcription activity. A "minimal promoter" as contemplated by this invention is a promoter construct which exhibits tissue, selectivity, usually through the presence of cis-acting elements which enhance transcription when the construct is transfected into cells of one tissue or inhibit transcription in cells of another tissue. An example of a tissue specific promoter is the β-1 promoter, or one or another of the tissue specific deletion constructs described in Example 4.

A "cis-acting element" describes a sequence that regulates the activity of other DNA sequences on the same DNA molecule. Cis-acting elements may enhance or repress transcriptional activity, i.e., they may be transcriptional stimulatory elements or negative regulatory elements (called enhancers and silencers, respectively). Usually enhancers and silencers affect transcription in either direction along the DNA molecule. However, in a preferred mode of this invention, both transcriptional stimulatory elements and negative regulatory elements are orientation specific. Orientation specific transcriptional stimulatory elements, when associated with a core promoter, will cause the core promoter to initiate transcription only in one direction along the DNA. Orientation specific negative regulatory elements will generally suppress transcription from the promoter in the direction of the negative regulatory element (i.e., the negative regulatory element will only act when positioned downstream from the promoter).

Vectors are used to introduce a foreign substance, such as DNA, RNA or protein, into an organism. Typical vectors include recombinant viruses (for DNA) and liposomes (for protein). A "DNA vector" is a replicon, such as plasmid, phage or cosmid, to which another DNA segment may be attached so as to bring about the replication of the attached segment.

An "expression vector" is a DNA vector which contains regulatory sequences which will direct protein synthesis by an appropriate host cell. This usually means a promoter to bind RNA polymerase and initiate transcription of mRNA, as well as ribosome binding sites and initiation signals to direct translation of the mRNA into a polypeptide. Incorporation of a heterologous DNA sequence into an expression vector at the proper site and in correct reading frame, followed by transformation of an appropriate host cell by the vector, enables the production of a protein encoded by said DNA sequence.

An expression vector may alternatively contain an antisense sequence, where a small DNA fragment, corresponding to all or part of an mRNA sequence, is inserted in opposite orientation into the vector after a promoter. As a result, the inserted DNA will be transcribed to produce an RNA which is complementary to and capable of binding or hybridizing to the mRNA. Upon binding to the mRNA, translation of the mRNA is prevented, and consequently the protein coded for by the mRNA is not produced. Production and use of antisense expression vectors is described in more detail in U.S. Pat. No. 5,107,065 (describing and exemplifying antisense regulation of genes in plants) and U.S. Pat. No. 5,190,931 (describing antisense regulation of genes in both prokaryotes and eukaryotes and exemplifying prokaryotes), both of which are incorporated herein by reference. Additionally, an expression vector may contain more than one means of regulating the expression of a target protein. For instance, regulatory sequences upstream of the transcriptional initiation site may promote protein synthesis while regulatory sequences downstream of the initiation site may inhibit protein synthesis, e.g., by producing antisense transcripts that interfere with translation.

Tissue Specific Expression Vectors

This invention provides expression vectors which control expression of heterologous sequences, directing expression to particular tissues. A vector according to this invention will contain a promoter which promotes expression in cells of vertebrate animals, particularly mammals. The vector may contain a coding sequence under the control of the promoter, or it may contain a cloning site, usually a multiple cloning site, positioned so that a coding sequence inserted at the cloning site will be expressed under control of the promoter. Preferably, the vector will contain additional sequence segments (identified herein as "supplemental control segments" or "cis-acting elements") that enhance expression in desired tissues and/or suppress expression in other tissues. In particular, this invention provides supplemental control segments that enhance expression in neuronal tissues and more preferably supplemental control segments that suppress expression in tissues other than hippocampal tissues.

Vectors in which such supplemental control sequences function can direct tissue-specific expression of reporter proteins, which is useful in studies of embryonic development and in studies of cellular control mechanisms at the transcriptional level. Such vectors are also valuable in gene therapy for directing expression of exogenous genes in desired tissue while avoiding unwanted expression in other tissues. In particular, the supplemental control segments provided herein, in conjunction with suitable promoters, such as the promoter sequences disclosed below, will direct selective expression of exogenous sequences in hippocampal tissues. These vectors are particularly useful for research, including studies concerned with short term memory, and for therapeutic application related to diseases involving hippocampal associated functions, such as Alzheimer's disease and epilepsy.

Supplemental control segments that enhance expression in neuronal tissues and especially supplemental control segments that suppress expression in tissues other than hippocampal tissues may have particular sequences disclosed below and summarized in Table 1. Supplemental control segments according to this invention also include DNA segments with sequences modified to include portions of the sequences disclosed below in conjunction with other sequences, so long as the modified segments retain the function of the segments as disclosed herein. The properties associated with these sequences are summarized in Table 2. In general, the length of the modified segments is similar to that of the segments disclosed below.

A tissue specific expression vector according to this invention may be viewed structurally as a one-dimensional surface which may be conveniently described in relation to the location of the promoter. Preferably, the promoter according to this invention directs transcription in one direction. Therefore, direction on the vector's one-dimensional surface can be conveniently described relative to the direction of transcription under control of the promoter, i.e., "downstream" in the direction of transcription and "upstream" in the direction opposite to transcription.

Promoters according to this invention are a contiguous DNA segment comprising a transcription initiation site and one or more protein binding sites in functional relationship thereto. The protein binding sites may include sequences specific for particular transcription factors and other tissue-specific proteins. In particular the protein binding sites may include one or more of the sites found in the 5' region flanking the β1 gene (FIG. 7). Preferably, the sequences representing protein binding sites will be in the same order (upstream to downstream) as the sites appear in the β1 receptor subunit gene (see Table 1 and FIG. 7). More preferably, separation between any pair of sites (measured in bp) will be approximately the same (e.g., ±15%) as the separation between the two sites in the β1 gene (see FIG. 7). Promoters according to this invention may additionally be accompanied by one or more cis-acting elements. In one embodiment, promoters according to this invention comprise a binding site for octamer-binding proteins, especially Oct-1 (Korner, et al. 1989, *Neuron,* 3:563–572; Bendall, et al. 1993, *Eur. J. Biochem.,* 217:799–811; Lakin, et al. 1995, *Brain Res. Mol. Brain Res.,* 28:47–54).

The promoter comprises a binding site for RNA polymerase and a transcriptional initiation site. The RNA polymerase binding site is usually near the transcriptional initiation site, which is usually an adenosine residue. In a preferred embodiment, the promoter corresponds to the β1 promoter sequence or a modified sequence thereof. The transcriptional initiation site is usually some distance upstream of a translation initiator codon at which translation of the transcribed RNA will begin. The vector according to this invention may have a complete coding sequence, with or without introns, after the translation initiator codon or it may have a cloning site, more preferably a multiple cloning site. Heterologous DNA sequences containing coding sequences may be inserted at the cloning site, and RNA containing the coding sequence will be expressed under control of the promoter. So long as the heterologous DNA is inserted in frame with the translator initiator codon, RNA expressed from the vector can be translated into the protein encoded by the heterologous coding sequence. In-frame insertion is within the skill of the art (see, e.g., Maniatis, et al.).

Supplemental control sequences may be inserted in the vector either upstream or downstream from the promoter. Supplemental control segments include enhancers, which enhance the promotional activity of the promoter, and silencers, which suppress or inhibit transcription. The vector will usually include at least one enhancer, since most promoters demonstrate minimal activity in the absence of an enhancer. Preferably, the vector will contain enhancers and silencers which direct expression if the vector is transfected into the desired tissue and inhibit expression when the vector is transfected into other tissue. Supplemental control segments may also take the form of additional promoters that are inserted downstream of the transciptional initiation site such that they direct the formation of antisense transcripts which interfere with protein (expression.

Where the promoter corresponds to 148 bp immediately upstream from the β1 translational start site, or a modified segment thereof, promotional activity may be undetectable in the absence of an enhancer. In a preferred embodiment, the vector contains an enhancer corresponding to 159 bp upstream from the β1 promoter or a modified segment thereof, and the enhancer may be upstream or downstream from the promoter. In this embodiment, expression is selectively enhanced in neural tissue.

In a particularly preferred embodiment, the vector contains a negative regulatory element which corresponds to the first intron of the β1 gene or a modified segment thereof, and expression is suppressed unless the vector is transfected into hippocampal tissue. Preferably, a negative regulatory element (silencer) corresponding to the first intron or a modified segment thereof will be positioned downstream from the promoter, and preferably downstream from the translational initiator codon. More preferably, this sequence will be present in reverse orientation. Such a silencer element may be present in a intron in the coding sequence, e.g., in the intron that separates the first and second exons of the mature mRNA resulting from transcription initiated by the promoter of this invention.

Producing Tissue Specific Vectors

DNA segments or oligonucleotides having specific sequences can be synthesized chemically or isolated by one of several approaches. The basic strategies for identifying, amplifying and isolating desired DNA sequences as well as assembling them into larger DNA molecules containing the desired sequence domains in the desired order, are well known to those of ordinary skill in the art. See, e.g., Sambrook, et al., (1989); B. Perbal, (1984). Preferably, DNA segments corresponding to all or a portion of the nucleic acid regions and structures of this invention may be isolated individually using the polymerase chain reaction with primers based on the sequences disclosed herein (See methods in M. A. Innis, et al., "PCR Protocols: A Guide To Methods and Applications," Academic Press, 1990).

The sequences according to this invention can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Procedures for construction and expression of mutant proteins of defined sequence are well known in the art. A DNA sequence containing a modified sequence substantially similar to a sequence disclosed herein and capable of similar function can be synthesized chemically or prepared from naturally occurring genomic DNA sequences by one of several approaches, including primer extension, linker insertion and PCR (see, e.g., Sambrook, et al.). It is preferable to test the modified sequences to confirm that they retain the desired functional properties by the assays described below. Testing may be accomplished by placing the coding sequence for a reporter polypeptide in a vector under the control of a promoter/enhancer containing the modified sequence, and transforming host cells with this (expression) vector. The reporter polypeptide may be produced by growing host cells transfected by the expression vector containing the modified sequence under conditions whereby the polypeptide is expressed. The transfected cells are cultured, and monitored to determine whether the vector containing the modified DNA sequence is transcribed into RNA and translated into protein by the host cell transformed by this (expression) vector. Appropriate reporter polypeptides include luciferase, β-galactosidase, and the like, and selection of the appropriate growth conditions is within the skill of the art.

Gene therapy vectors for use in the method of this invention include retroviral or episomal vectors expressing particular desired genes under the control of the promoter and/or the supplemental control sequences disclosed herein (see, e.g., Axel, et al., U.S. Pat. No. 4,399,216, and Pastan, et al., U.S. Pat. No. 5,166,059, both incorporated herein by reference). Delivery systems as contemplated herein include both viral and liposomal delivery systems (see, e.g., Davis, et al., U.S. Pat. No. 4,920,209, incorporated herein by reference). An expression vector for gene therapy can be prepared according to well known principles, and the use of such vectors in treatment of diseases involving the hippocampus, such as Alzheimer's disease and seizure disorders, is within the contemplation of this invention.

Studies of developmental gene expression are preferably performed in transgenic animals. To introduce large genomic regions into mice, investigators have previously used several technologies involving pronuclear microinjection of: microdissected chromosomes (Richa and Lo, 1989, *Science,* 245:175–177), overlapping genomic fragments of the human serum albumin gene that were subsequently recombined in vivo (Pieper, et al., 1992, *Nucl. Acid. Res.,* 20:1259–1264), a 70 kb β globin transgene generated by the in vitro ligation of two 35 kb cosmids, and a 35 kb yeast artificial chromosome (YAC) containing the tyrosinase gene (Schedl, et al., 1992, *Nucl. Acid. Res.,* 20:3073–3077). To transfer YACs into mammalian tissue culture cells, previous investigators have utilized a variety of techniques, including spheroplast fusion (Pachnis, et al., 1990, *Proc. Natl. Acad. Sci. U.S.A.,* 87:5109–5113; Pavan, et al., 1990, *Mol. Cell. Biol.,* 10:4163–4169; Huxley, et al., 1991, *Genomics,* 9:742–750), lipofection (Gnirke, et al., 1991, *EMBO,* 10:1629–1634), calcium phosphate transfection (Eliceiri, et al., 1991, *Proc. Natl. Acad. Sci. U.S.A.,* 88:2179–2183), and electroporation (Fernandex-Luna, et al., 1991, *Genomics,* 10:756–764). Substantial portions of the yeast genome were also transferred (Pavan, et al., 1990, Gnirke, et al., 1991, and Huxley, et al., 1991). These methods may be adequate for introduction of YACs into somatic cells, although transfer of an entire yeast chromosome may be undesirable for propagation through the mammalian germline. Strauss and Jaenisch (1992), *EMBO J.,* 11:417–422, have gel-purified an 1:50 kb YAC containing the 24 kb *Mus. spretus Col1a1* gene and introduced it into mouse fibroblasts by lipofection. Using the methods described in the above references, a vector according to this invention, in which a reporter gene is under the control of the promoter and supplemental control sequences described herein, can be introduced into the genome of a transgenic animal. Expression of the reporter gene can be correlated with developmental stage in the resultant transgenic animals.

Upstream Regulatory Sequences of the GABA$_A$ Receptor β1 Subunit

The GABA$_A$ receptor β1 subunit displays a unique developmental and tissue specific expression (Wisden et al., 1992; Laurie et al., 1992). Although mRNAs for β2, β3 subunits are expressed early on in the developing rat brain, gene expression of the β1 subunit does not appear until after birth, and it is greatest between postnatal day of 6 and 12 (Laurie, 1992). Interestingly, the expression of β1 subunit mRNAs seen after birth in the cortex and thalamus is barely detectable in the adult rat brain (Laurie, 1992). Expression of the β1 subunit mRNAs in the adult rat brain is limited to the hippocampus. In the rat hippocampus the β1 subunit mRNAs are detected in the pyramidal cell layers with the highest expression in the CA2 cell layer. β1 mRNAs have also been detected in the hilus cells and in the dentate gyrus (Persohn, 1992). The formation of the rat hippocampus takes place after embryonic day 14 and by embryonic day 17 there is a marked expression of α2, α5, and β3 subunit mRNAs but with no detectable expression of β1. These observations indicate that the gene for the β1 subunit is regulated differently than the genes for other α and β subunits. Moreover, the regulation of the promoter for the β1 subunit appears to be different in different regions of the brain.

Supplemental control sequences which affect expression of the β1 gene were obtained from human genomic DNA. Two genomic PCR walking techniques were used to isolate a 541 bp piece of the human genomic DNA (PCR541) that contained sequence upstream to the end of the published Hβ1 cDNA. The transcriptional start sites within PCR541 were then mapped using traditional methods, such as S2 nuclease protection and primer extension, as well as by a novel RNA PCR method that produced cDNA upstream of the 5' end of β1 mRNA. At least two different sets of transcriptional start sites appear for the human β1 subunit gene.

Transcriptional start sites located downstream to the sequence found in the 5' end of the published Hβ1 cDNA (FIG. 7) represent the 5' ends of β1 mRNAs which would code for a protein containing a signal peptide of 9 amino acids rather than the predicted 26 (Schofield et al., 1987). Since no N-terminal sequence has been recovered in the purified β1 subunit, the assignment of the signal peptide length is still tentative. A recent study of the sorting of GABA$_A$ receptor subunits in MDCK cells, which are polarized epithelial cells, has revealed that the co-expression of the β1 subunit with an α1 subunit re-routes the α1 subunit from the basolateral to the apical surface of the cell membrane (Perez-Velazquez and Angelides, 1993). It is possible that the signal peptide of the β1 subunit may play a role in directing the distribution of GABA$_A$ receptor isoforms in the cell. Furthermore, different signal peptides of β1 subunits may subserve alternate functions in the process of GABA$_A$ receptor distribution.

The presence of a TATA-like box upstream of the transcriptional start sites at +103, +112, and +116 (FIG. 7) provides further evidence that these sites correspond to the first nucleotide of human β1 mRNAs. Although the sequence of the TATA box found in this region of the human β1 subunit gene differs from the TATA box consensus, it has previously been reported that extensive variation in the TATA box sequence can be tolerated without affecting the direction or initiation of transcription (Xu et al., *Nucleic Acids Res.* 19(24):6699–6704 (1991)). As the distance between the position of the TATA box and the start site increases, however, there is a dramatic decrease in the efficiency of transcription of most genes. The first TATA box in the human β1 subunit gene is located 25–30 bp upstream of the first set of initiation sites (FIG. 7), consistent with the optimal range for promoter function of 18–35 bp (Xu et al., 1991).

Transcriptional start sites located upstream to the sequence found in the 5' end of the published Hβ1 cDNA (FIG. 14) represent the 5' ends of β1 subunit mRNAs which code for a protein containing the predicted 26 amino acid signal peptide. These transcriptional initiation sites were identified only by using the more sensitive RNA PCR method and could represent the 5' ends of rare β1 subunit mRNAs. An inverted TATA-like box is positioned upstream to these more 5' initiation sites, however, only one of the initiation sites is within the optimal range for promoter function. Studies have shown that the orientation of the TATA box does not affect the direction of transcription; the position of a regulatory sequence upstream of the normal or inverted TATA box determines the direction (see Xu et al. for review). The inverted TATA box in the human β1 gene may be (expected to be functional.

There is a sequence in the β1 promoter (−122 to 109) that shares identity with sequences in the GAP43 and Na channel genes. No function has yet been ascribed to this sequence, other than it is present only in the regulatory regions of genes expressed in the nervous system. By mutational analysis we have identified the "AGG" and TGGAG" nucleotides to be critical regions for binding efficiency. Mutation of one "G" in each sequence abolishes binding of transcription factores derived from non-neuronal tissue. Furthermore, gel shift analysis reveals that non-neuronal extracts from different DNA/protein binding complexes than do neuronal extracts. Interestingly, removal of the −122 to −109 sequence in the β1 promoter does not affect neuron specific gene expression in transient transfection, suggesting that it is not responsible for the tissue specificity that is seen in primary culture studies. However, becuase of the sequence specific binding on non-neuronal extreacts to this region of the promoter, the data suggests that DNA/protein binding may occur in vivo where the context of regulatory sequences within chromatin structure adds an additional complexity to gene expression. Interestingly, Anderson and Schoenherr (*Science*, Mar. 3, 1995, 267: 1360–3) have identified a different sequence in the Na channel gene and in SCG10 that they refer to as NRSE (neuron-restrictive silencer element). This sequence binds a protein (NRSE) that is produced solely in non-neuronal cells, and represses the expression of promoters in non-neuronal tissues. The β1 promoter region does not contain an NRSE. However, we have found from competition binding studies that the NRSE sequence found in the Na channel gene competes for the binding of a protein recognizing the sequence (−122 to −109) in the β1 promoter. Mutational analysis has revealed that the competition is not occurring through the same binding site on the NRSE protein that recognizes NRSE sequence of Anderson & Schoenherr. Our work identified another protein and recognition sequence that plays a role in neuron specific gene expression.

Functional Properties of β1 5' Regulatory Sequences

Transfection into primary cultures of chick brain, rat neocortex, and rat hippocampus with a reporter construct containing PCR541 (FIG. 8) demonstrates that there is an active promoter in the region of the human β1 subunit gene disclosed in FIG. 7. Moreover, promoter activity is orientation specific in all tissues tested. Orientation specificity of promoter activity has been seen for many of the genes which contain TATA boxes.

Although the Sv40 enhancer markedly stimulates the activity of the Sv40 promoter in primary culture of chick brain and rat neocortex, there was no change in the promoter activity of PCR541 when the Sv40 enhancer was added to the reporter construct (FIG. 9). The fact that the Sv40 enhancer does not stimulate the activity of the β1 promoter in PCR541 suggests that the β1 promoter is already in a fully active state (Lewin, 1992). The lack of effect of the Sv40 enhancer on promoter activity indicates that there already is an enhancer in PCR541. When the enhancer region was separated from the promoter, the enhancerless flanking region exhibited reduced promoter activity.

Primary cultures were transfected with luciferase constructs that contained three different segments of PCR541. A luciferase construct (pGLef-253) containing a 253 bp segment of the human β1 subunit gene, extending from +105 to −148, was inactive when transfected into rat neocortical cultures or hippocampal cultures. Luciferase construct PGLef-180 contained a 21 bp region of overlapping sequence with PCR253 and 158 bp of additional upstream sequence extending to nucleotide −307. PGLef-180 was inactive in transfected primary cultures of rat neocortex. However, when cultures were transfected with pGLef-412 which contained both of these pieces, spanning nucleotides +105 to −307, there was a dramatic rise in activity in neocortical and hippocampal culture. This activity was equal to or greater than the activity of PCR541, consistent with the hypotheses that the active state of the β1 promoter depends on an enhancer that is located within PCR180.

Figure 12:
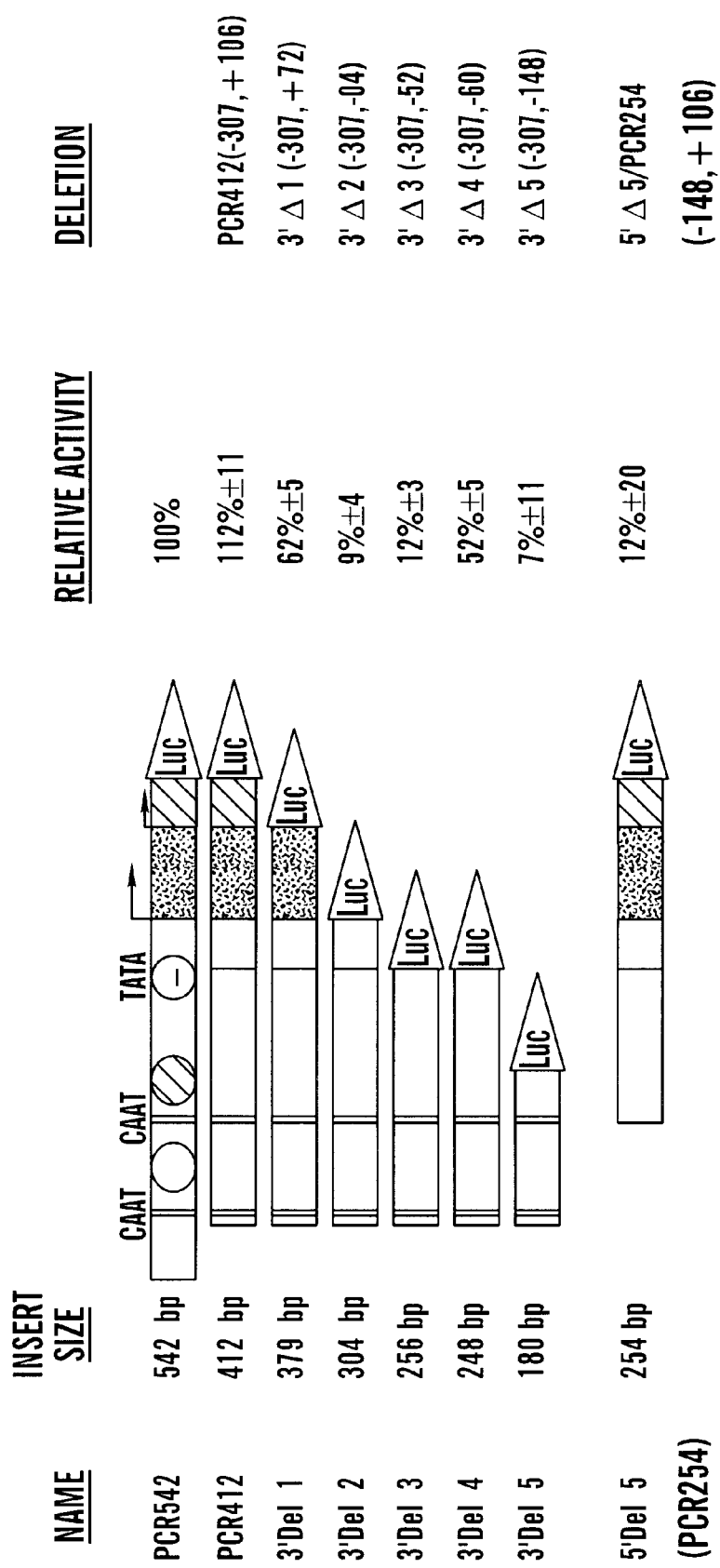

To test whether PCR180 does indeed contain an enhancer, a position and orientation independent recognition sequence, PCR180 was cloned downstream to the luciferase gene producing pGLef-253/180F and pGLef-253/180R (F=forward orientation; R=reverse orientation). To our surprise, both of these constructs were without promoter activity demonstrating that the position of PCR180 relative to the polymerase binding site is important for function. Furthermore, 5' deletional malysis has revealed that the addition of 26 bp, from the 3' end of PCR180, producing 5'DEL4 (see FIG. 7), is sufficient to drive the full expression of β1 promoter in neocortical and hippocampal cultures (FIG. 12). This is an important observation since the consensus sites for two CAAT-boxes are deleted in the making of this construct suggesting that they are not important for core promoter activity as has been found for other eucaryotic TATA-box promoters. However, the presence of the two CAAT-boxes may provide regulatory control since the removal of the second CAAT-box significantly increases β1 promoter activity.

Figure 10:
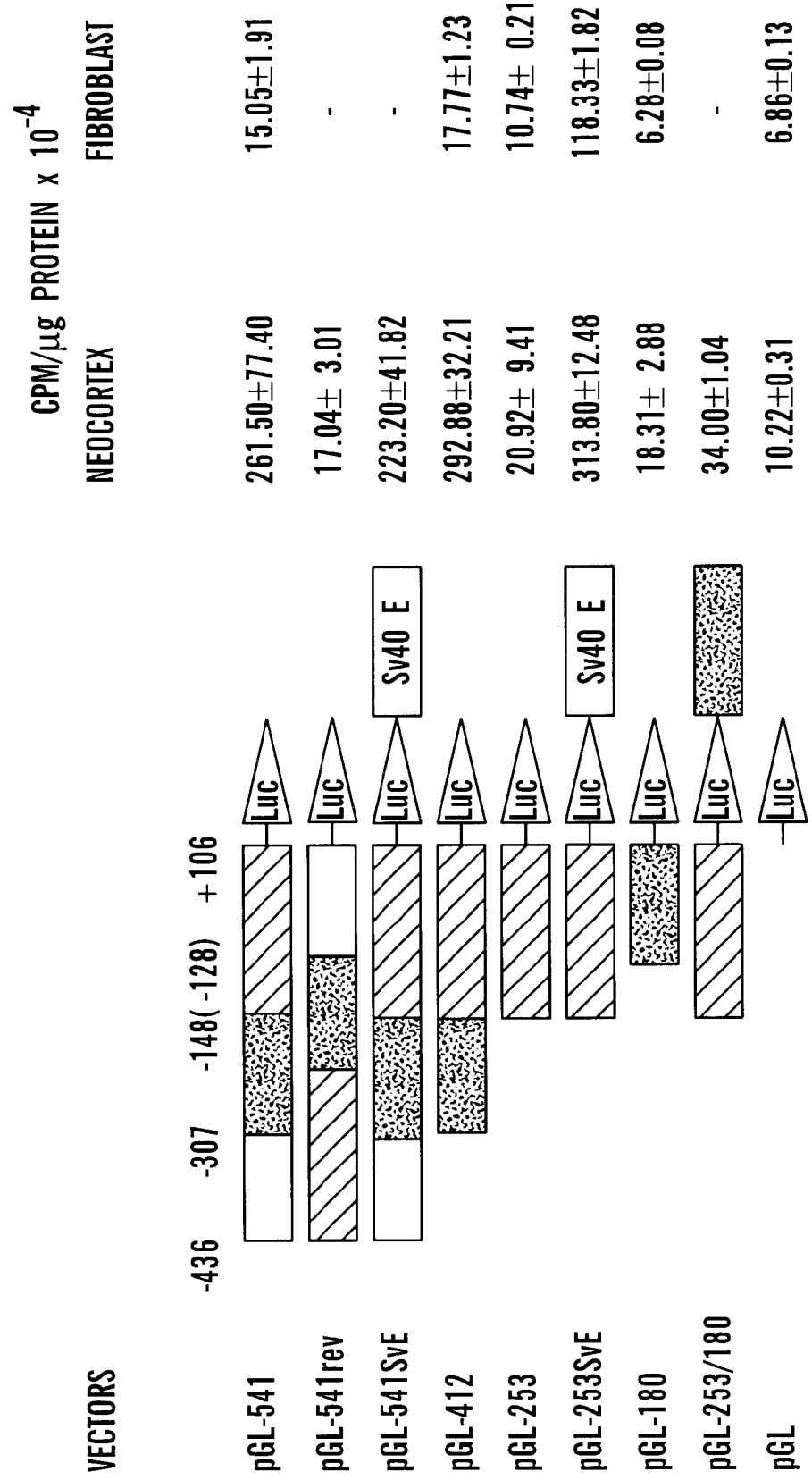
FIGS. 10, 11, and 12 show schematic representations of the vectors used to test the activity of the β1 5' flanking region.

PCR253 supports full transcriptional activity in the presence of the Sv40 enhancer, ruling out the possibility of a crippled promoter located in PCR180. The Sv40 enhancer was added to the reporter construct that contained the 253 bp PCR product. This reporter construct was transfected into rat fibroblast cultures where the Sv40 promoter and enhancer are extremely active. Addition of the Sv40 enhancer to the reporter construct containing PCR253 produced activity in rat fibroblast cultures that was substantially greater than the activity of PCR541 (FIG. 10). The Sv40 enhancer also stimulated luciferase activity in rat neocortical cultures, although the level of stimulation was more variable. These results demonstrate that PCR253 contains the minimal elements of the human β1 promoter. Strikingly, promoter activity is absolutely contingent upon an enhancer. The promoter, which contains the region of EDNA that is recognized by RNA polymerase, is located within the first 148 bp of the 5' flanking region, and in the native genome an enhancer is located upstream within the next 158 bp of 5' flanking region.

PCR541 contains a promoter and or enhancer which is species- and tissue-specific. PCR541 displays very little activity in primary cultures of rat fibroblast when compared to its activity in primary cultures of rat neocortex and rat hippocampus (FIG. 15). β1 promoter activity is also extremely low in primary cultures of chick brain and in rat cultures enriched for muscle cells. In contrast, the Sv40 promoter and enhancer are at their highest levels in these latter cultures while exhibiting a low and variable level of activity in primary cultures of rat neocortex and hippocampus. PCR412 is also inactive in fibroblast cultures suggesting that the tissue-specific element(s) are not located between nucleotides −412 to −436. Moreover, there is a sequence motif in the 5' end of PCR253 that has been found previously in the genes that are selectively expressed in rat neurons.

TABLE 1

Structural analysis of the 5' flanking region of the human β1 gene:

a. PCR541 contains 496 bp of sequence upstream to the published "full length" human β1 cDNA (Hβ1cDNA).
b. Transcriptional start sites located downstream to the sequence found in the Hβ1cDNA appear to represent the 5' ends of β1 mRNAs that code for a 9 amino acid signal peptide. Transcriptional start sites located upstream to the sequence found in the Hβ1cDNA represent the 5' ends of β1 mRNAs that code for a 26 amino acid signal peptide. To provide a single base for numbering purposes, the most

TABLE 1-continued

Structural analysis of the 5' flanking region
of the human β1 gene:

5' start site will be referred to as +1 hereinafter.
All sequence upstream of this site is considered part of the 5'
flanking region of the human β1 gene.

c. Sequence analysis of PCR541 reveals the existence of a number
of consensus sequences for promoter and transcriptional stimulatory
elements (see FIG. 7). There are consensus sequences for AP1,
SP1, and GRE elements; TATA-, CAAT-, and CACCC-boxes; as
well as AA-control elements which are similar to those found in
the regulatory regions of genes coding for enzymes involved in
the biosynthetic pathway of amino acids (Hinnebusch, et al.,
1993).

i. TATA-like boxes located upstream of both sets of transcriptional
initiation sites. A TATA box at +76 is upstream from five
start sites (of which only three are within range for promoter
function). An inverted TATA-like box is located at −58 (but
it is positioned more than 35 bp upstream of the
start sites at +1, +7, +15 and +33).

ii. Four initiator (Inr) sequences are associated, collectively, with
eight of the eleven mapped transcriptional start sites. An AP1 site
that is located on both the positive and negative strands at +76 (+,
TTAATCA; −, TGATTAA) shares sequence with the TATA
box at +73 as well as the 5' end of an Inr. Two other AP1
sites are adjacent to or overlapping with Inr sequences (FIG. 7).
There is a site for the human CAP binding protein that overlaps
with the Inr at −2. Two of three AP1 sites are found on the
negative strand at +37 (TTAAGTCG) and −127 (GTAAGTCA),
the latter sharing sequence with the AA-control element at −133.

iii. A GRE element overlaps the motif AGGAGATGGAGC
SEQ ID NO: 3 (−110 to −122) which is found in the 5' flanking
regions of neural-selective genes such as at −50 to −39 in the
rat type II sodium channel gene.

iv. Other regulatory sequences include the binding sites for
proteins that bend DNA (SRY and Helix Fork Helix 2) at −222,
the Ebox at −172, the insulin enhancer core motif at −150 that
overlaps with an AP4 site, the Octamer 1 site at −48, the delta
EF1 repressor at −31, the homeobox Deformed (DFD)
site at +71, and the heat shock protein sites HSF1 and
HSF3 at +22 and +54 respectively.

v. An A-rich region is flanked by two CAAT boxes located at
−203 and −295, respectively.

TABLE 2

Functional analysis of the 5' flanking region of the
human β1 submit gene:

a. PCR541 exhibited orientation-specific promoter activity in
transfected cultures of chick brain, rat neocortex,
and rat hippocampus.

b. Addition of the Sv40 enhancer markedly stimulated Sv40
promoter activity. However, addition of the Sv40 enhancer
did not stimulate the activity of PCR541, indicating that PCR541
already contained an enhancer.

c. Transfection of a reporter vector that contained PCR53, a
253 bp PCR product of PCR541 with a 5' deletion, produced
no promoter activity. However, addition of the Sv40 enhancer to
this vector stimulated promoter activity indicating that the β1
promoter was located within the first 148 bp of 5' flanking region.

d. Transfection of a reporter vector that contained PCR180, a
180 bp PCR product that resulted from both a 5' and 3' deletion
of PCR541, produced no promoter activity. However,
transfection with a reporter vector that contained PCR412,
a 412 bp PCR product spanning both PCR180 and PCR53,
produced full, orientation-specific activity. The localization of the
β1 promoter to the first 148 bp of 5' flanking region and the
activity driven by PCR412 indicates that the enhancer was located
within 159 the bp that are found upstream of PCR253.

e. Transfection into primary cultures of rat muscle, fibroblast,
neocortex, hippocampus and chick brain demonstrates that the
activity of the human β1 promoter within PCR541 was species-
and tissue-specific.

Regulatory Sequences in Intron-1

The importance of introns to gene regulation is well documented (Banerji et al., Cell 33:729–740 (1983); Buchman and Berg, Mol. Cell. Biol. 8:4395–4405 (1988)). Differential development expression of $GABA_A$ receptor subunits and subunit specific mRNAs (Laurie et al., 1991) suggests that the $GABA_A$ receptor genes contain unique developmental regulatory sequences that orchestrate the expression of $GABA_A$ receptor isoforms. Because of these observations, the sequences of the introns in the β1 gene were analyzed to see if any regulatory elements could be identified.

Intron position is conserved in the 5' ends of the human and rat β1, β2, and β3 genes which suggests that these genes evolved from a common ancestor. Exon-1 is separated from the rest of the coding region by an intron (intron-1) that interrupts the second codon (Ser) of the mature polypeptide (FIG. 4). The first exon of the rat and human β1, β2 and β3 genes contains the untranslated region and signal peptide sequences. The position of introns in mammalian genes is often correlated with the presence of a functional unit such as the signal peptide or a transmembrane domain.

While intron position is conserved, the sequence of the first exon is unique for each of the β1, β2, and β3 genes. Moreover, for a given gene, the sequence of the first exon is homologous for human and rat, and thus conserved across species. This suggests that the first exon contains information that is important to subunit specific expression.

By comparison, while the sequence of intron-1 is unique for each of the β1, β2, and β3 genes there is little or no homology between human and rat, suggesting that the sequence of intron-1 has evolved more rapidly than that of exon-1. Interestingly, however, the β1, β2, and β3 genes can be distinguished from one another by a stretch of nucleotides at the left splice junction of the first intron (FIG. 6) and each small stretch of intervening sequence is conserved for the β1, β2, and β3 genes in human and rat. The fact that each of the three β genes contains a unique intervening sequence that is conserved demonstrates that the duplication of the genes for the β subunits occurred prior to the divergence of the human and rat species. It also suggests that sequences within the first introns may be critical to the processing of the RNA transcript and therefore represent another level of transcriptional regulation (Darnell, Lodish, and Baltimore, 1990).

The first intron of the human β1 gene contains a consensus sequence for the human TATA box binding factor that is located 30 to 50 bp upstream of three consensus sequences for initiation of transcription. Although the TATA box is generally found in the promoter region (Wu et al., 1987), if it is functional in intron-1, initiation of transcription at this site would produce RNA transcripts without leader and signal peptide sequences. The fact that intron-1 can drive expression of the luciferase gene in primary neuronal cultures suggests that the TATA box may indeed by functional. Interestingly, there is evidence for an intracellular pool of $GABA_A$ receptors. Since the signal peptide has been shown to play an important role in the targeting of proteins to the membrane, the receptor subunits within this intracellular pool may not contain a signal peptide.

The first intron contains a CCAAT box that is conserved in the rat and human β1 genes. A negative regulatory sequence that is a reverse CCAAT box has already been characterized in the first intron of the proliferating cell nuclear antigen gene (Alder et al., 1992). It is believed that the inhibitory effect of this regulatory element is removed when specific proteins bind to it and that inhibition is restored if it competes for the binding of proteins that are necessary for promoter function. Because the CCAAT box is conserved in the human and rat β1 genes, it may also be the negative regulatory element within the first intron that is responsible for the repression of β1 promoter activity. Furthermore, there are two CCAAT boxes in the 5' flanking region of the β1 gene that may be critic al for gene expression. It is possible that the CCAAT box in the intron may complete for the transcription factors that bind to the CCAAT boxes in the 5' flanking region leading to the inhibition of transcription.

Functional Properties of Intron-1 Sequences

Developmental regulatory sequences that control the expression of the β1 subunit in different cells were located in the first intron of the human β1 gene. When these sequences were added to the luciferase reporter construct that contained PCR541 (pGL-541IS$_1$), the presence of the first intron dramatically decreased the activity of the human β1 promoter in all rat tissues tested (neocortex, muscle, and fibroblast) (FIG. 20).

Primary cultures of rat hippocampus and neocortex were made from dissociated cultures of embryonic day 17 rat brain, which does not contain β1 subunit mRNAs (Laurie et al., 1992). It is unknown at this time whether the culturing conditions sponsor the expression of β1 mRNAs that would not normally be present in vivo. If β1 mRNAs are not present in rat hippocampal and neocortical cultures, then these cultures will provide an excellent system with which to test the developmental activity of pGL-541IS$_1$. Transfection of pGL-541IS$_1$ into older cultures that express β1 mRNAs should produce full activity from the β1 promoter in the presence of the first intron. Transfection of pGL-541IS$_1$ into younger cultures that do not express β1 mRNAs should not produce full activity of the β1 promoter in any neuronal culture.

TABLE 3

Comparative analysis of intron sequence and position in the β1, β2, and β3 subunits of the GABA$_A$ receptor:

f. Intron 1 interrupts the second codon (Ser) of the mature protein in the human and rat β1, β2, and β3 genes.
g. Intron 2 interrupts the codon for glycine (residue 32) in the Rβ1, Rβ2, Rβ3, and Hβ1 genes.
h. The β1, and β2, and β3 genes can be distinguished from one another by the sequences at the 5' ends of the first introns, in addition to certain coding sequences,. These 5' sequences are conserved in the human and rat genes.
i. The first intron of the human β1 gene contains the consensus sequences for a TFIID TATA box binding factor and a CAAT box. The CAAT box is conserved in the rat β1 gene.
j. Presence of the first intron of the human β1 gene dramatically repressed the activity of the human β1 promoter in transfected primary cultures of rat neocortex, muscle, and fibroblast. This observation demonstrates that the first intron of the human β1 gene plays a role in the developmental expression of β1 subunit mRNAs.
k. The sequences at the 5' ends of the β2 gene introns obey the extended 5' splice-site consensus sequence of GTAAGT. Two consensus sequences for known transcriptional regulatory elements GH2 and INF.I are conserved in the first introns of the rat and human β2 genes. The sequence at the 5' end of the first intron of the chicken β4 gene is most similar to the sequence found in the β2 gene.
l. The first intron of the human β3 gene has characteristics of a CpG island and contains the consensus sequences for two SpI sites with dyad symmetry. These sequences are not conserved in the rat β3 gene. The first intron of the rat β3 gene contains the consensus sequences for steroid responsive elements.

Regulation of Gene Expression by Extracellular Molecules

Promoter activity of the human β1 promoter may come under the control of a number of different regulatory signals. Some of these signals may be produced in response to the activation of membrane bound receptors. For instance, chronic treatment of neurons with GABA produces a down regulation of GABA$_A$ receptor number and an uncoupling of the allosteric interactions between the GABA and benzodiazepine recognition sites.

Figure 16:
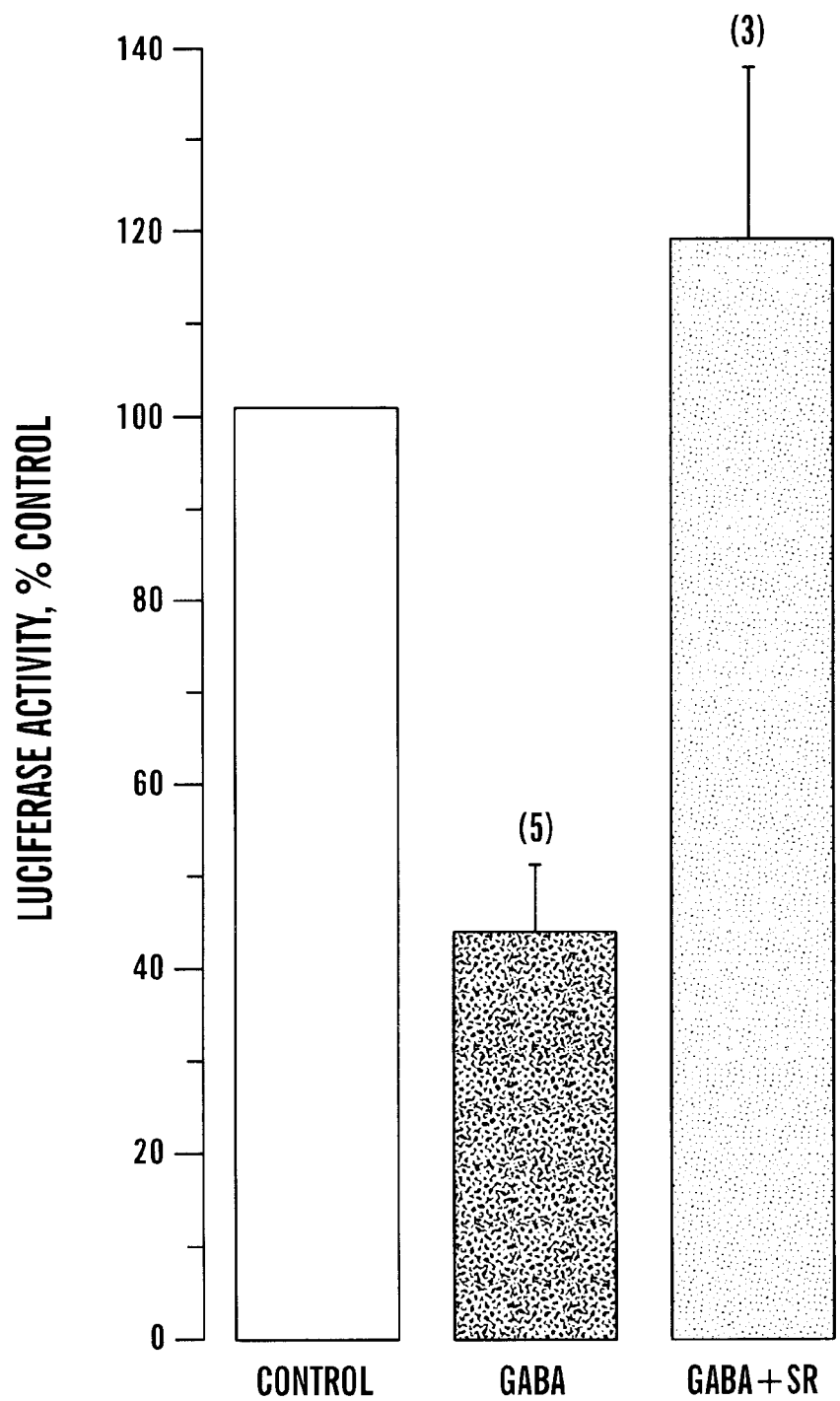
FIG. 16 shows that chronic exposure to GABA produced down regulation of human β1 GABA$_A$ receptor promoter activity in primary cultures of rat neocortex which were chronically treated for 48 hours with either 0.5 mM GABA or 0.5 mM GABA and 0.25 mM SR95531.
Figure 17:
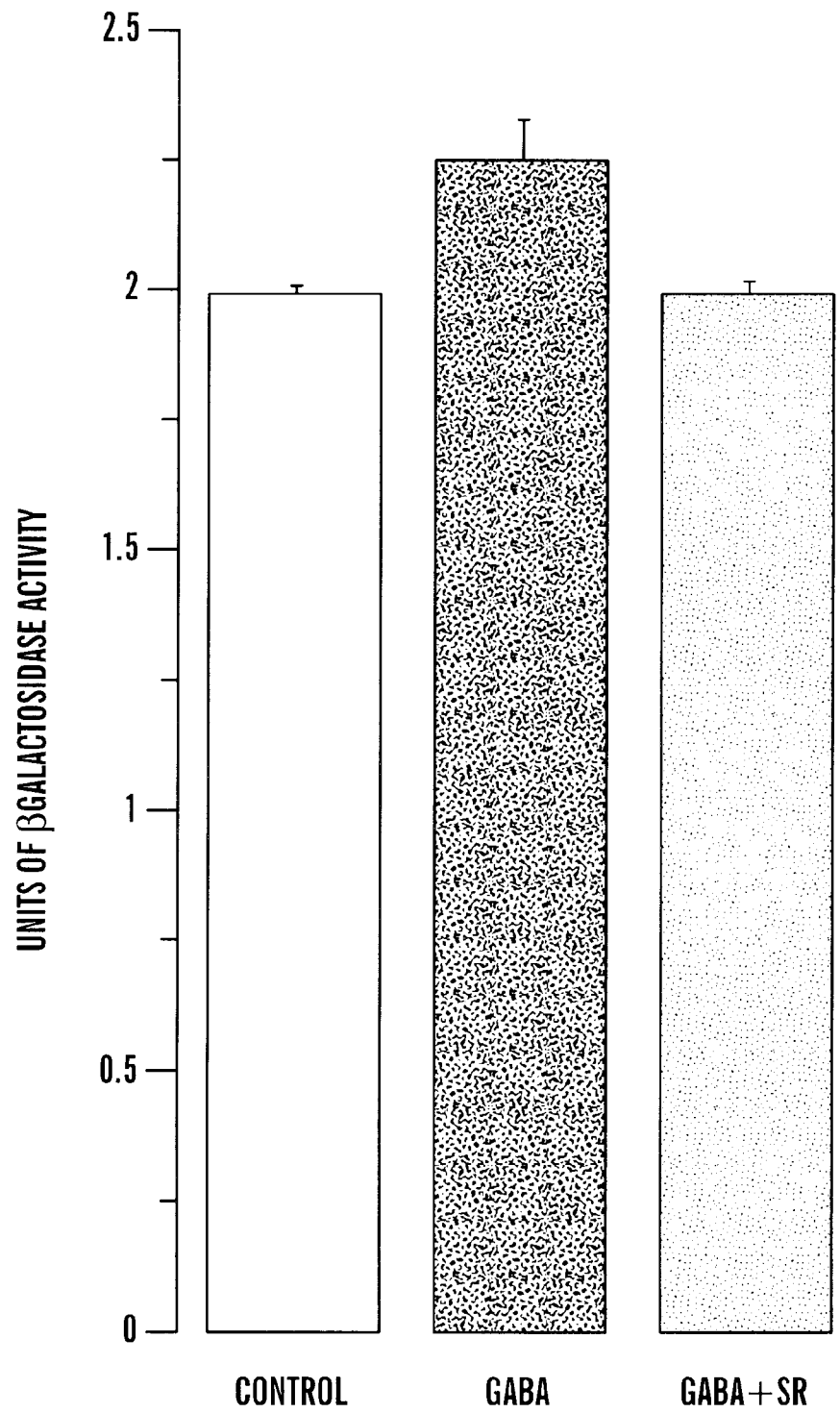
FIG. 17 shows that chronic treatment with GABA did not regulate the activity of the SV40 promoter in primary rat neocortical cultures which were co-transfected with pGlef-541 and pSVP, a β-galactosidase reporter vector that contained the Sv40 promoter and enhancer upstream of the β-galactosidase gene.
Figure 18:
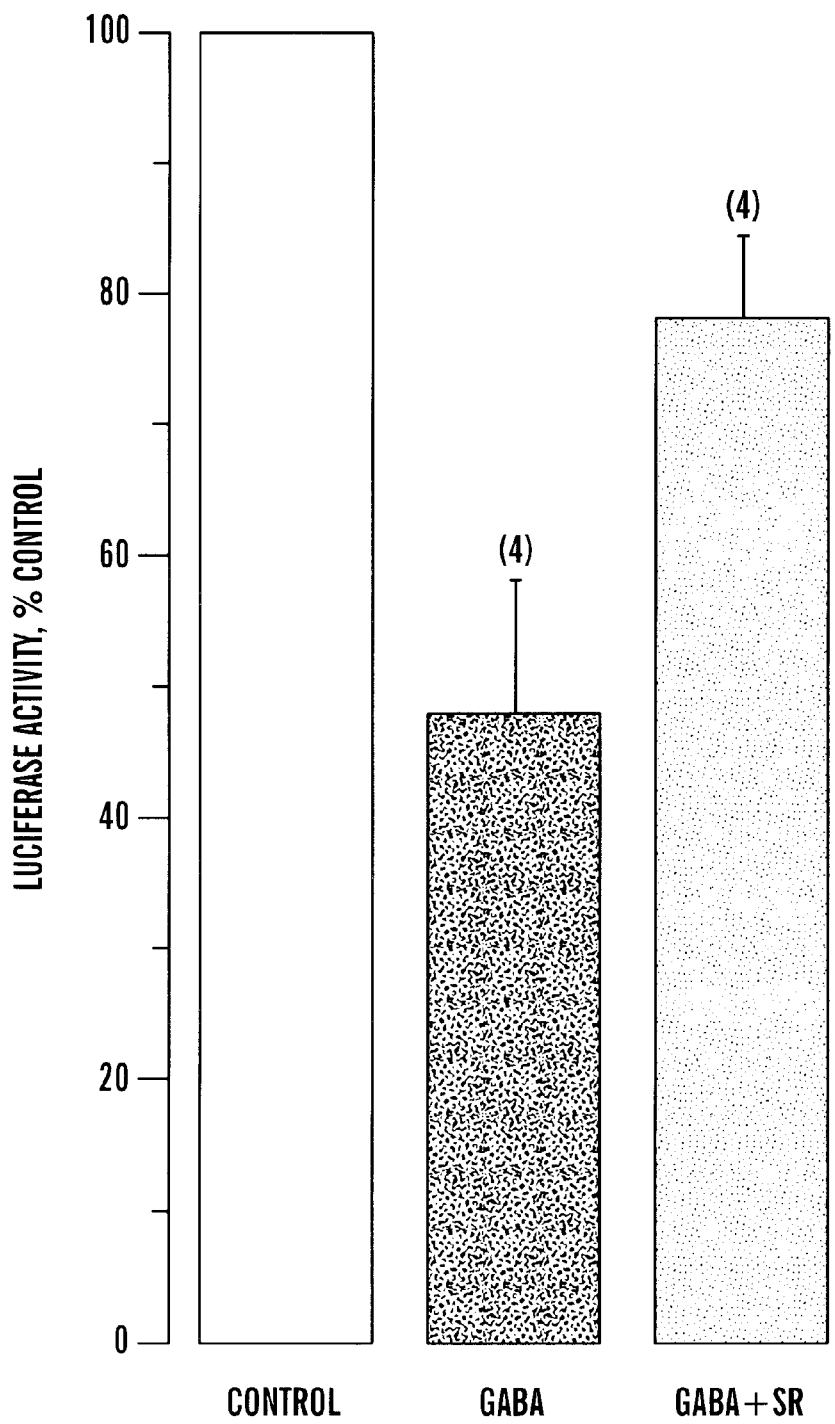
FIG. 18 shows that chronic exposure to GABA produced down regulation of human β1 GABA$_A$ receptor promoter activity in primary cultures of rat hippocampus.

Chronic exposure to GABA produced a receptor-specific down-regulation of human β1 promoter activity in rat neocortical cultures (FIG. 16). A receptor-specific down-regulation of promoter activity was also seen in chronically-treated hippocampal cultures (FIG. 18). To determine whether down regulation of promoter activity induced by chronic exposure to GABA was specific to the human β1 promoter, primary cultures of rat neocortex were transfected with pGLef-541 and a control plasmid that contained the Sv40 promoter upstream of the βgalactosidase reporter gene. Sv40 promoter activity was unchanged after chronic exposure to GABA, but β1 promoter activity decreased (FIG. 17). The effects of GABA were also receptor-specific since they were reversed by co-treatment with the GABA$_A$ receptor antagonist SR95531. Chronic treatment of primary cultures with SR95531 alone had no significant effect on promoter activity (data not shown).

A computer analysis of the sequence contained within PCR541 uncovered the existence of consensus sequences for AA-Control elements. AA-control elements have been found in the genes that code for enzymes that are involved in the biosynthesis of amino acids, and they may play an important role in controlling the levels of amino acids within the cell. GABA is an amino acid neurotransmitter, and it is possible that the AA-control elements contribute to the GABA-induced down regulation of human β1 promoter activity.

Dynamic changes in GABA$_A$ receptor function reflect a complexity of transcriptional and posttranscriptional regulatory mechanisms. It has been demonstrated that PCR541 contains the regulatory sequences that respond to chronic GABA treatment; however, post-transcriptional events may also contribute to the final output of β1 mRNA that is available for translation at the ribosome. The untranslated region of mRNA may also contain regulatory elements that play an important role in determining the levels of mRNA that are available for translation in the cell (Aziz and Munro, Proc. Natl. Acad. Sci. U.S.A. 84:8478–8482 (1987); Ilan, Translational regulation of gene expression (1987); Kozak, Cell 47:481–483 (1986); and Walden et al., Proc. Natl. Acad. Sci. U.S.A. 85:9503–9507 (1988)).

Figure 19:
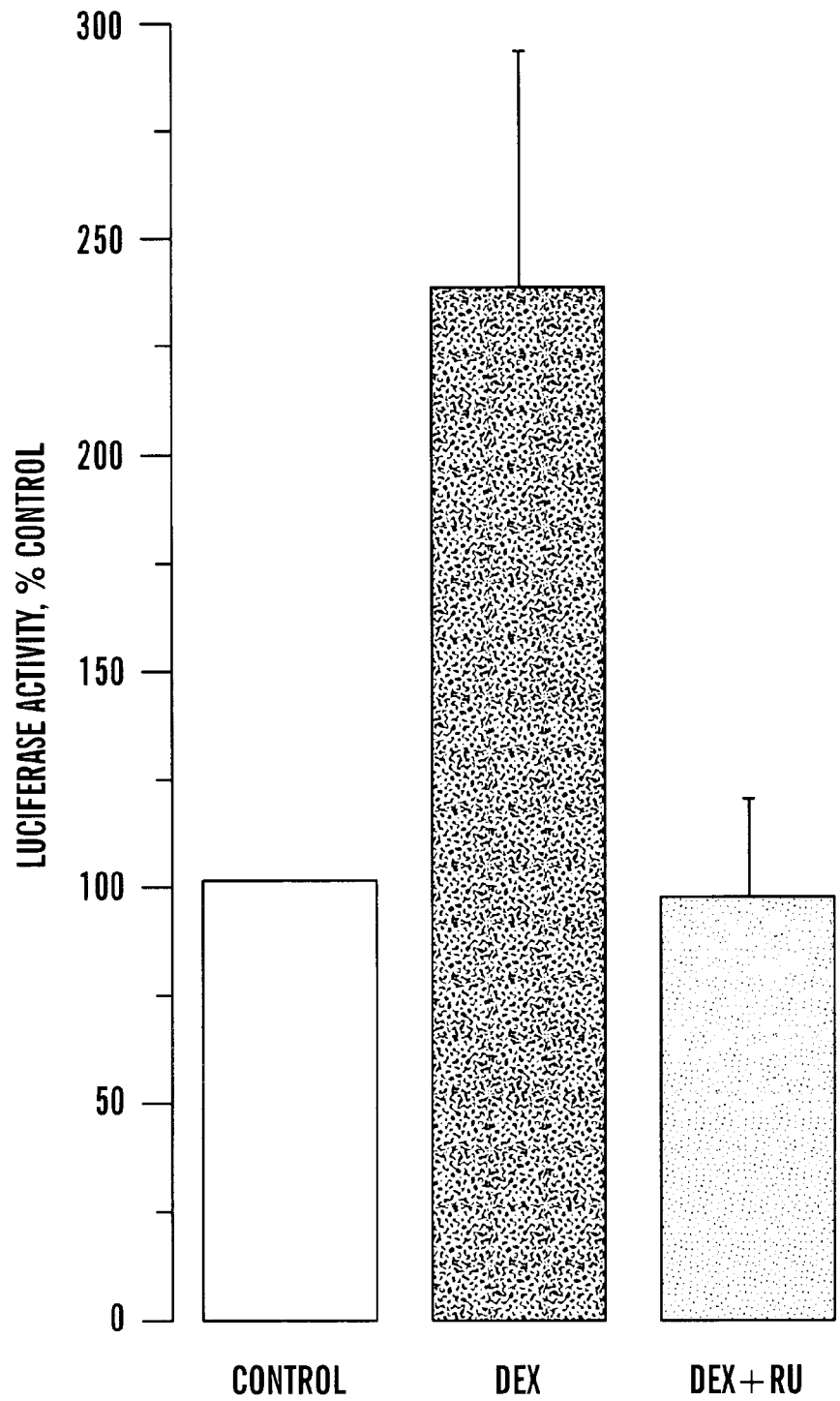
FIG. 19 shows that steroids regulate the activity of the human β1 subunit promoter.
Figure 20A:
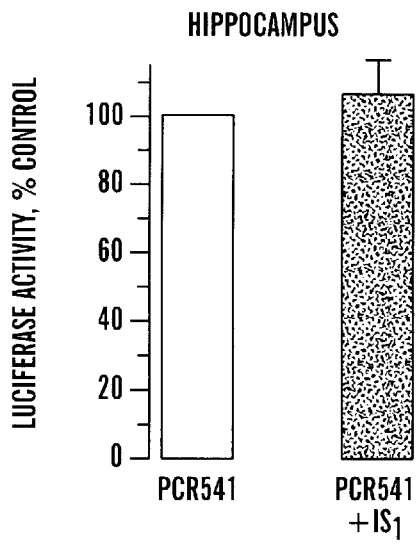
FIGS. 20A–D shows that the first intron of the human β1 GABA$_A$ receptor gene, when positioned downstream of the luciferase gene in reverse orientation, repressed the activity of the human β1 promoter. Primary cultures of rat muscle, fibroblast, neocortex and hippocampus were transfected with either pGLef-541 or pGLef-541Is$_1$. pGLef-541Is$_1$ contained the first intron of the human β1 gene downstream of the luciferase gene.
Figure 20B:
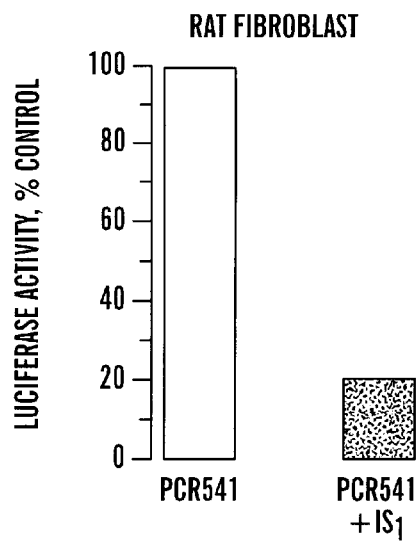
Figure 20C:
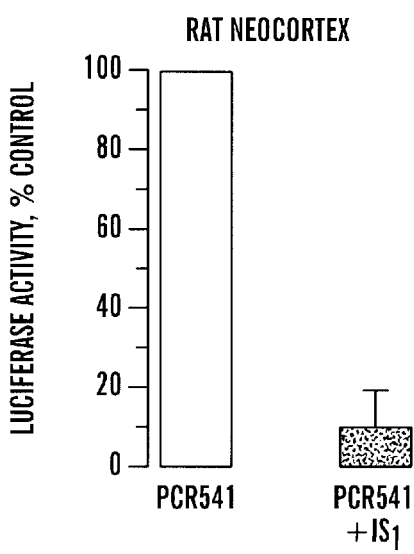
Figure 20D:
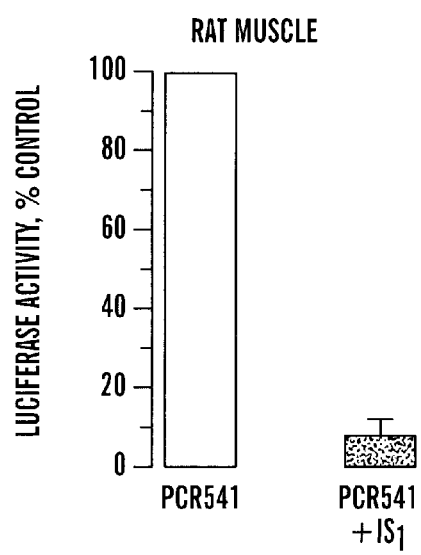

The activity of human β1 promoter may also be regulated by other receptor-mediated events. The hippocampus contains the greatest density of intracellular steroid receptors in the brain. Changes in the levels of circulating adrenal steroids that take place during stress and aging have been implicated in the destruction of important regions of the hippocampus. Because the β1 gene is highly expressed in the hippocampus, primary cultures of rat hippocampus were chronically treated with dexamethasone. Dexamethasone treatment produced a marked stimulation in the levels of promoter activity for PCR541 (FIG. 19).

The results of chronic GABA treatment have shown that the β1 promoter is autologously regulated, indicating that activation of cell surface GABA$_A$ receptors can affect the transcription of GABA$_A$ receptor genes. The activity of the β1 promoter is also modulated by adrenal steroids providing another dynamic mechanism for changes in β1 subunit expression. Transcription of the β1 gene is dependent on enhancer activity within 159 bp upstream of the first 148 bp of 5' flanking region, and the first intron contains a powerful negative regulatory element. The isolation and characterization of the human β1 promoter should lead to studies that are aimed at a better understanding of the mechanisms by which gene expression can regulate neurotransmitter receptor function in the central nervous system (i.e., study of the β1 promoter in an in vivo model such as a transgenic animal that retains the proper tissue-specific and developmental context for β1 subunit gene expression.).

TABLE 4

Regulation of the human β1 subunit gene:

Homologous regulation through activation by its own gene product a. Chronic exposure to 0.5 mM GABA of primary rat neocortical cultures transfected with a reporter vector containing PCR541 produced a significant decrease in promoter activity (43.4% ± 7% of control; $p < .002$).
   This decrease in activity was receptor specific, as it was reversed by cotreatment with the competitive GABA antagonist SR95531 (118.67 ± 18.7% of control; $p < .001$).
b. Chronic exposure to 0.5 mM GABA of primary rat hippocampal cultures transfected with a reporter vector containing PCR541 produced a significant decrease in promoter activity (48 ± 10% of control) ($p < .02$). This decrease in activity was receptor specific, as it was reversed by co-treatment with the competitive GABA antagonist SR95531 (78 ± 7% of control; $p < .05$).
c. Activity of primary neocortical cultures transfected with a reporter vector containing the Sv40 promoter and enhancer was not affected by chronic GABA treatment, indicating that the GABA-induced down regulation of promoter activity is specific to the β1 promoter.

Heterologous Regulation d. Chronic exposure to dexamethasone stimulated the activity of the human β1 promoter in transfected hippocampal cultures (233 ± 58% of control). The increase in activity was receptor specific, as it was reversed by co-treatment with the steroid antagonist RU486 (96 ± 2% of control).
e. Exposure to ethanol produced downregulation of promoter activity.

The β1 promoter construct as described herein can be used is a model on which to base the design of transcript delivery systems that target gene expression to a particular set or subset of cells. The use of two promoters, one for the primary transcript and the other for antisense, can provide the additional control system needed to fine tune the genetically engineered expression of a particular transcript in the living organism. This is especially important because promoters previously thought to be tissue specific have been found to have an unacceptable range of expression that curtails their usage, even though they demonstrate a preference for expression in a particular cell type. The fact that intron-1 of the β1 promoter fine tunes expression of the luciferase reporter gene to hippocampal neurons demonstrates the power of such a gene delivery system. One can also imagine a situation where it is important to arrest transcription of a foreign gene to keep the expression of interest dynamically controlled, as in pulsatile delivery of gene transcripts. A constitutive promoter in concert with an inducible antisense promoter would provide an additional level of control.

Promoters for receptor subunits that are autologously regulated by drugs with their site of action on the endogenous receptor can provide a unique way of regulating transcript delivery. In one example, a constitutive promoter is provided which drives the expression of the γ2 subunit gene of the GABA$_A$ receptor (this subunit confers benzodiazepine sensitivity to the receptor). In addition, an antisense promoter (the β1 promoter) provided downstream of the reporter gene is modulated by the presence of GABA and ligands working at the GABA$_A$ receptor, such as benzodiazepiles. When GABA is present at normal levels, the antisense promoter is active, and there is no expression of the γ2 subunit gene. However, in the presence of chronic GABA (which downregulates β1 promoter activity), the expression of the γ2 gene is disinhibited, and there is an increase in γ2 receptor subunit gene expression.

In another example, a constitutive or regulated promoter is provided which drives the expression of an antisense transcript for the NR1 gene (NMDA receptor subunit gene), and a promoter that is downregulated by chronic glutamate exposure drives the expression of the sense NR1 transcript. Because chronic glutamate is associated with excitotoxicity, mediated by the NMDA receptor, unleashing the antisense transcripts generated by the constitutive promoter would downregulate the number of NMDA receptors, breaking the cycle of cell death. In the absence of chronic glutamate, expression would be silent due to the arrest of translation from the transcripts of two active promoters.

In addition to providing a vehicle for cell specific expression, a two promoter system can be used to deliver particular transcripts in a developmentally specific manner. For example, a constitutive promoter can be used to produce the sense transcript and an antisense developmentally regulated promoter can be used to inhibit translation at a particular time period. A transcript that is necessary only during the prenatal period can be translationally arrested by the production of antisense transcripts directed by a promoter that is only active after birth. Alternatively, if one is to deliver a target gene after the prenatal period, an antisense promoter can be used that is only active during the prenatal period. This approach can be very powerful if gene expression is toxic to the organism at a particular time in development. Promoters displaying very restricted developmental profiles necessary for the development of body plan have been already identified and would provide the necessary tools for the design of constructs utilizing this aforementioned strategy.

One can also see the applicability of a two promoter system in the treatment of neurodegenerative diseases such as Parkinsonism. This approach allows changes in the endogenous environment to be translated into alterations in foreign gene expression that can also be controlled by the application of extrinsic agents. However, it will be especially important to match the strengths of the two promoters to maintain the necessary control over foreign and endogenous gene expression.

The use of receptor subunit promoters that are autologously regulated is also very important for the identification of new therapies that work at the level of gene expression. It is known from work described herein that the β1 promoter responds to ligands active at the GABA$_A$ receptor. By monitoring alterations in promoter activity that occur in response to chronic drug treatment, one can identify new compounds that affect the feedback loop between receptor activation and receptor gene expression. By using a constitutive promoter driving the expression of a reporter gene and the β1 promoter of this instrument driving antisense reporter gene expression, one can identify novel compounds that disinhibit the ability of ligands, such as ethanol, to downregulate promoter activity. Compounds that inhibit reporter gene activity in the presence of chronic ethanol or GABA may be components in treating the long-term genomic effects of chronic GABA$_A$ receptor activity. Likewise, this approach can be used to identify new agents that are aimed at treating the long-term genomic effects of chronic GABA$_A$ receptor inactivity by exploiting the upregulation of reporter gene transcription by steroids.

EXAMPLES

In order to facilitate a more complete understanding of the invention, a number of Examples are provided below. However, the scope of the invention is not limited to specific embodiments disclosed in these Examples, which are for purposes of illustration only.

EXAMPLE 1A

Subcloning and Sequencing of Genomic Clones

Restriction fragments of DNA from genomic clones were obtained by double digestion with either EcoRI/KpnI or SalI/KpnI. Digests were shotgun cloned into the pBluescript IIKS+ vector. Subclones were screened by colony lift hybridization and Southern blot analysis with probes 1 and 2. Positive subclones were then sequenced using double stranded dideoxysequencing.

Identification of the first three exons of the human β1 gene by PCR.

A 958 bp PCR product containing the 5' end of the Hβ1 gene was obtained using an antisense primer A', which begins at nucleotide 240 of the Hβ1 cDNA, and a sense primer A, which begins at nucleotide −26 of the Hβ1 cDNA. Southern analysis of the 958 bp PCR product with Probe 1 suggested that the amplified DNA contained part of the gene for the β1 subunit of the GABA$_A$ receptor. The PCR product was then cloned into pBluescript IIKS+ vector and sequenced (FIG. 4). Analysis of the sequence of this PCR product revealed that it contained most of the first and all of the second and third exons of the Hβ1 gene. The left (or 5') and the right (or 3') splice junctions of intron 1 and intron 2 obeyed the GT-AG rule (see Lewin, 1987).

Identification of coding region within the first three exons of the rat β1 gene by PCR.

A ~1 kb PCR product containing the 5' end of the rat β1 gene was obtained using the same approach as described above (see Table 4 for primer sequences). A sequence comparison of the rat and human β1 genes is presented in FIG. 5. Any variation in the nucleotide sequence between the two genes was due to rat codon usage and, therefore, did not affect the amino acid sequence of the proteins. The left (or 5') and the right (or 3') splice junctions of intron 1 and intron 2 of the rat β1 gene also obeyed that GT-AG rule (see Lewin, 1987).

EXAMPLE 1B

Sequencing Comparisons Among the First Introns of the β1, β2, and β3 Genes

By using sense and antisense primers designed from the rat β2 and β3 cDNAs, it was possible to amplify regions of these genes from both human and rat DNA. Antisense primer C' was selected based upon the observation that the Rβ2 and Rβ3 cDNAs are homologous from nucleotides 223 to 230. To differentiate the rat β2 and β3 genes, sense primers were made either to the 5' end of the Rβ2 cDNA or to the beginning of the coding region of the Rβ3 cDNA.

Using antisense primer C', which begins at nucleotide 230, and sense primer C, which begins at nucleotide −77 and the Rβ2 cDNA, it was possible to amplify a region of rat genomic DNA that contained most of the first and all of the second and third exons of the rat β2 gene.

Antisense primer D', which begins at nucleotide 133 of the β2 cDNA, was used together with sense primer C to amplify most of the first and second exon of the human β2 gene. A sequence comparison of the first two exons of the rat and human β2 genes was made.

By designing antisense primer E', which contains a correction for the mismatched nucleotide in antisense primer C', and sense primer D, which begins at the first nucleotide of the coding region of the Rβ3 cDNA, it was possible to obtain a single PCR product that contained most of the first and all of the second and third exons of the rat β3 gene.

Using sense primer D and antisense primer F', which begins at nucleotide 152 of the Rβ3 cDNA, it was possible to amplify a region of human DNA that contains most of the first and all of the second exon of the human β3 gene. A sequence comparison of the first two exons of the rat and human β3 genes was made.

The left (or 5') and the right (or 3') splice junctions of intron 1 and intron 2 in the rat β2 and β3 genes obeyed the GT-AG rule (see Lewin, 1987). This was also the case for intron 1 of the human β2 and β3 genes.

When the exon/intron structure of the β1, β2, and β3 genes is compared it can be seen that intron position is identical for the different genes investigated.

β1, β2, and β3 genes can be distinguished by sequences at the left and right splice junctions of intron 1.

There is sequence conservation at the splice junctions of the first introns in each of the β1, β2 and β3 genes (see FIG. 6). The left (or 5') splice junction of the first intron in the β1 gene contains the consensus dinucleotide GT followed by GAGCTA(− or C)CTG, where (−) represents a gap in the sequence for comparison. This small stretch of nucleotides is not present in the β2 or β3 genes. There is also a conserved sequence TGAATCTCTCT SEQ ID NO:4 downstream of the left splice junction in the β1 gene. The consensus trinucleotide TAG at the right (or 3') splice junction of the β1 gene is also found in the β2 gene, but not the β3 gene. The β2 gene is the only β gene to contain the extended 5' consensus sequence GTAAGTC at the left splice junction. The left splice junction in the β3 gene contains the consensus dinucleotide GT followed by GTAGGGTCGC(GORT) GGTGGG SEQ ID NO:5 which is not present in the, β1 or β2 genes. The β3 gene also contains the consensus trinucleotide CAG at the right splice junction.

The first intron of the human β1 gene contains a TFIID TATA box consensus sequence.

There are also consensus sequences for two eukaryotic transcriptional initiation sites located 30 to 40 bp downstream from the TFIID TATA box sequence and an upstream CAAT box (see FIG. 4).

EXAMPLE 2

Novel Genomic Walking Methods Using PCR

Inverse PCR and locus expansion PCR were used to amplify genomic DNA containing the 5' flanking region of the human β1 GABA$_A$ receptor subunit gene. These techniques made it possible to recover DNA of unknown sequence upstream from the end of the published human β1 cDNA sequence.

Inverse PCR

Inverse PCR was carried out. Briefly, 3 μg of human genomic DNA in deionized water dH$_2$O was first digested with 1.0 μl of MspI (~10U), 2.0 μl of 10×restriction buffer (to a total volume of 20 μl) for 3 hrs at 37° C. The restricted DNA was then ethanol precipitated, washed once with 70% cold ethanol, desiccated, and resuspended in 20 μl of dH$_2$O. Dilute ligation was performed overnight containing 3.5 μl of the restricted genomic DNA, 15.0 μl of 10×ligation buffer containing 660 μM ATP, 3.0 μl of T4 DNA ligase (48U), and 128.5 μl of dH$_2$O. After inactivation of the ligase at 75° C. for 20 min, the DNA was ethanol precipitated, resuspended in 20 μl of dH$_2$O, and then digested for 3 hrs at 37° with NcoI in a final volume of 50 μl. After inactivation of the enzyme at 75° C. for 30 min, the DNA was ethanol precipitated, washed once with 70% ethanol, resuspended in 20 μl of dH$_2$O, and used in a standard PCR reaction with the following primers: sense (5'CCATGGTCTGTTGT CCACAG3' SEQ ID NO:6), antisense (5'ACTGTCCACATTACTAACTCTGAT3' SEQ ID NO:7).

Locus expansion PCR

Locus expansion PCR was developed as an alternative to inverse PCR because the success of the latter technique is dependent on the presence of appropriate restriction sites in the target DNA. In locus expansion PCR, however, a single primer is used to target a particular region of genomic DNA without prior restriction digestion. Standard primer extension was performed using Taq polymerase at 55° C. for 3 min. The single stranded cDNA was then recovered using Nick column chromatography (see modified SLIC procedure below). The recovered cDNA (15.4 μl) was then tagged at the 3' end with a homopolymeric tail of cytosine residues using 2.0 μl of terminal transferase (Pharmacia) in 2.2 μl of 10×phosphate buffer (Pharmacia) and 0.4 μl of 100 mM dGTP for 15 min at 37° C. and then inactivated at 75° C. for 10 min. After ethanol precipitation, these cDNAs were amplified by PCR using a sense primer that was complementary to the tail (5'ATAATGGTACCGGGGGGGGGGGGGG)3' SEQ ID NO:8 and a gene specific antisense primer that was upstream to the original primer used for the first extension reaction.

Cloning and Identification of PCR-Amplified DNA

PCR products were analyzed using agarose gel electrophoresis. Bands were excised and eluted by centrifugation through siliconized glass wool. The eluate was concentrated and purified by ethanol precipitation and then resuspended in distilled water.

Restriction selection for use in general cloning procedures

Initially most PCR products were cloned into a specially prepared pBluescript IISK+ vector called "T" vector to indicated that an extra thymidine was added at its 3' end to facilitate ligations (Marchuk et al., Nucl. Acids Res. 19:1154 (1990)). Restriction selection cloning was then developed because the existing methods were inefficient for cloning low abundance PCR products and for cloning DNA into reporter vectors that lack a gene for the selection of recombinants. It is well known that the ligation of two DNA fragments that are the product of digestion from different restriction enzymes will not lead to the regeneration of either of the original blunt or cohesive restriction sights. This property of sequence incompatibility of the original restriction enzyme can be exploited in a general cloning procedure for both PCR products and restricted DNAs.

Restriction selection cloning eliminates background by inactivating nonrecombinants containing regenerated blunt end restriction sites. There are two requirements for this technique to be of use. First, there must be a blunt end restriction site in the multiple cloning region of the vector and, secondly, this site must be different from the blunt end restriction site that was used to generate the insert. Standard ligation with T4 DNA Ligase is followed by inactivation of the ligase and digestion of the ligation mixture with the restriction enzyme that was originally used to linearize the vector. Thus, vectors containing an original restriction site will be cleaved prior to transformation while vectors that contain inserts will be resistant to digestion and will be cloned. Blunt end restriction sites were used for all cloning procedures discussed herein, but, compatible cohesive restriction sites can also be used for restriction selection.

The first step in a typical restriction selection cloning of PCR products or restriction fragments into plasmid vectors is the digestion of the vector (300 ng–500 ng) with an enzyme that produces blunt ends. The PCR product or restriction fragment to be inserted (1 μg of DNA) and the digested vector are then combined and precipitated together (this increases the total amount of DNA recovered after centrifugation). The DNA is precipitated (using 0.1 volume of 3 M NaOAc and 2.5 volumes of EtOH at −20° C.) and ligated overnight at 18° C. with 16U of Pharmacia T4 DNA ligase in 10×ligase buffer and 660 μM ATP (total volume of 20 μl). Following ligation, the enzyme is heat inactivated at 75° C. for 10 minutes. (It is crucial to completely inactivate T4 DNA ligase, as residual ligase activity may be confounded the subsequent restriction selection step. Residual ligase activity reverses the restriction enzyme-induced linearization of nonrecombinant vector DNA, preventing the selection of recombinants.) DNA is again precipitated from the ligation mixture and resuspended in 20 μl of digestion mixture for restriction selection. The digestion mixture contains 10 μl of the restriction enzyme, chosen for the restriction selection step, dissolved in 10×buffer. The reaction mixture is incubated overnight at the recommended temperature for the particular restriction enzyme used. Overnight incubation was found to be important because the number of nonrecombinants decreased with increasing incubation time. Enzyme is inactivated at 65° C. for 20 min or 85° C. for 30 min, depending on the enzyme used for restriction selection. DH5α cells (100 μl) are then transformed using 2.5 μl of the restriction digest.

Restriction selection is particularly useful when attempting to clone a trace amount of PCR product. For example, in one experiment RNA PCR was used to clone a region of the GABA$_A$ receptor β1 subunit gene. The PCR products could not be visualized by ethidium bromide staining but were identified by Southern analysis. The regions corresponding to the position of the bands in the autoradiogram were excised from the agarose gel and spun through siliconized glass wool at 6500 RPM for 20 minutes. The recovered DNA was then precipitated with the EcoRV digested pBluescript KSII+ vector and added to the ligation reaction.

In this experiment 6 out of 6 clones had inserts in them. In comparable experiments, no more than 2 out of 6 would have been expected to have inserts using the T vector method (Marchuk et al. 1990). In a typical experiment 80% of all clones restriction selected contained inserts. If the insert was in low abundance, the eluate obtained from a slice of agarose gel by centrifugation through silicon-coated glass wool was added directly into the ligation reaction mixture. Occasionally the percentage of recombinants was slightly less when the insert was very large or in low abundance. By using this procedure, with either the SmaI site or the EcoRV site in the KSII+ vector, PCR products have been cloned more efficiently than by using the T vector method, with which 25% of all clones contained inserts, and it was not necessary to prepare or purchase competent T vector (see Table 5).

In addition to the EcoRV and SmaI sites, pBluescript KSII+ vector contains BamHI, HincII, and XhoI sites that can be used with the restriction selection procedure. BamHI and XhoI produce cohesive ends that will ligate to compatible ends generated by other enzymes, but, as with blunt ends, will not regenerate the original restriction sites after ligation.

TABLE 5

Efficiency of cloning PCR products into general cloning vectors.

| Cloning Method | Percentage of colonies with inserts | Number of experiments |
| --- | --- | --- |
| restriction selection | 79.6% ± 7.8% | 5 |
| T vector | 25.4% ± 5.5% | 4 |
| blunt end | 1.25% ± 1.0% | 4 |

Three different methods (restriction selection, T vector, and standard blunt end cloning) were used to clone PCR products into pBluescript KSII+ vector. In 5 independent experiments, restriction selection cloning yielded the highest percentage of recombinants: 6 out of 6, 8 out of 12, 3 out of 5, 5 out of 10, and 4 out of 4 of the clones tested contained inserts.

Restriction selection cloning with vectors that lack a system for the identification of recombinant DNA The promoter activity of PCR products from the 5'-flanking region of the human β1 $GABA_A$ receptor subunit gene was investigated using the Promega Gene Light plasmids pGL2-Basic, pGL2-Promoter, and pGL2-Enhancer. The pGL2-Basic vector is designed to accept DNA fragments upstream or downstream of the luciferase reporter gene. The pGL2-Promoter vector is the pGL2-Basic vector containing an Sv40 Promoter in the 5'-end multiple cloning region. The pGL2-Promoter vector is designed to test the effects of potential enhancers cloned into the 3'-end multiple cloning region. The pGL2-Enhancer vector is the pGL2-Basic vector containing an Sv40 enhancer in the 3'-end multiple cloning region. The pGL2-Enhancer vector is used to examine the effects of DNA, containing potential promoter regions, cloned into the 5' multiple cloning region. Unfortunately, however, there was no efficient way to screen for recombinants using these vectors. The large size of the Gene Light luciferase vectors makes it extremely difficult to identify vectors with inserts by agarose gel electrophoresis.

Restriction selection was attempted using the blunt end SmaI restriction site which is present in the multiple cloning region of the pGL2-Basic and pGL2-Enhancer plasmids. For example, a PCR product of the human β1 gene (in a region of known sequence) was prepared from genomic DNA, purified by agarose gel electrophoresis, and ligated into the SmaI site of the pGL2-Basic vector. Minipreps of DNA (Promega Magic Minipreps), were digested with XhoI, which recognizes unique sites within the insert and the vector. The vector contains an XhoI site in the multiple cloning region that is 3' to the SmaI site. The 5' flanking region of the human β1 $GABA_A$ receptor gene contains an XhoI site at the 5' end. Therefore, digestion of the clone with XhoI will liberate the insert from the vector. In this experiment, 6 out of the 8 colonies tested contained the correct insert as confirmed by DNA sequencing. In similar experiments with different inserts, 6 out of 13, and 12 out of 12 colonies were found to contain vectors with the correct insert. From many such experiments, using different inserts in the pGL2 vectors, 75% of the colonies have been found to contain the appropriate inset, within error of the value obtained with pBluescript KSII+ vector (Table 1).

The design of new multiple cloning regions for use with restriction selection cloning The design of new multiple cloning regions containing additional blunt end and cohesive end restriction sites permits greater flexibility for the use of restriction selection cloning and for the production of deletional mutations of DNA inserted into pGL2 plasmids. The modified vectors were constructed according to the procedure shown in FIG. 1. Oligonucleotides were synthesized on an Applied Biosystems 392 Synthesizer using 5' phosphate-ON (Clonetech). As mentioned previously, the pGL2 series of reporter vectors contain the gene for firefly luciferase flanked by an upstream multiple cloning region that is used for promoter analysis, and a downstream multiple cloning region that is used for enhancer analysis. For promoter analysis, the multiple cloning region at the 5'-end of the luciferase gene was redesigned by inserting Fillers-1 and 2. Filler-1 was formed by annealing $^{5'}$GGTAC-CCCGCGGGCTAGCCTCGAGGCCCGGCCAGC TGTCGCGAA$^{3'}$ SEQ ID NO:9, and $^{340}$CCATGGGGCGC-CCGATCGGAGCTCCGGGCC CGGTCGACAGCGCT-TGCGC$^{5'}$ SEQ ID NO:10; and Filler-2 was formed by annealing $^{5'}$CGCGTGCGGCCGGAGCTCCCACCATG-GTGGA$^{3'}$ SEQ ID NO:11, and $^{3'}$ACGCCGGCCCTC-GAGGGTGGTACCACCTCTAG$^{5'}$ SEQ ID NO:12. The two complementary strands of the oligonucleotides were annealed according to the following procedure: 2.5 µg of sense oligonucleotide, 2.5 µg of antisense oligonucleotide, and 2.0 µl of annealing buffer (100 mM tris pH 7.5, 1 M NaCl), in atotla volume of 20 µl, were heated at 90° C. for 5 minutes; removed in the metal hot block and allowed to cool at room temperature for ~2 hrs. The complete modified multiple cloning region was then made by ligation of Filler-1 to Filler-2, leaving a 5' blunt end and a 3' cohesive end for directional cloning of the conjoined fillers into the "pGL2-Basic" and "pGL2-Enhancer" vectors (see FIG. 2 for the restriction site map of the complete multiple cloning region). For analysis of enhancer function, the multiple cloning region at the 3'-end of the luciferase gene was redesigned. The 3'-end multiple cloning region filler was formed by annealing $^{5'}$TCGACCCGCGGCGGCCGTACGTA CACGTGTGATCAACTAGTG$^{3'}$ SEQ ID NO:13, and $^{3'}$GGGCGCCGCCGGCATGCATGTGCACAC-TAGTTGATCACCTAG$^{5'}$ SEQ ID NO:14, leaving cohesive ends for directional cloning into the pGL2-Basic and pGL2-Promoter vectors (see FIG. 3 for the restriction site map of the multiple cloning region).

To construct the modified pGL2 vectors, 400 ng of the pGL2-Basic or pGL2-Enhancer plasmid was digested for three hours with SmaI and BglII to receive the conjoined Filler-1-Filler-2. 400 ng of pGL2-Basic or pGL2-Promoter vector was digested for three hours with SalI and BamHI to receive Filler-3, the redesigned enhancer-accepting multiple cloning region at the 3'-end of the luciferase gene. All of the reactions contained 5–10 units oe enzyme in a final volume of 20 µl. The restriction digest of the vector and the annealed oligonucleotides were then combined, ethanol precipitated, and resuspended in a final volume of 16 µl. 2 µl of T4 DNA ligase (16U) and 2 µl of 10×ligase buffer (containing 660 µM ATP) were then added and the tubes were incubated overnight at 18° C. 2.5 µl of the ligation mixture was added to 100 µl of competent DH5α cells and minipreps were screened for the presence of multiple cloning fillers by digestion with a restriction enzyme that recognized a unique site in the multiple cloning filler.

Figure 2:
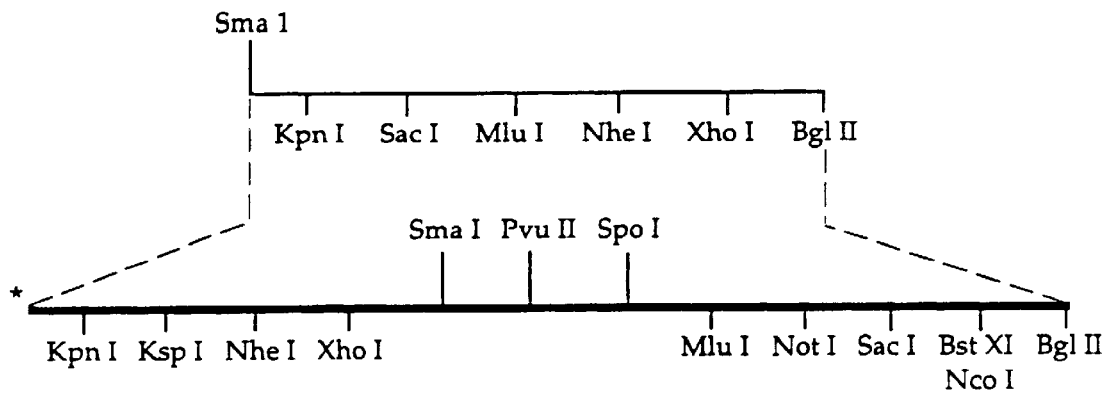
FIGS. 2 and 3 are schematic representations of multiple cloning regions.
Figure 3:
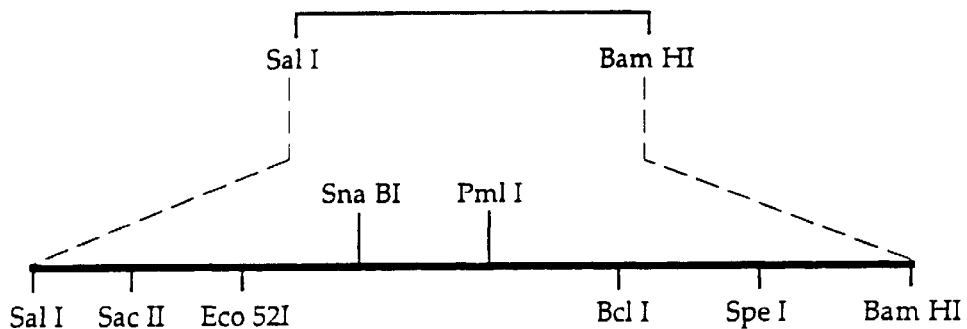

When performing restriction selection cloning using these modified pGL2 vectors, it is important to note that the SmaI site in the new filler can be used for cloning since ligation of the filler into the vector inactivated the original SmaI site (see FIG. 2). Deletional mutations are also now possible using the restriction sites in the new fillers because they were designed to contain cohesive sites positioned on either side of the blunt sites used for restriction selection. A site for a 3' overhang is positioned adjacent to each site that produces a 5' overhang. The 3' overhand protects the other end of the DNA molecule from nuclease digestion, allowing for re-ligation without the loss of vector sequence.

Primer Extension

Primer Extension was used to map the 5' ends of the β1 subunit mRNAs in order to determine the transcriptional start site of the β1 subunit gene. This new protocol using actinomycin D was chosen because it minimizes the production of primer artifacts which could interfere with the interpretation of the data. First an oligonucleotide antisense primer was made to a sequence that is 100 bp from the end of the mRNA. The primer was then end labeled using T4 polynucleotide kinase (2.5 μl H$_2$O, 1 μl of 10×T4 polynucleotide kinase buffer (0.5 M Tris-Cl, pH 8.0, 0.1 M MgCl$_2$, 50 mM DTT, 0.5 mg/ml BSA), 1 μl of 0.1 M DDT, 1 μl of 1 mM spermidine, 1 μl of 50–100 ng/μl primer, 3 μl 10 μCi/ul [γ$^{32}$P] ATP, and 0.5 μl 20–30 U/μl T4 polynucleotide kinase for 1 hr at 37° C.). The reaction was stopped by the addition of 2 μl of 0.5 M EDTA and 50 μl of TE buffer (10 mM Tris, 1 mM EDTA). The oligonucleotide was then purified by three rounds of ethanol precipitation using 2 M ammonium acetate. 10–50 μg of total human RNA was then mixed with 5×10$^4$ CPM of the radio labeled primer and 1.5 μl of 10×hybridization buffer (1.5 M KC, 0.1 M Tris-Cl, pH 8.0, 10 mM EDTA). The tubes were sealed with parafilm and incubated at 65° C. for 90 min. Tubes were then removed and left on the bench until they reached room temperature. To each reaction was added 0.9 μl of 1M Tris-Cl, pH 8.0, 0.9 μl of 0.5 M Mg Cl$_2$, 0.25 μl of 1M DTT, (6.75 μl of 1 mg/ml actinomycin D, 1.33 μl of 5 mM 4dNTP mix, 20 μl of dH$_2$O, and 0.5 μl of 18U/μl AMV reverse transcriptase. The samples were then incubated for 1 hr at 42° C. To degrade the template RNA, 105 μl of RNase, reaction buffer (100 μg/ml salmon sperm DNA and 20 μg/ml RNase A) was added and incubated at 37° C. for 15 min. The DNA was then ethanol precipitated, washing once with 70% cold ethanol, desiccated and resuspended in 5 μl of formamide loading buffer. The samples, along with dideoxy sequencing reactions (used to determine the size of the primer extension products) were resolved on a 6% sequencing gel.

S1 nuclease protection

S1 nuclease protection was performed according to established protocol (Maniatus et al., 1991).

Modified SLIC procedure

The rapid amplification of complementary ends (RACE) procedure (Frohman et al., 1988) was developed for the purpose of recovering the 5' ends of mRNAs in order to determine the transcriptional initiation site of a particular gene.

Unfortunately RACE fails in many instances, particularly where it is important to recover the cDNAs of rare copy mRNAs. A later modification of RACE, single stranded ligation of sscDNAs (SLIC), Dumas et al., Nuc. Acids Res. 19:5227–5232 (1991)), was developed to enhance recovery. In SLIC a primer, called the ligation primer, is ligated to the 3' end of the cDNA using RNA ligase. A sense copy of this primer is then used with the gene specific antisense primer in standard PCR. Although SLIC has a greater chance of succeeding than RACE, the SLIC procedure suffers from the problem that it is extremely difficult to remove the excess primer used in the ligation reaction before doing PCR. This excess primer can then hybridize to artifactual PCR products leading to the preferential amplification of small artifactual products over the cDNA target of interest.

A modified version of the SLIC was used herein procedure, to remove the possibility of generating artifacts from excess ligation primers, and this modification successfully recovered the 5' ends of the β1 subunit mRNAs. This modification involved the synthesis of a specially prepared ligation primer that contains an amino group at its 3' end. This amino group prevents the excess ligation primer from initiating a polymerase extension reaction. Standard PCR was performed as described. PCR products were identified by agarose gel electrophoresis and cloned into pBluescript KSII+ vector using restriction selection cloning. Recombinants containing the relevant insert were identified by Southern analysis and sequenced for verification and analysis.

EXAMPLE 3

Characterization of the 5' Flanking Region of the Human β1 Subunit Gene

3A. Identification of the 5' flanking region using PCR based genomic walking techniques.

Briefly, an antisense primer complementary to the 5' end of the gene was used to prepare a single stranded copy of a region of DNA upstream to the primer sequence. The 3' end of the primer extended DNA was then tailed by the addition of a homopolymer using terminal transferase. PCR was performed using a sense primer complementary to the tail on the 3' end of the primer extended DNA, and an antisense primer complementary to the 5' end of the gene. A 112 bp PCR product was obtained, cloned into the pBluescript KSII+ using restriction selection cloning, and sequenced. Inverse PCR was performed using the same antisense primer and a new sense primer that contained coding sequence from the Hβ1 cDNA. The inverse PCR product obtained was cloned, sequenced, and compared with the product obtained by locus expansion PCR revealing a region of overlapping sequence. Although a number of different restriction enzymes were used to produce fragments of human genomic DNA for templates in inverse PCR, the majority of inverse PCR products contained only 20 to 50 bp of additional upstream sequence. Inverse PCR products produced from MspI digested genomic DNA, however, were found to contain an additional 473 bp of new sequence.

In order to verify that the apparently contiguous PCR products generated using genomic walking techniques were from the human β1 subunit gene, PCR was performed using a set of flanking primers. The sense primer contained the most 5' end of the new upstream sequence and the antisense primer contained sequence within exon 1 (from −10 to +14 of the Hβ1 cDNA) (see FIG. 4). PCR with these primers produced a 541 bp product (PCR541). Southern analysis and sequencing revealed that PCR541 exhibited sequence identity with the first 56 bp of the Hβ1 cDNA. Sequencing of a larger PCR product that spanned PCR541, exon 1, intron 1 and exon 2 demonstrated that PCR541 was upstream of the coding region for the mature β1 subunit.

3B. Mapping of the transcriptional start sites

PCR541 was found to contain 496 bp of nucleotide sequence upstream to the 5' end of the published "full length" Hβ1 cDNA. Surprisingly, results of S1 nuclease protection, primer extension, and modified SLIC revealed multiple potential start sites that are positioned downstream to the end of the published human β1 cDNA.

To determine the location of the transcriptional start site for the Hβ1 cDNA, a second round of modified SLIC was performed using an antisense primer that contained sequence upstream to the most 5' end of the first SLIC products.

Four new start sites were revealed after the second round of modified SLIC. All of these start sites were positioned upstream to the 5' end of the published Hβ1 cDNA. All of the start sites that were mapped with modified SLIC begin with an A which suggests that they represent the true ends of β1 subunit mRNAs, since greater than 50% of the mRNAs characterized to date have been found to be initiated at an A (Darnell et al., *Molecular Cell Biology*. Scientific American Books, WIHI Freeman and Co., New York (1990)). Four transcriptional start sites positioned at +1, +7, +15, and +33, which are upstream to the end of the Hβ1 cDNA, would produce a transcript that codes for a signal peptide of 26 amino acids using the ATG at +92 (FIG. 7). An additional four sites, located at +82, +84, +88, and +91, could also produce a transcript that codes for a 26 amino acid signal peptide. Such transcripts would, however, contain a very small, up to 10 bp, untranslated region. In addition, three of the seven start sites mapped to exon 1 were located at +93, +112, and +116 within the signal peptide sequence and 27 bp upstream of an ATG translational start codon at +143 (FIG. 7). The activation of these transcriptional start sites would be expected to produce a transcript that codes for a 9 amino acid signal peptide. There are three potential translational start codons and all conform to Kozak's rule for eukaryotic initiation sites (Kozak, 1984), containing an A or G three nucleotides upstream from the AUG triplet. However, only the region around the ATG at +152, UUAACCAUGG SEQ ID NO:15, yielded a close match to the consensus sequence for a eukaryotic initiation site CCA/GCCAUGG, consistent with a 6 amino acid signal peptide. Nevertheless, signal peptides range from 15 to 32 amino acids in length, favoring the ATG at +92 as the translational start codon. This is consistent with the observation that the most prevalent transcriptional initiation site observed by modified SLIC coincided with the most upstream translation initiation site (TRN INIT).

3C. Sequence analysis of PCR541 reveals consensus sequences for promoter and enhancer elements Having located the possible transcriptional initiation sites for the human β1 gene, the sequence contained within PCR541 was then analyzed to determine if there were any TATA-like boxes that were positioned appropriately upstream of the initiation sites. Three of these start sites are positioned downstream from the TATA-like box at a distance that is within the range for promoter function (Xu et al., 1991). There is also an AT rich region at −58 that resembles an inverted TATA-like box. However, this TATA-like box may be positioned too far away from the start sites at +1, +7, +15 and +33 for activity (Xu et al., 1991). Interestingly, an A rich region at −245 is flanked by two CAAT boxes located at −203 and −295 respectively. A small GC rich region 5' to the A rich region is similar to the one found near many TATA-like box promoters (see Lewin, *Genes III*. John Wiley and Sons, Inc., (1990)). However, no transcriptional start sites have been mapped to this region of PCR541.

The sequence of the 5'-flanking region was analyzed using MacVector and MatInspector (http://www.gsf.de/cgi-bin/matsearch.pl) to determine if there were any canonical upstream regulatory elements. There are consensus sequences for AP1, SP1, and GRE elements; TATA-, CAAT-, and CACCC-boxes; as well as AA-control elements which are similar to those found in the regulatory regions of genes coding for enzymes involved in the biosynthetic pathway of amino acids (Hinnebusch, et al., 1993). Two of three AP1 sites are found on the negative strand at +37 (TTAAGTCG) and −127 (GTAAGTCA), the latter sharing sequence with the AA-control element at −133.

A TATA box at +76 is positioned upstream from five start sites of which only three are within range for promoter function (Xu, et al., 1991). An inverted TATA-like box is located at −58 but it is positioned more than 35 bp upstream of the start sites at +1, +7, +15 and +33. Site directed mutagenesis of the inverted TATA box (AATATT to AACATG) is without effect, demonstrating that the promoter driving the major start site is TATA-less.

Surprisingly, we found four initiator (Inr) sequence; that are associated, collectively, with eight of the eleven mapped transcriptional start sites. An AP1 site that is located on both the positive and negative strands at +76 (+, TTAATCA; −, TGATTAA) shares sequence with the TATA box at +73 as well as the 5' end of an Inr. Two other AP1 sites are adjacent to or overlapping with Inr sequences (FIG. 7). Similarly, there is a site for the human CAP binding protein that overlaps with the Inr at −2.

A GRE element overlaps the motif AGGAGATGGAGC SEQ ID NO:16 (−110 to −122), which is found in the 5' flanking regions of neural-selective genes such as at −50 to −39 in the rat type II sodium channel gene (Maue, et al., 1990). Other regulatory sequences include the binding sites for proteins that bend DNA (SRY and Helix Fork Helix 2) at −222, the Ebox at −172, the insulin enhancer core motif at −150 that overlaps with an AP4 site, the Octamer 1 site at −48, the delta EF1 repressor at −31, the homeobox Deformed (DFD) site at +71, and the heat shock protein sites HSF1 and HSF3 at +22 and +54 respectively.

EXAMPLE 4

Functional Analysis of the 5' Flanking Region of the Human β Subunit Gene Reveals Promoter and Enhancer Activities Primary cell culture Chicken The brains of seven day old chick embryos (13–15 brains) were dissociated and maintained in primary monolayer cultures. Brain tissue was dissected on ice and maintained in Puck's $D_1G$ (285 mM NaCl, 111 mM KCL, 220 µM $Na_2HPO_4$, 220 µM $KH_2PO_4$, 2.8 µM phenol red, 20 µM NaOH, 344 µM streptomycin, 200 U/ml penicillin and 0.1% glucose). After removal of the meninges, the tissue was minced into small pieces and then treated with 0.025% trypsin (GIBCO) for 5 min in Pucks $D_1G$. Neurons were then separated from the trypsin-containing buffer by centrifugation (150×g, 5 min, RT) and resuspended in plating medium (Eagle's Minimal Essential Medium supplemented with 10% heat inactivated horse serum, 5% chick embryo extract, 2.4 mM glutamine, 100 units/ml penicillin, and 100 mg/ml streptomycin). The cells were then triturated through a fire-polished Pasteur pipette and added to 150 ml of plating medium. This medium was then aliquoted into fifteen collagen-coated plastic 100 mm dishes (10 ml/dish). Cultures were maintained at 37° C. in 5% $CO_2$. Cytosine arabinoside (ARA-C, 1 µM final concentration) was added one day after plating to control the growth of non-neuronal cells. Two days later the medium was replaced with growth medium (same as previously described except for the addition of added glucose at 22 mM and chick embryo extract at 2.5%). Primary chick brain cultures were used after 7 days for chronic treatment studies and transfection assays.

Rat primary cell culture 18-day-old rat embryos were used for all dissections. Each adult female rat produced 12–15 embryos. After removal from the uterus, hind limbs were collected and placed into a 60 mm tissue culture dish that contained 4 mls of CMF buffer ($Ca^{2+}/Mg^{2+}$ free Hank's BSS, 4.2 mM bicarbonate, 1 mM pyruvate, 20 mM Hepes, and 3 mg/ml BSA, pH. 7.25–7.30) and kept on ice for the plating of muscle and fibroblast cultures. Hippocampi were dissected and placed into a 35 mm tissue culture dish containing 2 ml of CMF. The rest of the cortex (after removal of diencephalon and surrounding subcortical nervous tissue) was transferred to a 60 mm tissue culture dish containing 4 mls of CMF.

The hippocampi were then transferred to a 15 ml sterile centrifuge tube, triturated 20 times with a 5 ml sterile plastic pipette, and centrifuged at 200×g for 5 min. After removing the supernatant, the pellet was resuspended in 5 ml of defined medium (10% FBS DMEM-DM, see Table 6). The cell suspension was triturated another 20 times with a 5 ml sterile plastic pipette and added to 31 ml of fresh 10% FBS DMEM-DM. The diluted cell suspension was then distributed into three NUNC 6 well 35 mm poly-D-lysine coated tissue culture plates (2 ml/dish).

The neocortical tissue in CMF was minced into small pieces, transferred to a 15 ml sterile centrifuge tube, triturated and processed for plating as described above (except that the pellet was resuspended in 8 ml of medium and after the second trituration, 3 ml of the cell suspension was diluted into 97 ml of medium and plated. 96 mls were then distributed into eight 6 well NUNC 35 mm poly-D-lysine coated tissue culture plates and the rest of the solution was discarded.

The hind limbs in CMF were minced and then centrifuged for 5 min at 200×g. The supernatant was removed and replaced wild fresh CMF containing 0.25% trypsin. After the pellet was resuspended, the solution was treated for 7 min at 37° C. and pipetted up and down to dissociated clumps of tissue. An equal amount of 10% FBS DMEM-DM was added to the tube which was then centrifuged at 200×g for 5 min. The supernatant was then removed and the pellet was resuspended in 5 ml of fresh 10% FBS DMEM-DM and triturated. 3 ml of the cell suspension was diluted into 97 ml of 10% FBS DMEM-DM and plated into eight 6 well NUNC 35 mm poly-D-lysine coated tissue culture plates or ten 100 mm NUNV poly-D-lysine coated dishes.

Hippocampi, neocortex, and fibroblast/muscle mixed cultures were then incubated at 37° C. in 5% $CO_2$. After 30 medium the mecum from the hind limb (mixed fibroblast/muscle) cultures was removed (this medium was then replated to produce cultures enriched with muscle cells) and replaced with fresh medium to favor the proliferation of fibroblast over muscle cells. 24 hours later these fibroblast cultures were passaged and used the following day for transfection assays. The cultures enriched for muscle cells were allowed to grow for 48 hours prior to transfection. ARA-C was added to hippocampal and neocortical cultures two days after plating to control the growth of non-neuronal cells. The ARA-C was removed after two days and replaced with serum free DMEM-DM. Hippocampal and neocortical primary cell cultures were used for chronic treatment and transfection studies after 7 days in culture.

Transfection assays

Primary cell cultures were transfected using the calcium phosphate technique. 35 µg of DNA were added to a solution containing 0.25 M $CaCl_2$ in a final volume of 500 µl. This solution was then added dropwise under oxygenation to 500 µl of 2×Hepes buffered saline solution. After sitting for 30 min at room temperature, the mixture was vortexed and 200 µl aliquots were added dropwise to each 35 mm tissue culture dish or the entire mixture, 1 ml, was added dropwise to each 100 mm dish. The following two reporter vectors were used to clone the various fragments of the β1 gene upstream of the gene for firefly luciferase: the modified pGL2-Basic that contains the enhancer filler (referred to as

TABLE 6

Media preparation for the culturing of primary neocortical and hippocampal neurons.

| Dulbecco's Modified Earles Medium (DMEM) 1x | 10% FBS DMEM Defined Medium (DM) | Serum-Free DMEM Defined Medium (DM) |
|---|---|---|
| DMEM: 1 packet (Gibco #430-2100EB) | Water-based DM1 (1.0 ml) | Water-based DM1 (1.0 ml) |
| 26.2 mM Bicarbonate (2.2 g) | Ethanol-based DM2 (0.1 ml) | Ethanol-based DM2 (0.1 ml) |
| 1 mM Pyruvate (0.110 g) | 100 µU/ml Penicillin | 100 µU/ml Penicillin |
| 20 mM Hepes (4.76 g) | 100 µg/ml streptomycin | 100 µg/ml streptomyctn |
| $dH_2O$ to 1000 ml | 2.4 mg/ml BSA | DMEM 1 × 97.9 ml |
| | Fetal Bovine Serum 10 ml | |
| | DMEM 1 × 86.9 ml | |
| Total: 1000 ml | Total 100 ml | Total 100 ml |

| Water-Based DM1 (All compounds purchased from (Sigma) | | Ethanol-Based DM2 (All compounds purchased from Sigma) | |
|---|---|---|---|
| Compound | Weight | Compound | Weight |
| Insulin | 25 mg | Corticosterone | 0.105 mg |
| Triiodothyronine | .01 mg | Progesterone | 0.0315 mg |
| Biotin | 0.5 mg | Retinol acetate | 0.5 mg |
| BSA | 500 mg | Linoleic acid | 5 mg |
| Transferrin | 25 mg | Linoleic acid | 5 mg |
| Vitamin B12 | 1.7 mg | Retinol | 41 mg |
| Carnitine | 10 mg | Vitamin E | 5 mg |
| Ethanolamine | 5 mg | Vitamin E Acetate | 5 mg |
| Galactose | 75 mg | | |
| Putrescine | 80 mg | 100% ETOH | Total volume: 5 ml ETOH |
| Selenite, Na | 0.026 mg | | |
| Total Volume: 50 ml | | | | pGLef), which contains no promoter or enhancer and pGL2-Enhancer (referred to as pGLSvE), which contains the Sv40 enhancer with no promoter. The following five vectors were used for monitoring the efficiency of transfection: positive controls, pGL2-Promoter (pGL-SvP) which contains the Sv40 promoter, pGL2-Control (pGL-SvPSvE) which contains the Sv40 promoter and enhancer, and pSVβgal, which contains the Sv40 promoter and enhancer upstream of the β-galactosidase gene; negative controls, pGLSvE and pGLef as described above.

16 hours after transfection, cells were washed two times in buffered saline solution (37° C.) and then lysed by the addition of either 100 μl (35 mm dishes) or 500 μl (100 mm dishes) of lysis buffer (25 mM Tris-HCl, pH 7.5; 10 mM EDTA, 15% sucrose, and 2 mg/ml lysozyme). After 15 minutes, cells were scraped using a rubber policeman and transferred to an Eppendorf tube. The cellular debris was pelleted and discarded while the supernatant was transferred to a fresh tube and this extract was used for the luciferase or both luciferase and βgalactosidase assays. In assays where co-transfection was performed, cells were lysed with a special lysis buffer from Promega that permits both luciferase and βgalactosidase activity to be monitored using samples taken from the same extract. For in situ βgalactosidase staining, the cells were not lysed but instead rinsed with an acetone/methanol 1:1 mixture and incubated at 37° C. with staining solution (5 mM $K_3Fe$ ($CN_6$), 5 mM $K_4Fe$ ($CN_6$), 2 mM $MgCl_2$, in phosphate buffered saline). Protein assays were performed on all samples according to the method of Lowry (Lowry et al., 1951). For luciferase assays, 20 μl of the cell extract was mixed with 100 μl of luciferase assay reagent and monitored in a Beckman scintillation counter.

4A. PCR 541 exhibits promoter and enhancer activity in transfected primary neuronal cultures.

Figure 8:
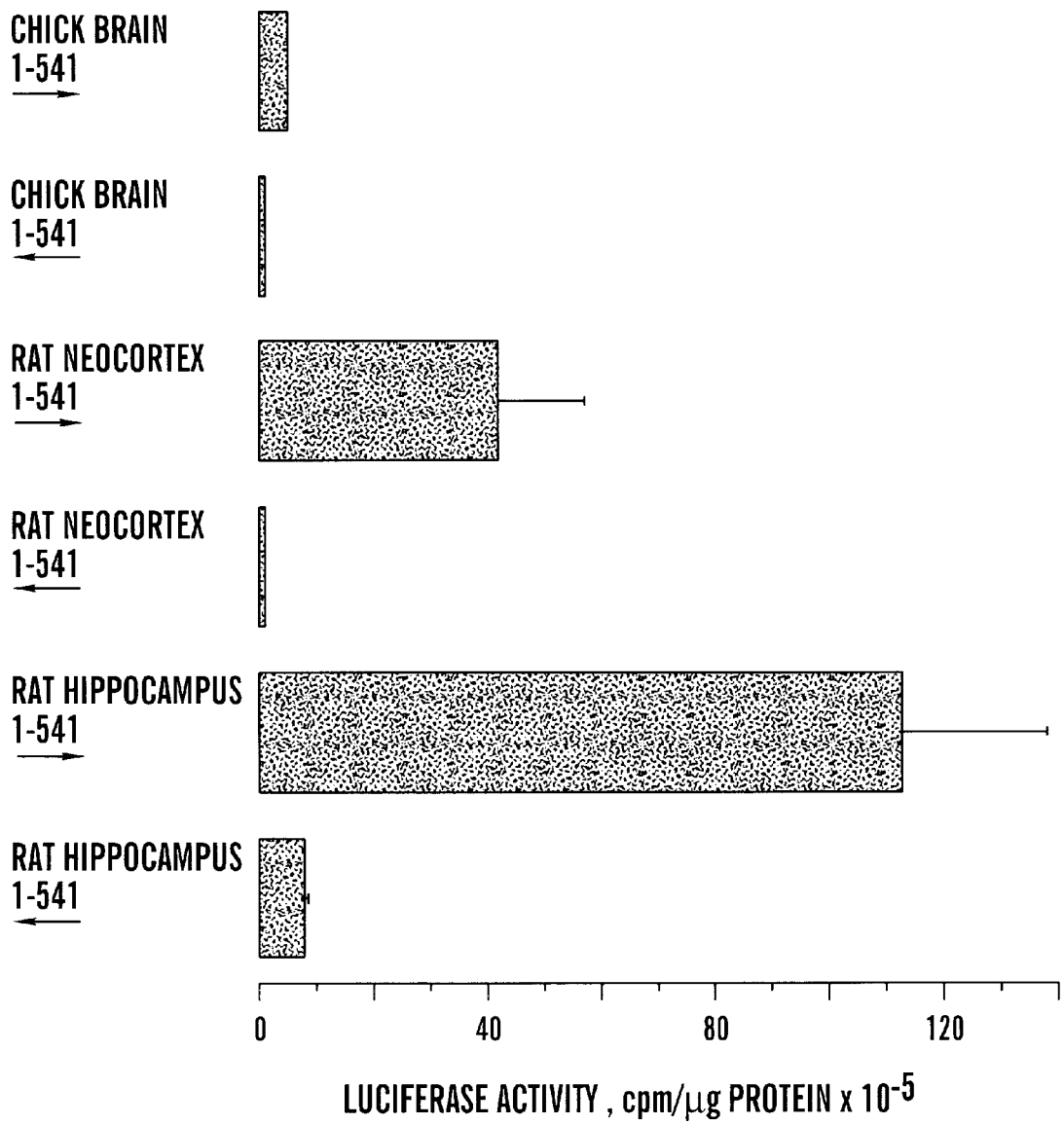
FIG. 8 contains data which demonstrate that PCR541 exhibits orientation specific promoter activity in transfected neuronal cultures of chick brain, rat neocortex, and rat hippocampus which were transfected with a reporter construct that contained PCR541, in either a forward (→) or reverse (←) orientation, upstream to the gene for firefly luciferase.

Primary cultures of dissociated chick brain, rat neocortex, and rat hippocampus were transfected with a luciferase construct (pGLef-541) that contained PCR541 in either a forward or reverse orientation. FIG. 8 shows promoter activity measured as luciferase expression by the transfected cultures. The data represent the means ± standard errors of n independent experiments in primary cultures of chick brain (forward orientation, n=5; reverse orientation, n=3), rat neocortex (forward orientation, n=11; reverse orientation, n=3) and rat hippocampus (forward orientation, n=7; reverse orientation, n=3). Activity is expressed relative to the amount of cellular protein. All of the transfected cultures displayed promoter activity that was orientation specific (FIG. 8). Correction for background luciferase activity was achieved by transfection with pGLef, a luciferase vector that lacked a promoter region upstream of the luciferase gene. Primary cultures transfected with pGLef-541 displayed luciferase activity that was significantly greater than that of cultures transfected with pGLef (chick brain, 23-fold greater, rat neocortex, 104-fold greater; and rat hippocampus, 353-fold greater).

Figure 9A:
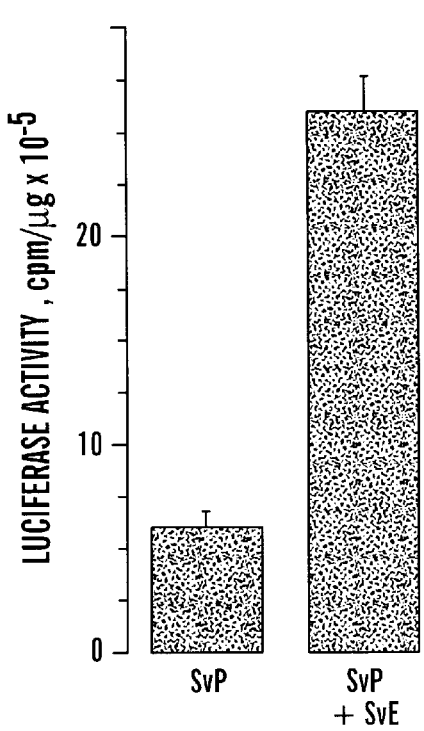
FIGS. 9A–D show data which demonstrate that the Sv40 enhancer stimulates the activity of the Sv40 promoter but not the activity of PCR541 in primary cultures of chick brain which were transfected with either pGL-Sv40 or pGL-Sv40SvE. Expression level is shown in FIG. 9A. P indicates the presence of the Sv40 promoter. P+E indicates the presence of the Sv40 promoter and the Sv40 enhancer.
Figure 9B:
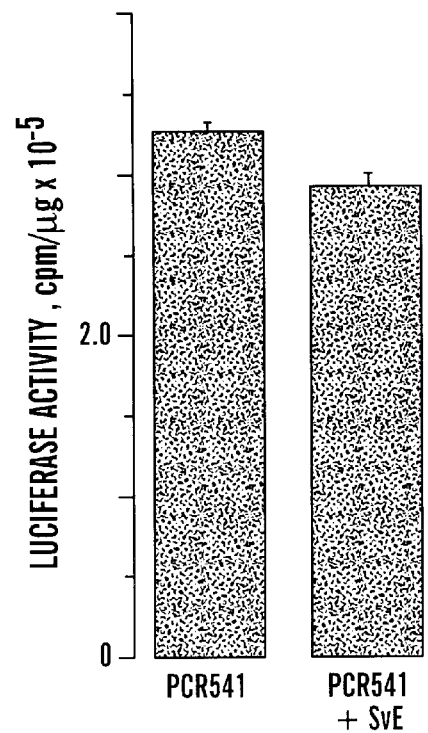
Figure 9C:
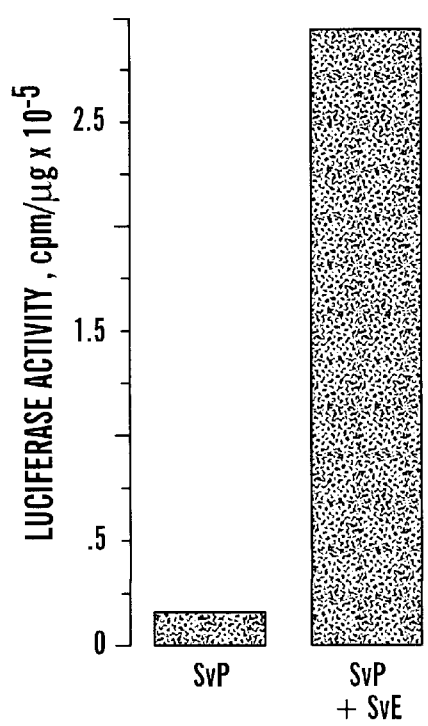
Figure 9D:
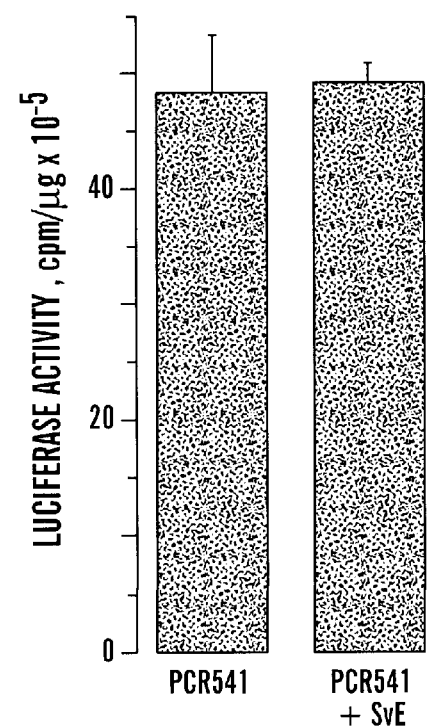

To characterize the activity of the promoter within PCR541, the Sv40 enhancer was cloned downstream of the luciferase gene in pGLef-541, producing pGLef-541SvE. Since the Sv40 enhancer is known to stimulate the activity of all previously tested promoters, addition of the Sv40 enhancer would be expected to stimulate the activity of the promoter within PCR541. Control transfections demonstrate that the Sv40 promoter and enhancer were active in transfected primary cultures of dissociated chick brain and rat neocortex. Primary cultures were transfected with the luciferase vector pGL-SvP that contained the Sv40 promoter upstream of the luciferase gene, and related vector pGL-SvPSvE that also contained the Sv40 enhancer downstream of the luciferase gene. FIGS. 9A and C show the results of these transfections. Data represent the means ± standard errors of a representative experiment in which two dishes were used for each determination. Activity is expressed relative to the amount of protein. The addition of the Sv40 enhancer to pGL-SvP substantially increased promoter activity as measured by cpm/μg of luciferase activity. Cultures transfected with either pGL-SvP or pGL-SvPSvE displayed luciferase activity that was significantly greater than that of cultures transfected with pGLef (chick brain: pGL-SvP, 94.5 fold greater and pGL-SvPSvE, 487-fold greater; rat neocortex: pGL-SvP, 3.4-fold greater and pG1-SvPSvE, 34-fold greater) in three independent experiments for each culture condition. Surprisingly, when primary chick brain and rat neocortical cultures were transfected with pGLef-541 and pGLef-541SvE (FIGS. 9B and D) there was no significant difference in the levels of luciferase activity between the cultures. This observation suggests that PCR541 already possesses an enhancer and that this enhancer contributes to the fully active state of the human β1 promoter.

4B. Mapping of the promoter activity in PCR541.

Figure 14A:
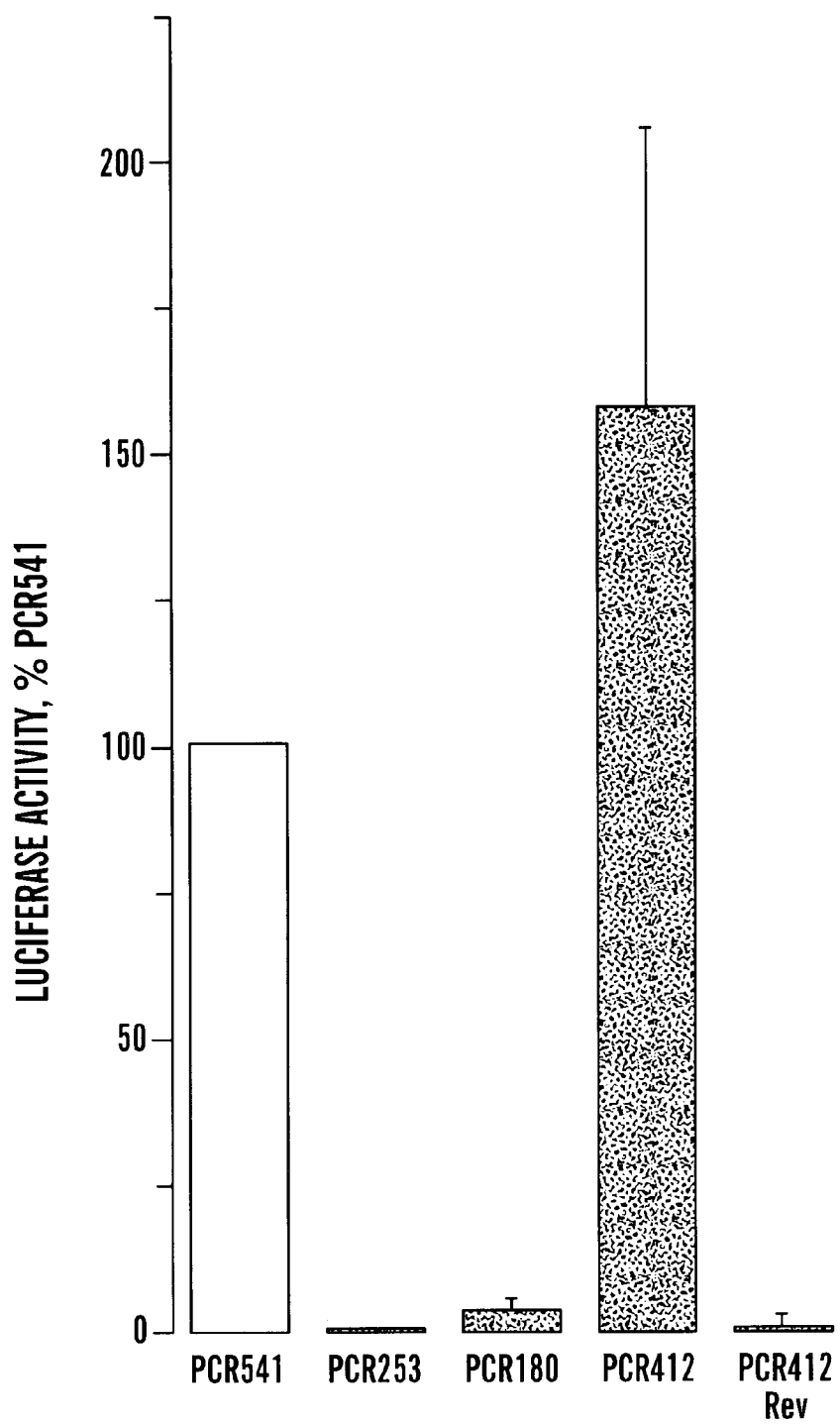

PCR was used to obtain individual segments of the human β1 gene contained within PCR541. Primary cultures of rat neocortex were transfected with different luciferase constructs that contained segments of PCR541. (see FIGS. 10–12). The data represent the mean luciferase activity ± standard error of three independent experiments with at least 2 different preparations of DNA. Activity was normalized by the amount of protein in each reporter assay before being displayed as % control, where control is the activity from cultures transfected with pGLef-541 (white bar). Reverse orientation is indicated by Rev. Correspondence of the position of these PCR products with PCR541 is shown in FIG. 7. When primary cultures of rat neocortex were transfected with the luciferase construct pGLef-253 that contained the first 253 bp of PCR541 (PCR253, +105 to −148) luciferase activity was not significantly greater than that of cultures transfected with pGLef (FIG. 14A). Similarly, when primary cultures were transfected with the luciferase construct pGLef-180 that contained the next upstream 180 bp of PCR541 (PCR180, −128 to 307) there was little or no promoter activity. Transfection of the 412 bp segment (PCR412), containing both PCR253 and PCR180, produced luciferase activity that was equal to or greater than the activity of PCR541. As can be seen in FIG. 14A, the promoter activity of PCR412 was orientation specific.

4C. Addition of the SV40 enhancer to KPGLEF-253 produces promoter activity in primary cultures.

Figure 13:
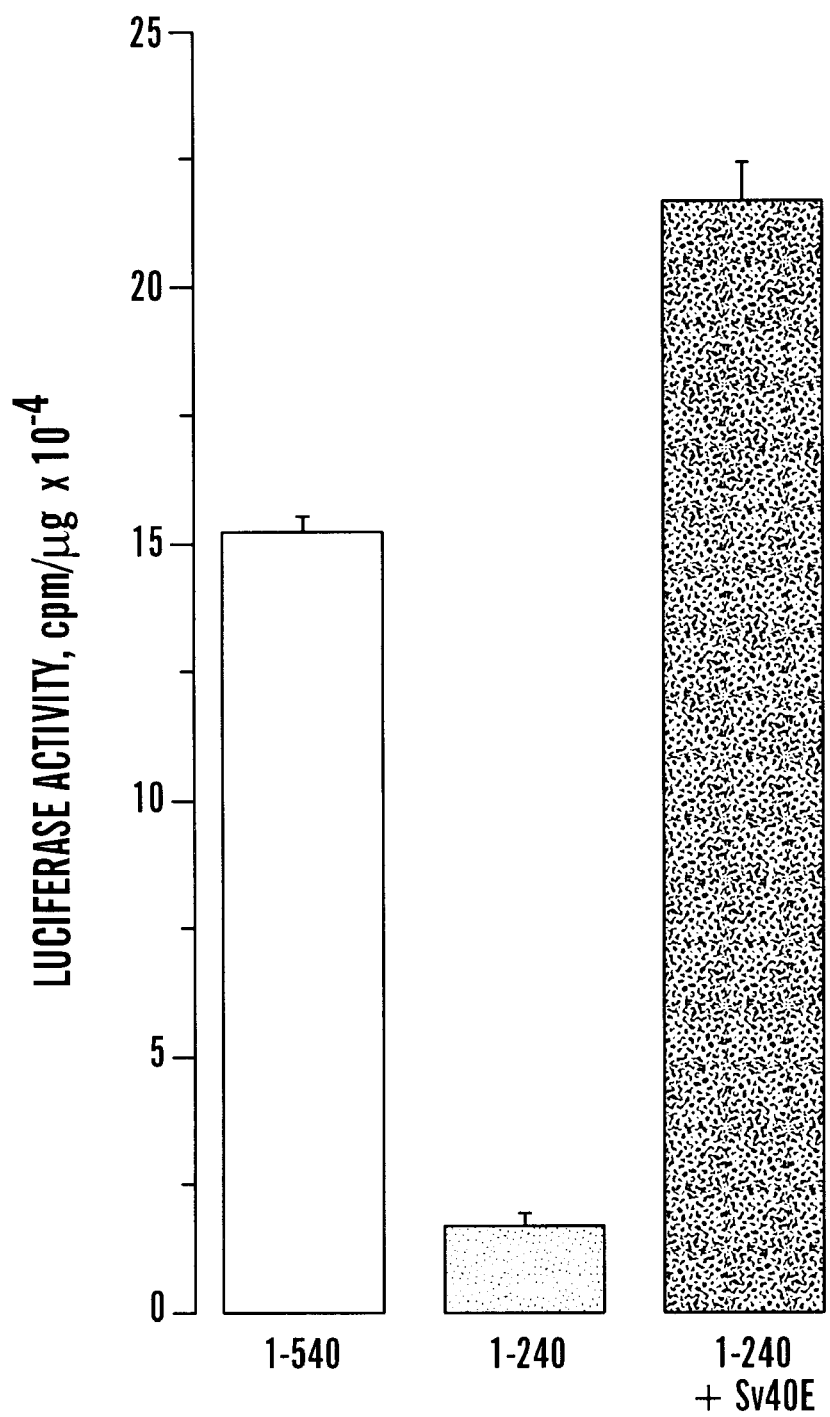
FIGS. 13 and 14A–B shows an analysis of promoter activity within the 5' flanking region of the human β1 gene.

To determine whether PCR253 contained an active RNA polymerase binding site and an appropriately positioned transcriptional initiation site (i.e., a promoter), primary cultures of rat fibroblast were transfected with the luciferase construct pGLef-253 and a related vector pGL-253SvE that contained the Sv40 enhancer downstream of the luciferase gene. FIG. 13 shows luciferase activity of primary of rat fibroblast transfected with either pGLef-253 or pGLef-253SvE. The data represent the means ± standard errors of 2 independent experiments with two different preparations of DNA. Activity was normalized by the amount of protein in each reporter assay. +SvE is used to indicate the presence of the Sv40 enhancer, The Sv40 promoter and enhancer were extremely active in primary cultures of rat fibroblast, inducing a 2159-fold increase in luciferase activity with respect to cultures transfected with pGLef. As can be seen in FIG. 13, the Sv40 enhancer increases luciferase activity when positioned downstream of the luciferase gene in pGL-253SvE. Transfection of neocortical (cultures with pGLef-253SvE also produced luciferase activity that was significantly greater than the activity from cultures transfected with pGLef(127%±65% (n=3)). The variability in the data from neocortical cultures may reflect the fact that the activity of the Sv40 promoter and enhancer is much weaker in transfected brain cultures as compared to fibroblast or muscle.

4D. Deletional analysis of the core promoter

Figure 11:
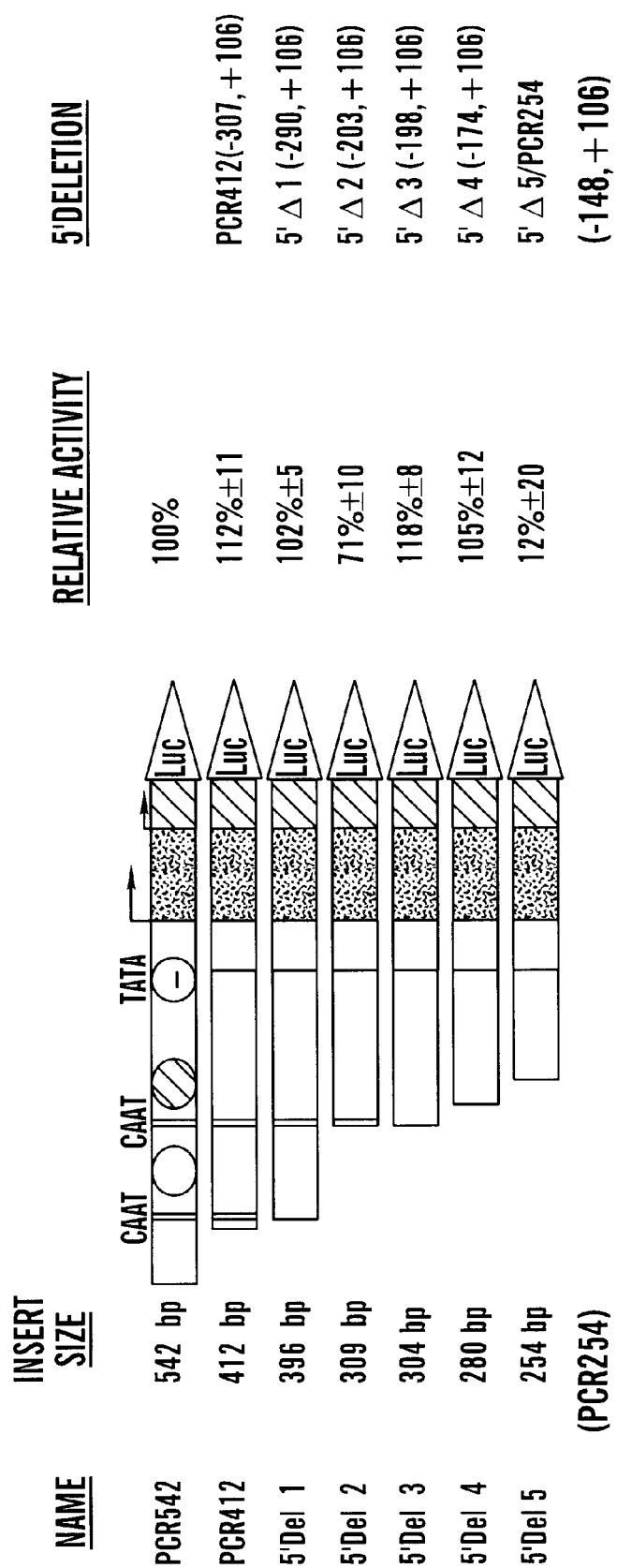

FIGS. 10–12 shows that the core promoter region of the β1 promoter is revealed by deletional analysis. In order to identify active transcriptional initiation sites within the 5' flanking region of the β1 gene, PCR was performed with various antisense primers to produce 3' deletions of PCR541, 3'DEL1–4 (FIG. 11). Promoter activity from transfection of the 3' deleted fragments into hippocampal cultures is displayed as % activity of PCR541, which is set at 100. Promoter activity driven by the deleted fragments is also compared to that of PCR412, PCR180 and PCR253 for reference (FIG. 10). Activity was normalized by the amount of protein in each reporter assay. The data represent the means ± standard errors of 3 independent experiments. In order to identify the enhancer region within PCR180, PCR was performed with various sense primers to produce 5' deletions of PCR541, 5'DEL1–4 (FIG. 12). Promoter activity from transfection of the 5' deleted fragments into hippocampal cultures is displayed as % 5'DEL1, which is set at 100. 5'DEL1 contains a deletion that removes that first CAAT-box in PCR541. Promoter activity driven by the deleted fragments is also compared to that of PCR253 for reference. Activity was normalized by the amount of protein in each reporter assay. The data represent the means ± standard errors of 3 independent experiments.

Because there are a number of transcriptional initiation sites that have been mapped to the human β1 gene, we used functional analysis to determine the active site(s) in our system. PCR was used to produce fragments of PCR412 that contained 3' deletion. In FIG. 11 the results show that removal of the most 3' initiation sites, which generates a 378 bp fragment, reduces the activity by ~50%. Removal of the most 5' initiation sites generates a 304 bp fragment with little or no promoter activity. Interestingly, with an additional loss of 3' sequence that contains a possible reverse TATA box (positioned at −58), luciferase activity increases to ~50% of that of the control PCR412. When only the TATA box sequence at −58 is added back to this DNA fragment, promoter activity drops to background. As described above, PCR180 which contains a large 3' deletion is also without promoter activity. These results suggest that the TATA box at −58 is active and may serve an important function to fix the position of the RNA polymerase binding site even though removal may uncover a possible cryptic promoter with significant activity.

In parallel to our 3' deletion studies, we generated a set of DNA fragments containing different 5' deletions of PCR541. These experiments were designed to identify regulatory sequences within PCR180 that were responsible for the activation of the β1 promoter. Removal of the first CAAT box sequence in PCR412 (5'DEL1) produces no change in the overall level of β1 promoter activity and so all activity from subsequent 5' deletions is compared to the activity driven by 5'DEL1. The loss of 87 bp of sequence from 5'DEL1 reduces activity by ~29% (5'DEL2, see FIG. 12). Removal of the second CAAT box (5'DEL3), however, increases promoter activity by as much as 47% when compared to the activity of 5'DEL2. The additional loss of 24 bp of sequence from 5'DEL3, generating 5'DEL4, produces luciferase activity that is equal to the activity of PCR541. This observation is informative because PCR253 has low activity that is not orientation specific and 5'DEL4, which contains the PCR253 region, has only an additional 26 bp of upstream sequence.

Figure 14B:
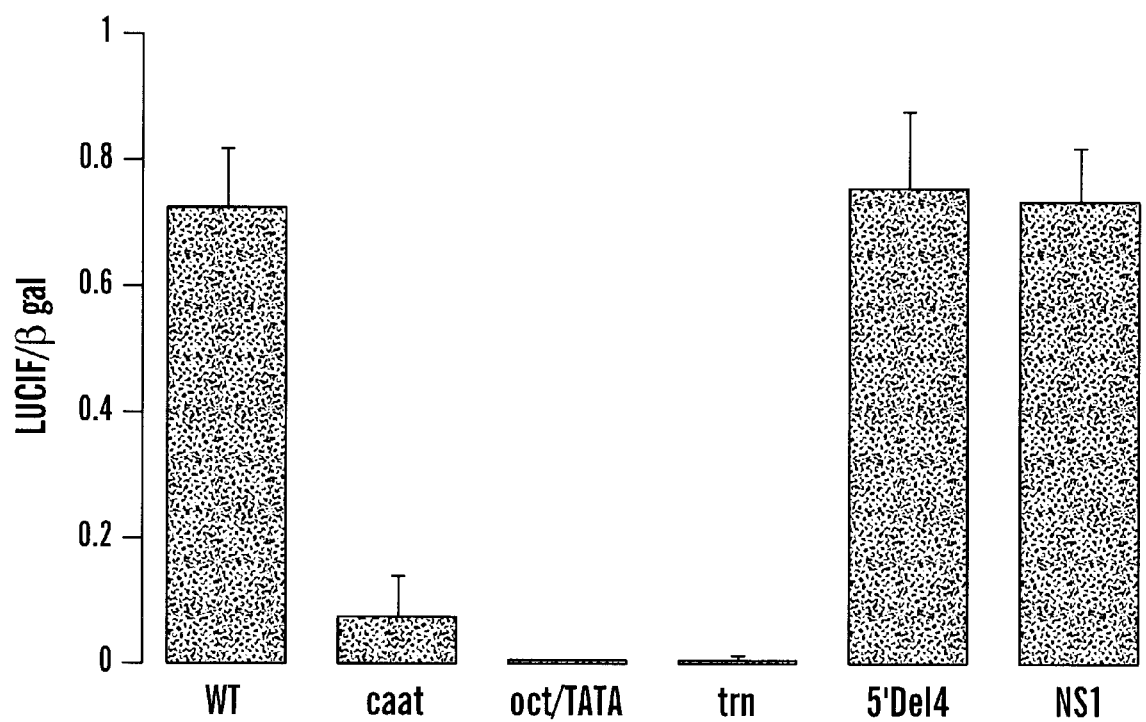

Internal deletions reveal the presence of important cis-acting regulatory elements Primary cultrues of rat neocortex were transfected with pGL-541 constructs that contained different internal deletions of the β1 5' flanking sequence. Mutations were generated by the method of Kunkel (1987, Proc. Natl. Acad Sci. 82:488). The results shown in FIG. 14B represent relative luciferase reporter gene activity when normalized to the activity of a co-transfected construct that contains a constitutive promoter driving the expression of the β-galactosidase gene (β1 promoter activity=78+/−8.9% of constitutive). The constructs are distinguished by their absence of either the CAAT box at −203 (activity=7.8+/−5.9% of constitutive), the octamer/reverse TATA sequence at −69 (activity=7.6+/−0.1% of constitutive), or the major transcriptional start site from −3 to +16 (activity=1.2+/−0.5% of constitutive). Identification of the contribution of the CAAT box and octamer/TATA binding sequence to promoter activity is especially important given the fact that other internal deletions are without effect. Interestingly, deletion of the sequence from −142 to −174, present in 5' DEL4, does not produce a change in promoter activity, suggesting that the enhancer detected from 5' deletional analysis is a cryptic enhancer. However, because transient transfection does not produce integration of reporter constructs into chromatin structure, it is quite possible that the sequence contained within the −142 to −174 region is important for promoter activity in vivo. Likewise, removal of the sequence spanning −106 to −122 does not alter promoter activity in transient transfection. The identification of sequence specific binding proteins to this region suggests that it may also play a role in vivo. Removal of sequence at −67 to −83 is without effect as is removal of the AP1 sequence from −132 to −137.

4E. β1 Promoter displays species and neural specific promoter activity.

Figure 15:
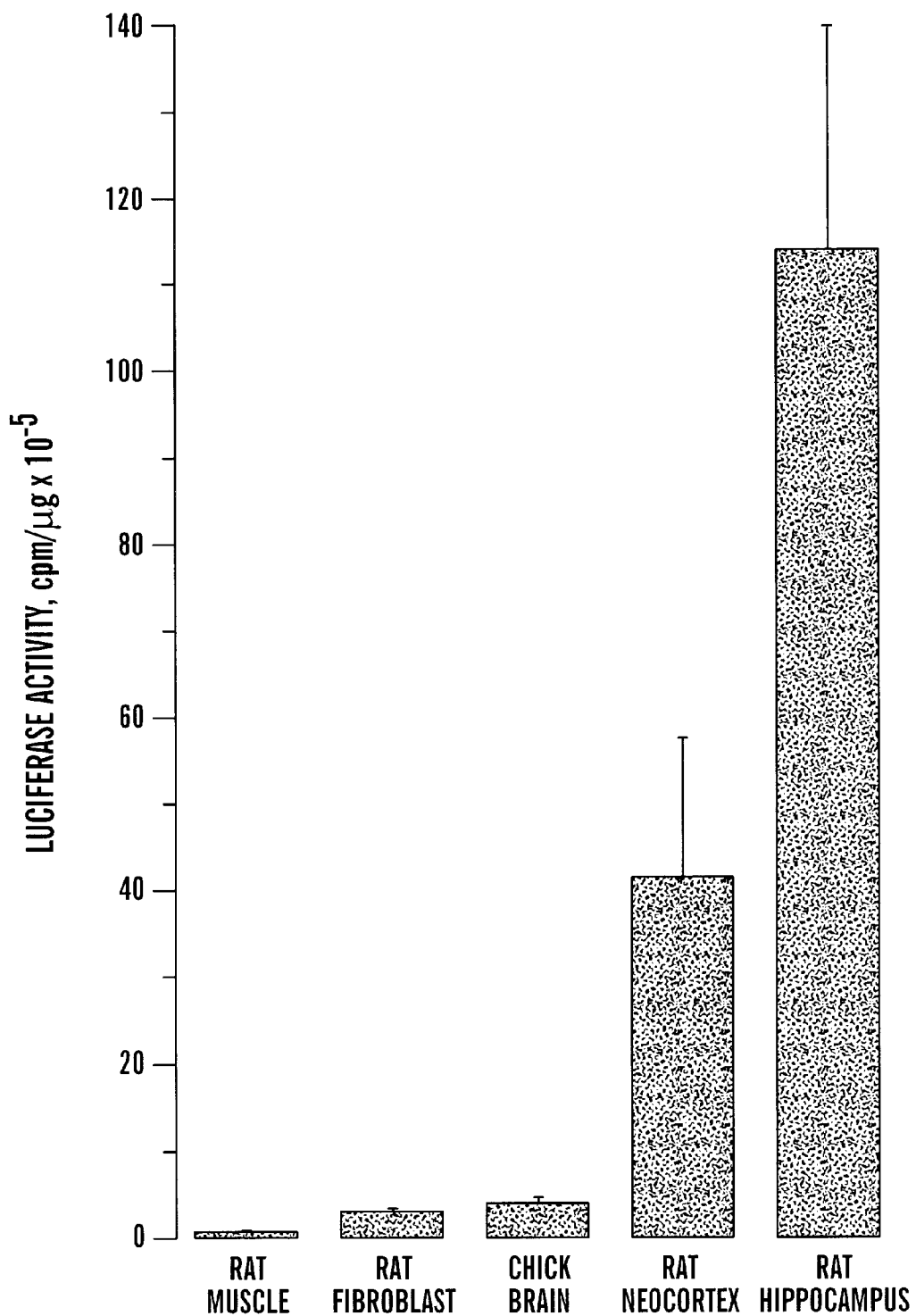
FIG. 15 shows that the promoter activity of PCR541 is species and tissue specific. Primary cultures of rat muscle, rat fibroblast, chick brain, rat neocortex, and rat fibroblast, chick brain, rat neocortex, and rat hippocampus were transfected with the luciferase construct pGLef-541 that contained 436 bp of 5' flanking region.

Primary cultures of rat muscle, neocortex, hippocampus and chick brain were transfected with pGLef-541. The results shown in FIG. 15 represent the mean luciferase activity ± standard error of n independent experiments using primary cultures of rat muscle (n=2), rat fibroblast (n=3), chick brain (n=5), rat neocortex (n=11), and rat hippocampus (n=7). At least two different preparations of DNA were used for each type of cell culture. Luciferase activity was the greatest in transfected rat hippocampal cultures, as might be expected since the β1 gene is most highly expressed in the adult hippocampus (Wisden et al., 1992) (FIG. 15). Furthermore, the tissue specific activity of the β1 promoter was not limited to PCR541, as PCR412 also displayed the greatest activity in primary cultures of rat hippocampus and neocortex, with no activity in fibroblasts. Although the activity of the Sv40 promoter and enhancer was the greatest in primary cultures was significantly less than in cultures of rat neocortex and hippocampus (FIG. 15). Again, although the Sv40 promoter and enhancer were highly active in primary cultures of chick brain, the level of β1 promoter activity in these cultures was also significantly less than in cultures of rat neocortex and hippocampus. These observations suggest that differences in promoter activity of the human β1 subunit gene are most likely due to differences in the species- and tissue-specific activity of the β1 promoter and not to variations in the transfectional efficiency of cells from different species and tissues.

EXAMPLE 5

The Regulation of Activity from the Human β1 Subunit Promoter

Chronic treatments

Primary cell culture was performed as described above. All cells were chronically treated on day 7. 500 μl of the conditioned medium was removed and mixed with an aliquot of the drug and then returned to the original dish. Dexamethasone and Ru486 were made up in 100% DMSO. GABA and SR95531 were dissolved in DMEM and GABA was made fresh every week. Twenty-nine hours after the first treatment the medium was replaced and then drugs were added as described above. Three, hours later the cells were transfected and subsequently assayed as described above.

5A. Chronic exposure of rat neocortical and hippocampal cultures to ethanol produces a specific decrease in β1 promoter activity.

Primary cultures of rat neocortex and rat hippocampus transfected with pGLef-541 were exposed to 102 mM ethanol for 19 hours. Ethanol was added three hours prior to transfection. Ethanol produced a 71+/−3.4% decrease in promoter activity in primary neocortical cultures (n+7) and a 62+/−5.3% decrease in promoter activity in primary cultures of hippocampal formation (n+5). The fact that β1 promoter activity is downregulated by ethanol, as are the mRNAs for various $GABA_A$ receptor subunits, taken together with the fact that a major effect fo ethanol is the alteration of $GABA_A$ receptor function, indicates that the β1 promoter assay can be a powerful tool to identify novel therapeutics for the treatment of alcoholism.

5B. Rat neocortical cultures chronic exposure to GABA produces a significant and specific decrease in β1 promoter activity.

Primary cultures of rat neocortex transfected with pGLef-541 were exposed to 0.5 mM GABA chronically for 48 hrs (n=5). After 32 hours of chronic treatment rat primary cultures were transfected with pGLef-541. The results shown represents the means ± standard errors of n independent experiments (GABA, n=5; GABA+SR95531, n=3). Effects of chronic drug treatment are displayed as % control, where control received vehicle only. At least 3 different preparations of DNA were used for each condition. Exposure to GABA produced a significant ($p<0.002$) decrease in promoter activity when compared to nontreated control cultures (43.4±7% of control) (cultures were ) (FIG. 16). When primary rat neocortical cultures were chronically exposed to 0.5 mM GABA and 0.25 mM SR95531 (a potent water soluble $GABA_A$ receptor antagonist) the effect of GABA treatment was reversed (118.67±18.7% of control (n=3) (FIG. 16).

To determine whether chronic treatment with GABA produced a decrease in the transfectional efficiency of primary cells in culture, co-transfection of rat neocortical cultures was performed using pGLef-541 and pSVβ, a β-galactosidase vector that contained the Sv40 promoter and enhancer. Cultures were chronically treated for 48 hours with either 0.5 mM GABA or 0.5 mM GABA and 0.25 mM SR95531. The results shown in FIG. 17 represent the means and standard errors of two independent experiments with each determination from duplicate dishes. Effects of chronic drug treatment are displayed as % control, where control received the vehicle only. Chronic treatment with GABA affected the promoter activity of the human β1 subunit gene (measured as luciferase expression) but did not affect the activity driven by the SV40 promoter (measured as β-galactosidase expression) (FIG. 17).

5C. Rat hippocampal cultures chronic exposure to GABA produces a significant and specific decrease in β1 promoter activity.

In four independent experiments primary cultures of rat hippocampus were chronically exposed to GABA. Primary cultures of rat hippocampus were chronically treated for 48 hours with either 0.5 mM GABA or 0.5 mM GABA and 0.25 mM SR95531. After 32 hours of chronic treatment rat primary cultures were transfected with pGLef-541. The results shown in FIG. 18 represent the means ± standard errors of four independent experiments with each determination derived from duplicate dishes. Effects of chronic drug treatment are displayed as % control, where control received the vehicle only. Four different preparations of DNA were used for each condition. Exposure to GABA produced a significant ($p<0.02$) decrease in activity when compared to nontreated control cultures (48±10% of control) (cultures were transfected with pGLef-541) (FIG. 18). When primary rat hippocampal cultures were exposed to 0.5 mM GABA and 0.25 mM SR95531, the effect of GABA treatment was significantly reversed (78±7% control) ($p<0.05$) (FIG. 18).

5D. The human β1 promoter is regulated by chronic exposure to steroids

In three independent experiments, primary cultures of rat hippocampus transfected with pGLef-541 were chronically exposed to dexamethasone. Primary cultures of rat hippocampus were chronically treated for 48 hours with either 500 nM dexamethasone or 500 nM dexamethasone and 1 μM RU486. After 32 hours of chronic drug treatment rat primary cultures were transfected with pGLef-541. The results shown in FIG. 19 represent the means ± standard errors of three independent experiments with each determination derived from duplicate dishes. Effects of chronic drug treatment are displayed as % control, where control received the vehicle only. Three different preparations of DNA were used for each condition. Exposure to dexamethasone produced a significant increase in the activity of the human β1 promoter when compared to nontreated control cultures (233±58% of control) (FIG. 19). When primary rat hippocampal cultures were exposed to 500 nM dexamethasone and 1 μM Ru486, a potent antagonist at the intracellular glucocorticoid receptor, the effect of dexamethasone treatment was reversed (96±2% control) (FIG. 19).

5E. The first intron of the human β1 gene dramatically decreases the activity of the human β1 promoter in non-hippocampal tissue.

While β1 promoter activity is significantly higher in hippocampal neurons, there is still activity of the promoter in primary cultures of rat neocortex, a region that contains low levels of endogenous β1 mRNAs. This finding suggests that there are other regulations not contained within PCR541 that finely tune expression of the β1 gene to particular brain neurons. We have identified a regulatory element downstream in the gene that sliences the activity of the promoter in all non-hippocampal cells under study (FIG. 20).

Primary cultures of dissociated rat muscle, rat fibroblast and rat neocortex were transfected with either pGLef-541 or pGLef-541IS$_1$. The luciferase construct pGLef-541IS$_1$ contained the first intron of the human β1 subunit gene downstream of the luciferase gene in reverse orientation. As displayed in FIG. 20, addition of the first intron of the human β1 subunit gene to pGLef-541 dramatically inhibited the activity of the human β1 promoter in all tissues tested except hippocampus. The results shown represent the means ± standard errors of two independent experiments with each determination derived from duplicate dishes. Two different preparations of DNA were used for each condition.

Figure 21:
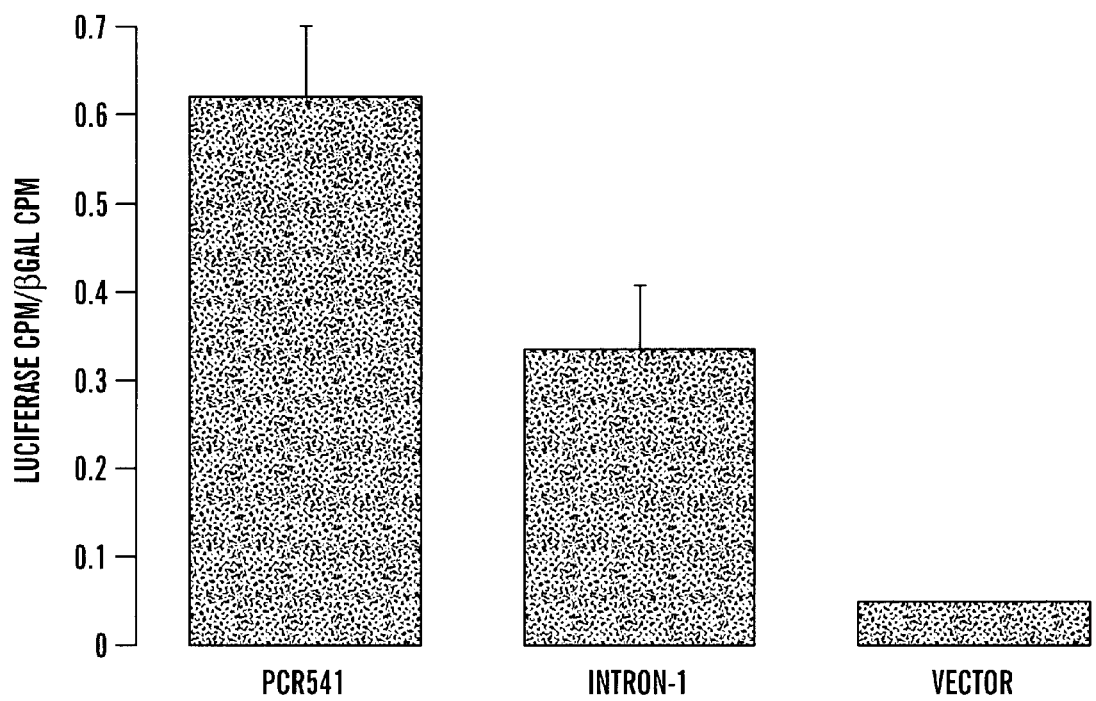
FIG. 21 shows promoter activity of the first intron of the β1 gene.

One possible mechanism for negative regulation by intron-1 is the generation of antisense transcripts that arrest translation in non-hippocampal tissues. This is supported by the fact that intron-1 can sustain promoter activity in neocortical and hippocampal cultures. FIG. 21 shows that when intron-1 is cloned in a forward orientation upstream of the luciferase reporter, gene activity (54% of the transcription with PCR541) is significantly above background levels (background=8% of PCR541, established by a promoterless vector).

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, recombinant DNA technology, pharmacology, gene therapy, and/or related fields are intended to be within the scope of the invention, which is limited only by the appended claims.

All publications and patent applications mentioned in this specification are indicative of the level of skill of those skilled in the art to which this invention pertains. All publications and patent applications identified herein are incorporated by reference to the same extent as if each individual publication or patent application was specifically and individually indicated to be incorporated by reference.

We claim:

1. An isolated DNA molecule comprising:
   a) a neuron-specific transcriptional promoter, which is more transcriptionally active in hippocampal cells than in neocortical cells, the promoter comprising a transcriptional initiation sequence element 5'-GCGCAGGTCCATTCGGGAAT-3' SEQ ID NO: 18, and sequence elements 5'-ACTAGGAATATTGTTTG-3' SEQ ID NO: 17 and 5'-GGACATGGAGCAC-3' SEQ ID NO: 19 positioned at least 35 nucleotide base pairs upstream from the transcription initiation sequence element; and
   b) a collection of one or more cis-acting elements, wherein said elements are CAAT boxes that confer orientation specificity on the transcriptional activity of the promoter, and are functionally located upstream from the promoter.

2. The isolated DNA molecule of claim 1, further comprising at least 4 sequential nucleotides from nucleotides 130 to 309 in SEQ ID NO: 37.

3. The isolated DNA molecule of claim 1, wherein said collection of cis-acting elements comprises a first sequence element upstream from a second sequence element, and both said first and said second sequence elements are 5'-CAAT-3'.

4. The isolated DNA molecule of claim 1, further comprising nucleotides 263 to 287 listed in SEQ ID NO: 37.

5. An isolated DNA molecule consisting essentially of:
   a) a neuron-specific transcriptional promoter, which is more transcriptionally active in hippocampal cells than in neocortical cells, the promoter consisting essentially of a transcription initiation site sequence element 5'-GCGCAGGTCCATTCGGGAAT-3' SEQ ID NO: 18, and sequence elements 5'-ACTAGGAATATTGTTTG-3' SEQ ID NO: 17 and 5'-GGACATGGAGCAC-3' SEQ ID NO: 19 positioned at least 35 nucleotide base pairs upstream from the transcription initiation site;
   b) a cis-acting element that is a CAAT box and is an orientation specific transcriptional stimulators element for the promoter, the cis-acting element being functionally located upstream from the promoter and comprising at least 4 sequential nucleotides corresponding to 4 sequential nucleotides from nucleotides 130 to 309 in SEQ ID NO: 37;
   c) an open reading frame comprising at least one exon of a protein coding sequence which is transcribed under control of the promoter; and
   d) a negative regulatory sequence element downstream from the promoter, the negative regulatory sequence element comprising all or a portion of Intron-1 of the β-1 subunit gene of GABA$_A$ receptor.

6. The isolated DNA molecule of claim 5, wherein the negative regulatory sequence element is part of an intron downstream from at least one exon in the open reading frame.

7. The isolated DNA molecule of claim 5, wherein the negative regulatory sequence element has transcriptional promoter activity for transcription in opposite orientation from RNA transcribed under control of the promoter.

8. The isolated DNA molecule of claim 7, wherein the transcriptional promoter activity of the negative regulatory sequence element is greater in neocortical cells than in hippocampal cells.

9. An isolated DNA molecule comprising:
   a) the orientation dependent neuron-specific transcriptional promoter and enhancer sequence corresponding to nucleotide 1–541 of SEQ ID NO: 37; and
   b) an heterologous open reading frame functionally linked to the promoter.

10. An isolated DNA molecule comprising:
    a) the orientation dependent neuron-specific transcriptional promoter and enhancer sequence corresponding to nucleotide 1–541 of SEQ ID NO: 37;
    b) an heterologous open reading frame functionally linked to the promoter; and
    c) Intron-1 of the β-1 subunit gene of GABA$_A$ receptor functionally linked in reverse orientation downstream of at least one exon in the heterologous open reading frame so as to function as a negative regulatory sequence element of the heterologous open reading frame in non-hippocampal cells.

11. An isolated DNA molecule comprising:
    a) the orientation dependent neuron-specific transcriptional promoter and enhancer sequence corresponding to nucleotide 130–541 of SEQ ID NO: 37; and b) an heterologous open reading frame functionally linked to the promoter.

12. An isolated DNA molecule comprising:
a) the orientation dependent neuron-specific transcriptional promoter and enhancer sequence corresponding to nucleotide 130–541 of SEQ ID NO: 37;
b) an heterologous open reading frame functionally linked to the promoter; and
c) Intron-1 of the β-1 subunit gene of $GABA_A$ receptor functionally linked in reverse orientation downstream of at least one exon in the heterologous open reading frame so as to function as a negative regulatory sequence element of the heterologous open reading frame in non-hippocampal cells.

13. The isolated DNA molecule of claim 12 wherein Intron-1 of the β-1 subunit gene of $GABA_A$ receptor is part of an intron downstream from at least one exon in the heterologous open reading frame.

14. An isolated DNA molecule comprising:
a) the orientation dependent neuron-specific transcriptional promoter and enhancer sequence corresponding to nucleotide 145–541 of SEQ ID NO: 37; and
b) an heterologous open reading frame functionally linked to the promoter.

15. An isolated DNA molecule comprising:
a) the orientation dependent neuron-specific transcriptional promoter and enhancer sequence corresponding to nucleotide 145–541 of SEQ ID NO: 37;
b) an heterologous open reading frame functionally linked to the promoter; and
c) Intron-1 of the β-1 subunit gene of $GABA_A$ receptor functionally linked in reverse orientation downstream of at least one exon in the heterologous open reading frame so as to function as a negative regulatory sequence element of the heterologous open reading frame in non-hippocampal cells.

16. The isolated DNA molecule of claim 15 wherein Intron-1 of the β-1 subunit gene of $GABA_A$ receptor is part of an intron downstream from at least one exon in the heterologous open reading frame which it negatively regulates.

17. An isolated DNA molecule comprising:
a) the orientation dependent neuron-specific transcriptional promoter and enhancer sequence corresponding to nucleotide 217–541 of SEQ ID NO: 37; and
b) an heterologous open reading frame functionally linked to the promoter.

18. An isolated DNA molecule comprising:
a) the orientation dependent neuron-specific transcriptional promoter and enhancer sequence corresponding to nucleotide 217–541 of SEQ ID NO: 37;
b) an heterologous open reading frame functionally linked to the promoter; and
c) Intron-1 of the β-1 subunit gene of $GABA_A$ receptor functionally linked in reverse orientation downstream of at least one exon in the heterologous open reading frame so as to function as a negative regulatory sequence element of the heterologous open reading frame in non-hippocampal cells.

19. The isolated DNA molecule of claim 18 wherein Intron-1 of the β-1 subunit gene of $GABA_A$ receptor is part of an intron downstream from at least one exon in the heterologous open reading frame which it negatively regulates.

20. An isolated DNA molecule comprising:
a) the orientation dependent neuron-specific transcriptional promoter and enhancer sequence corresponding to nucleotide 241–541 of SEQ ID NO: 37; and
b) an heterologous open reading frame functionally linked to the promoter.

21. An isolated DNA molecule comprising:
a) the orientation dependent neuron-specific transcriptional promoter and enhancer sequence corresponding to nucleotide 241–541 of SEQ ID NO: 37;
b) an heterologous open reading frame functionally linked to the promoter; and
c) Intron-1 of the β-1 subunit gene of $GABA_A$ receptor functionally linked in reverse orientation downstream of at least one exon in the heterologous open reading frame so as to function as a negative regulatory sequence element of the heterologous open reading frame in non-hippocampal cells.

22. The isolated DNA molecule of claim 21 wherein Intron-1 of the β-1 subunit gene of $GABA_A$ receptor is part of an intron downstream from at least one exon in the heterologous open reading frame which it negatively regulates.

23. An isolated DNA molecule comprising:
a) the orientation dependent neuron-specific transcriptional promoter and enhancer sequence corresponding to nucleotide 130–509 of SEQ ID NO: 37; and
b) an heterologous open reading frame functionally linked to the promoter.

24. An isolated DNA molecular comprising:
a) the orientation dependent neuron-specific transcriptional promoter and enhancer sequence corresponding to nucleotide 130–509 of SEQ ID NO: 37;
b) an heterologous open reading frame functionally linked to the promoter; and
c) Intron-1 of the β-1 subunit gene of $GABA_A$ receptor functionally linked in reverse orientation downstream of at least one exon in the heterologous open reading frame so as to function as a negative regulatory sequence element of the heterologous open reading frame in non-hippocampal cells.

25. The isolated DNA molecule of claim 24 wherein Intron-1 of the β-1 subunit gene of $GABA_A$ receptor is part of an intron downstream from at least one exon in the heterologous open reading frame which it negatively regulates.

26. An isolated DNA molecular comprising:
a) The neuron-specific transcriptional promoter corresponding to nucleotide 152–541 of SEQ ID NO 37; and
b) an heterologous open reading frame functionally linked to the promoter.

27. An isolated DNA molecular comprising:
a) The neuron-specific transcriptional promoter corresponding to nucleotide 152–541 of SEQ ID NO 37;
b) an heterologous open reading frame functionally linked to the promoter; and
c) Intron-1 of the β-1 subunit gene of $GABA_A$ receptor functionally linked in reverse orientation downstream of at least one exon in the heterologous open reading frame so as to function as a negative regulatory sequence element of the heterologous open reading frame in non-hippocampal cells.

28. The isolated DNA molecule of claim 27 wherein Intron-1 of the β-1 subunit gene of $GABA_A$ receptor is part of an intron downstream from at least one exon in the heterologous open reading frame which it negatively regulates.

* * * * *

UNITED STATES PATENT AND TRADEMARK OFFICE
CERTIFICATE OF CORRECTION

PATENT NO. : 6,066,726
DATED      : May 23, 2000
INVENTOR(S): David H. Farb and Shelley J. Russek It is certified that error appears in the above-indentified patent and that said Letters Patent is hereby corrected as shown below:

Claim 5, line 64, delete "stimulators" and substitute therefor ---stimulatory---.

Claim 24, line 27, delete "molecular" and substitute therefor ---molecule---.

Claim 27, line 50, delete "molecular" and substitute therefor ---molecule---.

Signed and Sealed this

Twentieth Day of March, 2001

Attest:

NICHOLAS P. GODICI

Attesting Officer       Acting Director of the United States Patent and Trademark Office